United States Patent
Kalafatis et al.

(10) Patent No.: US 10,900,027 B2
(45) Date of Patent: Jan. 26, 2021

(54) RECOMBINANT PROTHROMBIN ANALOGUES AND USES THEREOF

(71) Applicant: Cleveland State University, Cleveland, OH (US)

(72) Inventors: Michael Kalafatis, Shaker Heights, OH (US); Joseph Wiencek, Cleveland, OH (US)

(73) Assignee: Cleveland State University, Cleveland, OH (US)

( * ) Notice: Subject to any disclaimer, the term of this patent is extended or adjusted under 35 U.S.C. 154(b) by 0 days.

(21) Appl. No.: 15/766,901

(22) PCT Filed: Oct. 7, 2016

(86) PCT No.: PCT/US2016/056049
§ 371 (c)(1),
(2) Date: Apr. 9, 2018

(87) PCT Pub. No.: WO2017/062802
PCT Pub. Date: Apr. 13, 2017

(65) Prior Publication Data
US 2018/0305677 A1   Oct. 25, 2018

Related U.S. Application Data

(60) Provisional application No. 62/239,535, filed on Oct. 9, 2015.

(51) Int. Cl.
| | | |
|---|---|---|
| *C12N 9/74* | (2006.01) | |
| *A61P 7/02* | (2006.01) | |
| *A61K 38/48* | (2006.01) | |
| *C12N 15/79* | (2006.01) | |
| *A61K 38/00* | (2006.01) | |

(52) U.S. Cl.
CPC ........ *C12N 9/6429* (2013.01); *A61K 38/4833* (2013.01); *A61P 7/02* (2018.01); *C12N 15/79* (2013.01); *C12Y 304/21005* (2013.01); *A61K 38/00* (2013.01)

(58) Field of Classification Search
None
See application file for complete search history.

(56) References Cited

U.S. PATENT DOCUMENTS 5,510,248 A   4/1996   Cote et al.

FOREIGN PATENT DOCUMENTS

WO   WO 2014/115087   *  7/2014

OTHER PUBLICATIONS

Banfield et al. ("Partial characterization of vertebrate prothrombin cDNAs: Amplification and sequence analysis of the B chain of thrombin from nine different species," Proceedings of the National Academy of Sciences, Apr. 1, 1992 (Apr. 1, 1992), vol. 89, No. 7, pp. 2//9-2/8J.).*
Wiencek et al., "The Regulatory Function of Amino Acid Region 473-487 of Prothrombin During Coagulation," Blood, ml. 122, No. 21, Nov. 2013 (cited in IDS Sep. 20, 2019).*
Wiencek et al., "The Dual Regulatory Role of Amino Acids Leu480 and Gln481 of Prothrombin," The Journal of Biological Chemistry, vol. 291, No. 4, pp. 1565-1581, Jan. 22, 2016 (cited in IDS Sep. 20, 2019).*
Extended European Search Report from EP Application No. 16854445.0 dated Feb. 15, 2019.
Wiencek et al., "The Regulatory Function of Amino Acid Region 473-487 of Prothrombin During Coagulation," Blood, vol. 122, No. 21, Nov. 2013.
Bode et al., The Refined 1.9 A Crystal Structure of Human a-Thrombin: Interaction with D-Phe-Pro-Arg Chloromethylketone and Significance of the Tyr-Pro-Pro-Trp Insertion Segment, The EMBO Journal, vol. 8, No. 11, pp. 3467-3475, 1989.
Myles et al., "An Extensive Interaction Interface between Thrombin and Factor V is Required for Factor V Activation" vol. 276, No. 127, Issue of Jul. 6, pp. 25143-25149, 2001.
Myles et al., "Structural Requirements for the Activation of Human Factor VIII by Thrombin," Blood, vol. 100, No. 8, Oct. 15, 2002.
Bode et al., "The Refined 1.9-A X-ray Crystal Structure of D-Phe-Pro-Arg Chloromethylketone-inhibited Human a-Thrombin: Structure Analysis, Overall Structure, Electrostatic Properties, Detailed Active-Site Geometry, and Structure-Function Relationships," Protein Science (1992), I , 426-471.1992.
Wiencek et al., "The Dual Regulatory Role of Amino Acids Leu480 and Gln481 of Prothrombin," The Journal of Biological Chemistry, vol. 291, No. 4, pp. 1565-1581, Jan. 22, 2016.

* cited by examiner

*Primary Examiner* — Maury A Audet
(74) *Attorney, Agent, or Firm* — Calfee, Halter & Griswold LLP

(57) ABSTRACT

During the process of coagulation, prothrombin is activated to α-thrombin by prothrombinase. Key residues in the structure of prothrombin allow for modulation of the activation of prothrombin. In certain embodiments, a recombinant prothrombin with at least one point mutation or deletion is provided.

11 Claims, 11 Drawing Sheets

Specification includes a Sequence Listing.

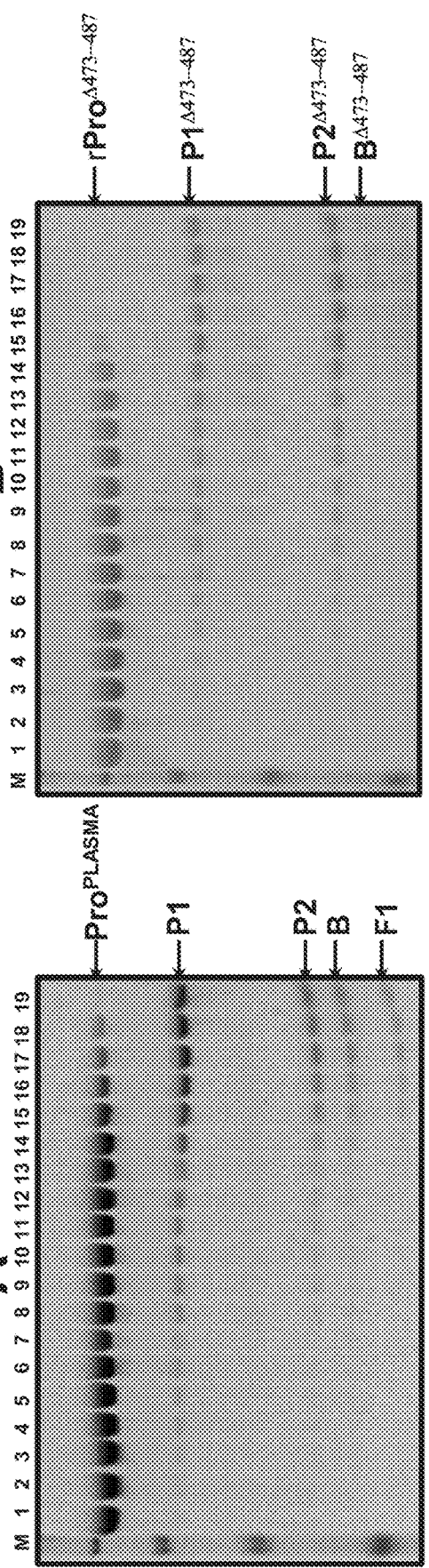
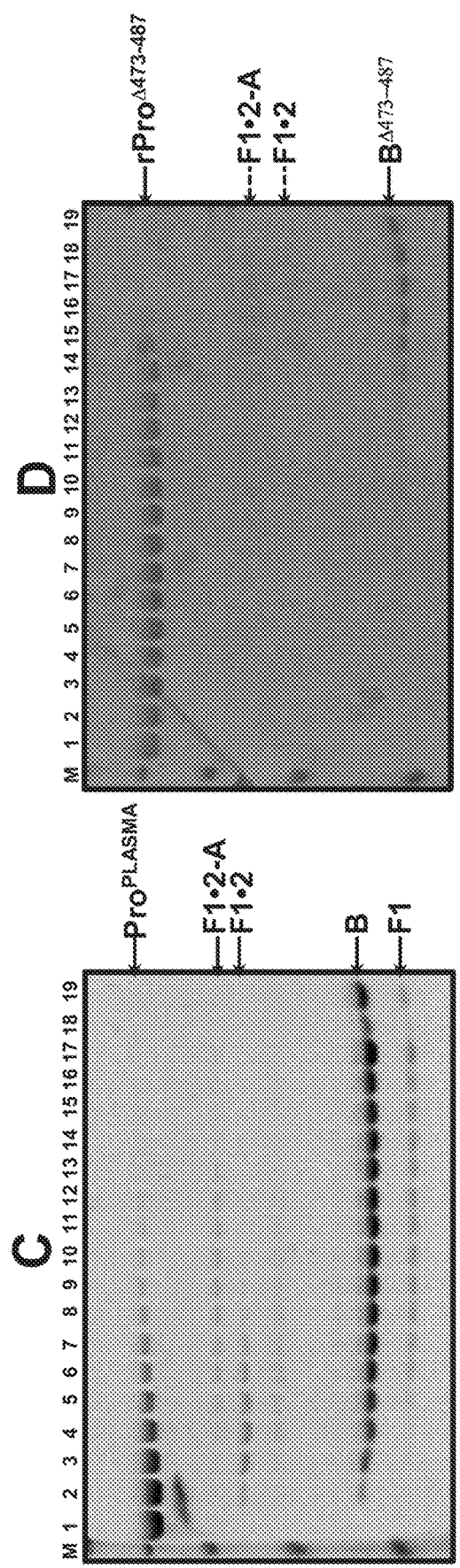
Fig. 3

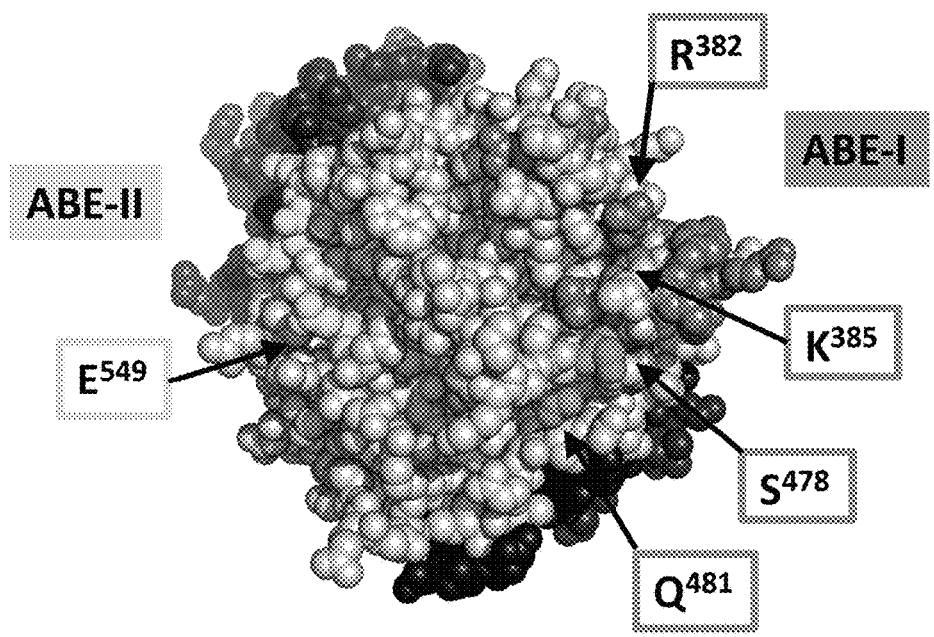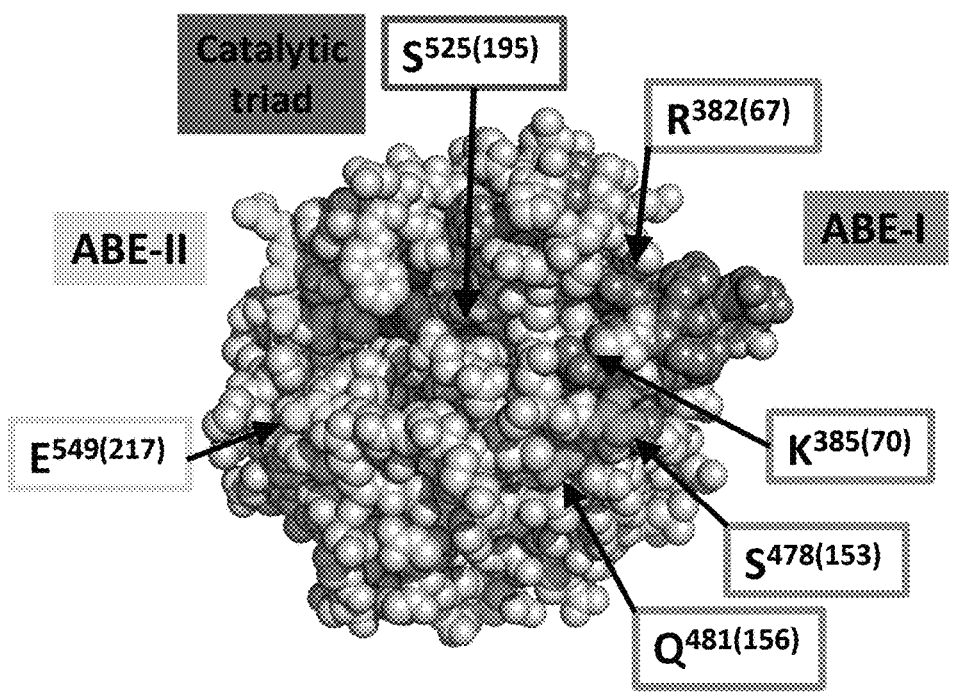
Fig. 11

RECOMBINANT PROTHROMBIN ANALOGUES AND USES THEREOF

CROSS-REFERENCE TO RELATED APPLICATIONS

This application is the U.S. National Stage Entry of PCT/US16/56049, filed on Oct. 7, 2016, which claims priority to and any benefit of U.S. Provisional Application No. 62/239,535, filed Oct. 9, 2015, the entire contents of which are incorporated herein by reference in their entirety.

REFERENCE TO A SEQUENCE LISTING SUBMITTED VIA EFS-WEB

The content of the ASCII text file of the sequence listing named 27433.04088-1_ST25.txt, which is 67 kb in size, was created on Jan. 10, 2019 and electronically submitted via EFS-web, is incorporated by reference in its entirety.

TECHNICAL FIELD

The present disclosure relates generally to the field of blood coagulation. More particularly, the present disclosure relates to modified recombinant prothrombin analogues and uses thereof.

BACKGROUND

During the final stages of blood coagulation, prothrombin (Pro) is converted to the serine protease thrombin, an enzyme which plays a central role in clot formation. Activation of prothrombin to thrombin results from the proteolytic cleavage by factor Xa and factor Va.

There are instances wherein it is advantageous to short-circuit the normal clotting mechanisms, or to modify over-active clotting mechanisms in an individual. For example, thrombosis is the formation of a blood clot inside a blood vessel, obstructing the flow of blood through the circulatory system. When a clot is significantly large enough to reduce the blood flow to a tissue, hypoxia can occur and metabolic products such as lactic acid can accumulate. A larger thrombus can cause a much greater obstruction to blood flow and may result in anoxia and, in certain circumstances, tissue death. There are also a number of other conditions that can arise according to the location of the thrombus and the organs affected. Conditions that put an individual at risk for thrombosis include, but are not limited to, pulmonary embolism, thrombophlebitis, deep vein thrombosis, arterial occlusion from thrombosis or embolism, arterial reocclusion during or after angioplasty or thrombolysis, restenosis following arterial injury or invasive cardiological procedures, postoperative venous thrombosis or embolism, acute or chronic atherosclerosis, stroke, myocardial infarction, cancer and metastasis, and neurodegenerative diseases. However, current anti-thrombotic therapies suffer from a number of drawbacks. Thus, it would be desirable to provide an anti-coagulant agent which inhibits coagulation with greater specificity and without the side effects of current therapies.

SUMMARY

While embodiments encompassing the general inventive concepts may take diverse forms, various embodiments will be described herein, with the understanding that the present disclosure is to be considered merely exemplary, and the general inventive concepts are not intended to be limited to the disclosed embodiments.

The embodiments relate to modulation of the blood coagulation process including administration of modified forms of prothrombin (Pro) and their use as anti-coagulants. Unlike native or wild type prothrombin, the resulting modified-prothrombin molecule is highly stable. This stability is achieved by amino acid modifications that disrupt necessary cleavage sites so that they are no longer recognized by the specific proteases that initiate clot formation.

In an exemplary embodiment, a novel recombinant prothrombin (rPro) polypeptide is provided which is characterized by having anti-coagulant activity and having the amino acid sequence of Pro with an amino acid modification at a residue between 473 and 487. In certain exemplary embodiments, at least one amino acid residue selected from $Ser^{478}$, $Leu^{480}$, and $Gln^{481}$ is modified.

In an exemplary embodiment, a method of inhibiting coagulation in a subject who has or is at risk of having thrombosis is provided. The method comprises administering the polypeptide(s) of the general inventive concepts to a subject who has or is at risk of having arterial thrombosis.

In an exemplary embodiment, an isolated polynucleotide is provided which encodes a polypeptide characterized by having anti-coagulant activity and having the amino acid sequence of prothrombin with amino acid modification at a residue from 473 to 487.

In an exemplary embodiment, a pharmaceutical composition comprising a recombinant prothrombin in combination with pharmaceutically acceptable carriers, vehicles, and/or adjuvants is provided.

BRIEF DESCRIPTION OF THE DRAWINGS

FIG. 3 is an analyses of $Pro^{PLASMA}$ and $rPro^{\Delta 473-487}$ molecules activation by membrane-bound fXa alone or prothrombinase. Panel A: $rPro^{PLASMA}$ (1.4 µM) in the presence of PCPS vesicles, DAPA, and membrane bound fXa alone (5 nM); panel B: $rPro^{\Delta 473-487}$ (1.4 µM) in the presence of PCPS vesicles, DAPA, and membrane bound fXa alone (5 nM). Panel C: $rPro^{PLASMA}$ (1.4 µM) in the presence of PCPS vesicles, DAPA, and prothrombinase (1 nM fXa and 20 nM fVa); panel D: $rPro^{\Delta 473-487}$ (1.4 µM) in the presence of PCPS vesicles, DAPA, and prothrombinase (1 nM fXa and 20 nM fVa). Aliquots were withdrawn at various time intervals and treated as described. M represents the lane with molecular weight markers (from top to bottom): 98000, 64000, 50000, and 36000, respectively. Lanes 1-19 show samples from the reaction mixture before (0 min) the addition of fXa and 20 s, 40 s, 60 s, 80 s, 100 s, 120 s, 150 s, 180 s, 210 s, 240 s, 5 min, 6 min, 10 min, 20 min, 30 min, and 60 min, 90 min, and 120 min respectively, after the addition of fXa. Following scanning densitometry as described in the Examples section, the data representing Pro consumption as a function of time (sec) were plotted using non-linear regression analysis according to the equation representing a first-order exponential decay and the rates of Pro consumption using the apparent first-order rate constant, k (s$^{-1}$) obtained directly from the fitted data, were calculated as described and are reported in Table 1. Pro derived fragments are identified to the right of panels A, B, C, and D as follows: Pro, Pro (amino acid residues 1-579); P1, prethrombin-1 (amino acid residues 156-579); F1•2-A, fragment 1•2-A chain (amino acid residues 1-320); F1•2, fragment 1•2 (amino acid residues 1-271); P2, prethrombin-2 (amino acid residues 272-579); B, B chain of IIa (amino acid residues 321-579); F1, fragment 1 (amino acid residues 1-155).

FIG. 11 is a representation of the location of exosites in the structures of prothrombin and thrombin. Representation of the high resolution crystal structures of Pro$^{WT}$ (A) and IIa (B). A) Space-filling representation of human Pro. Residues Ser$^{478}$, Leu$^{480}$, and Gln$^{481}$ are colored green; ABE-I and ABE-II residues are yellow and blue, respectively; the amino acids composing the catalytic triad are not solvent-accessible and thus not visible. Other catalytic domain residues are in light gray while those in fragment-1 and fragment-2 are in dark gray. B) Space-filling representation of IIa. Residues are colored as for Pro with the addition of catalytic triad residues His$^{363}$, Asp$^{419}$, and Ser$^{525}$ (red) which are partially solvent-accessible. In parentheses are the corresponding numbers according to the chymothrypsin numbering of IIa. Distances between the active Ser$^{525}$ side chain hydroxyl and several other amino acids of interest are: 17 Å to Gln$^{481}$ OE1/NE2; 15 Å to Glu$^{549}$ OE1; 17 Å to Arg$^{382}$ NH$_2$; 18 Å to Lys$^{385}$ NH$_2$. The polar atoms at the end of the side chains were used as a reference because these would presumably be involved in intermolecular interactions.

DETAILED DESCRIPTION

Figure 1:
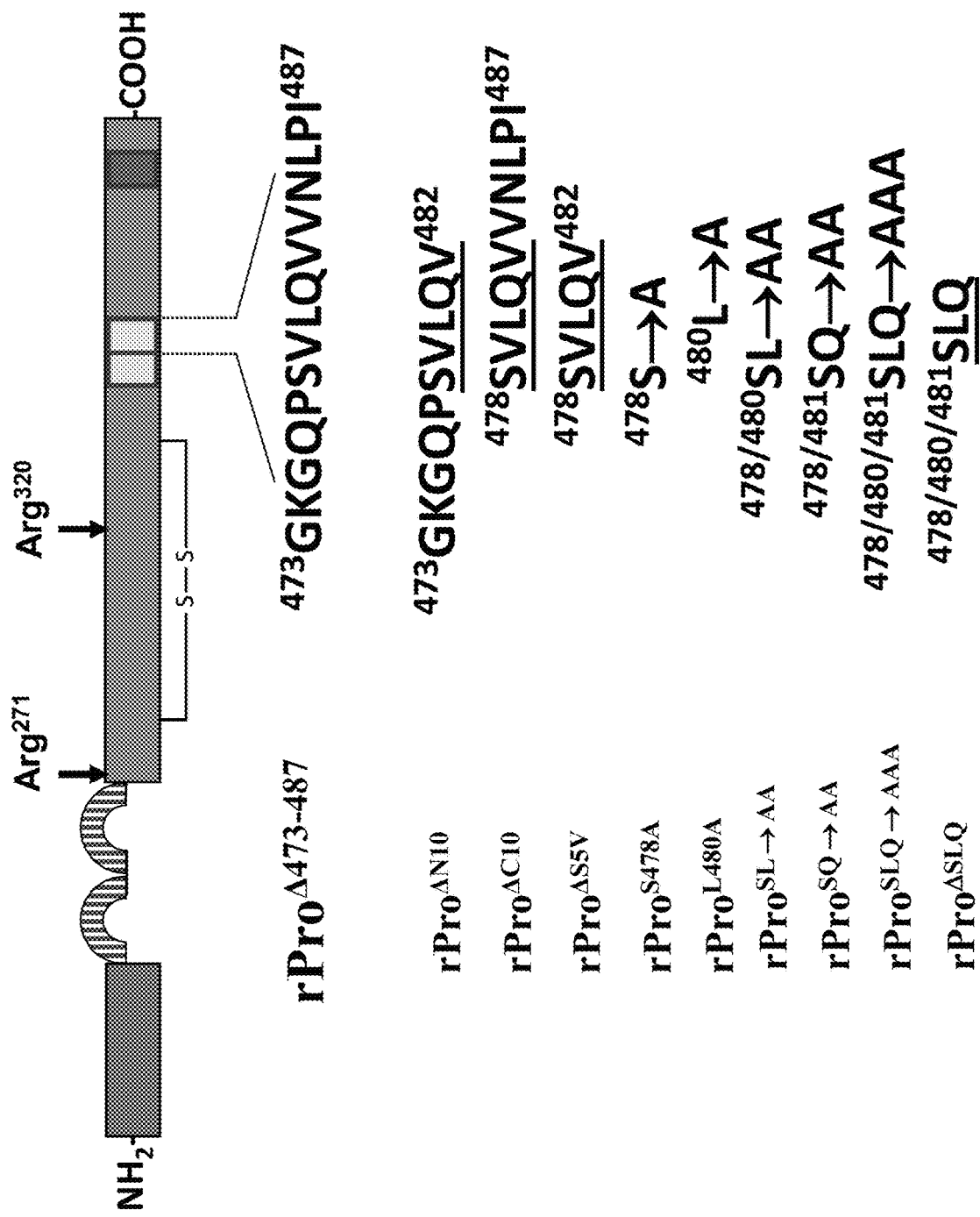
FIG. 1 is a schematic showing the pathways for Pro activation and several exemplary recombinant polypeptides according to various embodiments of the general inventive concepts. Pro is converted to IIa through two fXa-catalyzed cleavages at $Arg^{271}$ and at $Arg^{320}$ resulting in IIa formation. The red rectangle denotes the fVa-independent site for fXa on Pro while the yellow rectangle represents the fVa-dependent site for fXa studied herein. The light blue rectangle denotes the amino acids composing (pro)exosite I. All mutants used in the study are shown together with their assigned name used throughout the this disclosure.

Modification of prothrombin amino acid residues from 473 to 487, and in certain instances at least one amino acid residue selected from Ser$^{478}$, Leu$^{480}$, and Gln$^{481}$, allows for modulation of activity of the resulting polypeptide. While not wishing to be bound by theory, it is believed that by modifying the structure of a prothrombin polypeptide in residues from 473 to 487, the polypeptide may be recognized by prothrombinase but is not cleaved into an active form for clot formation. In other words, the modified prothrombin occupies, but is cleaved at a reduced rate by, prothrombinase, thereby slowing the production of thrombin. Thus, the more stable modified form can slow the normal clot-forming processes by slowing (or preventing) native prothrombin from being activated by prothrombinase.

Preferred polypeptides according to the general inventive concepts are therapeutic compounds that demonstrate anti-coagulant activity and may be used as antithrombotic agents. The term "therapeutic compound" as used herein means any compound which can be used in therapy, which implies the curing of a disease or malfunction of the body and which covers prophylactic treatment.

In an exemplary embodiment, a novel recombinant prothrombin (Pro) polypeptide is provided which is characterized by having anti-coagulant activity and having the amino acid sequence of Pro with amino acid modifications at residues between 473 and 487. In certain exemplary embodiments, at least one amino acid residue selected from Ser$^{478}$ Leu$^{480}$, and Gln$^{481}$ is modified. The recombinant prothrombin polypeptide of claim 1, wherein the modification occurs in at least one of amino acid residues Ser$^{478}$, Leu$^{480}$, and Gln$^{481}$. In certain exemplary embodiments, the modification is a deletion of at least one of amino acid residues Ser$^{478}$, Leu$^{480}$, and Gln$^{481}$. In certain exemplary embodiments, the modification is a modification of amino acid residue Ser$^{478}$. In certain exemplary embodiments, the modification is a modification of amino acid residue Leu$^{480}$. In certain exemplary embodiments, the modification is a modification of amino acid residue Gln$^{481}$. In certain exemplary embodiments, the modification is a modification of amino acid residues Ser$^{478}$, Leu$^{480}$, and Gln$^{481}$.

In an exemplary embodiment, a method of inhibiting coagulation in a subject who has or is at risk of having thrombosis is provided. The method comprises administering the polypeptide(s) of the general inventive concepts to a subject who has or is at risk of having arterial thrombosis.

In an exemplary embodiment, an isolated polynucleotide is provided which encodes a polypeptide characterized by having anti-coagulant activity and having the amino acid sequence of prothrombin with amino acid modification at a residue from 473 to 487.

Unlike native or wild type prothrombin, the resulting modified-prothrombin molecule is highly stable. This stability is achieved by amino acid modifications that disrupt necessary cleavage sites so that they are no longer recognized by the specific proteases that otherwise initiate clot formation.

In an exemplary embodiment, a method of inhibiting coagulation in a subject who has, or is at risk of having, thrombosis is provided. The method comprises administering the polypeptide(s) of the general inventive concepts to a subject who has, or is at risk of having, thrombosis.

In an exemplary embodiment, an isolated polynucleotide is provided which encodes a polypeptide characterized by having anti-coagulant activity and having the amino acid sequence of prothrombin with amino acid modification at a residue from 473 to 487.

In an exemplary embodiment, a pharmaceutical composition comprising a recombinant prothrombin in combination with pharmaceutically acceptable carriers, vehicles, and/or adjuvants is provided.

The general inventive concepts also provide a method for ameliorating thrombosis in a subject having, or at risk of having, thrombosis comprising administering a therapeutically effective amount of the polypeptide(s) described herein. As used herein, the term "ameliorate" denotes a lessening of the detrimental effects of thrombosis in the subject receiving therapy. The term "therapeutically effective" means that the amount of polypeptide used is of sufficient quantity to ameliorate or modulate the effects of the thrombosis.

The term "anti-coagulant activity" as used herein, when referring to the inventive methods and compositions described herein, refers to reduced coagulant or procoagulant activity relative to a wild-type or native polypeptide. In certain exemplary embodiments, the inventive polypeptides demonstrate anti-coagulant activity that is reduced by at least 10% relative to the native polypeptide (i.e., the activity is reduced by 10% to 100%). In certain exemplary embodiments, the inventive polypeptides demonstrate anti-coagulant activity that is reduced by at least 20% relative to the native polypeptide. In certain exemplary embodiments, the inventive polypeptides demonstrate anti-coagulant activity that is reduced by at least 40% relative to the native polypeptide. In certain exemplary embodiments, the inventive polypeptides demonstrate anti-coagulant activity that is reduced by at least 60% relative to the native polypeptide. In certain exemplary embodiments, the inventive polypeptides demonstrate anti-coagulant activity that is reduced by at least 80% relative to the native polypeptide. In certain exemplary embodiments, the inventive polypeptides demonstrate anti-coagulant activity that is reduced by at least 90% relative to the native polypeptide. In certain exemplary embodiments, the inventive polypeptides demonstrate anti-coagulant activity that is reduced by at least 95% relative to the native polypeptide. Anti-coagulant activity may be determined by methods such as those described in the Examples section, including but not limited to in vitro determination.

The terms "susceptible" and "at risk" as used herein, unless otherwise specified, mean having resistance to a certain condition or disease that is reduced relative to the population as a whole, including being genetically predisposed, having a family history of, and/or having symptoms of the condition or disease.

The terms "modulating" or "modulation" or "modulate" as used herein, unless otherwise specified, refer to the targeted movement of a selected characteristic.

The term "modification" as used herein, when referring to an amino acid sequence, unless otherwise specified, refers to a substitution of one amino acid for another, including deletion of the original amino acid.

The polypeptides of the general inventive concepts are a derivative of a naturally occurring physiologic human protein. Due to their specificity of action and dosage requirements, the polypeptides of the general inventive concepts may prove superior to other available antithrombotic agents in terms of at least one of bleeding tendency, toxicity, antigenicity, clearance rate, general side effects, and allergic reactions. Therefore, administration of the polypeptides of the general inventive concepts, alone or in combination with other thrombolytic or fibrinolytic agents, may prove useful in various clinical situations.

Minor modifications of the primary amino acid sequence of the polypeptides of the general inventive concepts may result in polypeptides which have substantially equivalent activity as compared to the specific polypeptides described herein. Such modifications may be deliberate, as by site-directed mutagenesis, or may be spontaneous. All of the polypeptides produced by these modifications are included herein as long as the biological activity of the inventive polypeptide still exists. For example, a modified polypeptide must still contain the cleavage sites which cannot be recognized by the specific protease. Further, deletion of one or more amino acids can also result in a modification of the structure of the resultant molecule without significantly altering its biological activity. This can lead to the development of a smaller active molecule which would also have utility. For example, it may be possible to remove amino or carboxy terminal amino acids which may not be required for biological activity of the particular polypeptide.

In addition to the discrete proteolytic sites described herein, the exemplary embodiments embrace conservative variations in the remaining amino acid sequence of the polypeptide of this disclosure. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term does not refer to the specific cleavage sites indicated herein.

The exemplary embodiments also relate to polynucleotides which encode the polypeptides of the general inventive concepts. As used herein, "polynucleotide" refers to a polymer of deoxyribonucleotides or ribonucleotides, in the form of a separate fragment or as a component of a larger construct. DNA encoding a peptide of the general inventive concepts can be assembled from cDNA fragments or from oligonucleotides which provide a synthetic gene which is capable of being expressed in a recombinant transcriptional unit. Polynucleotide sequences of the general inventive concepts include DNA, RNA, and cDNA sequences. A polynucleotide sequence can be deduced from the genetic code, however, the degeneracy of the code must be taken into account. Polynucleotides of the general inventive concepts include sequences which are degenerate as a result of the genetic code.

In certain embodiments, the relevant polynucleotide sequences may be inserted into a recombinant expression vector. The term "recombinant expression vector" refers to a plasmid, virus, or other vehicle known in the art that has been manipulated by insertion or incorporation of the genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells.

The exemplary embodiments also provide a method for producing a polypeptide which acts as a prothrombin molecule which is activated at a reduced rate, including polypeptides which cannot be activated. The method includes the steps of introducing into a host cell an expression vector which contains a nucleotide sequence which encodes a polypeptide which acts as an inactive prothrombin molecule and is incapable of activation; culturing the host cell in an appropriate medium; and isolating the polypeptide product encoded by the expression vector.

Based on the foregoing, because some of the method embodiments of the present disclosure are directed to specific subsets or subclasses of identified individuals (that is, the subset or subclass of individuals "in need" of assistance in addressing one or more specific diseases or specific conditions noted herein), not all individuals will fall within the subset or subclass of individuals as described herein for certain diseases or conditions.

In the presence of a procoagulant membrane surface and divalent metal ions, factor Va (fVa) binds factor Xa (fXa) to form prothrombinase. Prothrombinase is the two subunit enzymatic complex where the non-enzymatic regulatory subunit (fVa) controls the rate and directs cleavage of Pro by the catalytic subunit (fXa) at two spatially distinct sites resulting in timely α-thrombin (IIa) formation at the place of vascular injury. Cleavage at $Arg^{271}$ and $Arg^{320}$ of Pro is required to form the active serine protease IIa. The essential IIa molecule bears strong homology with other serine protease enzymes, such as activated protein C (APC), chymotrypsin, and fXa. Several different numberings of IIa residues appear in the literature based on either the chymotrypsin numbering, or IIa numbering, or the entire Pro sequence. The latter nomenclature is used herein with the appropriate chymotrypsin numbering in parenthesis when required for comparison with the existing literature.

Historically, it has been shown that in the absence of fVa, initial cleavage at Arg$^{271}$ of Pro results in the generation of the inactive intermediate prethrombin-2 and fragment 1•2. Further cleavage of prethrombin-2 at Arg$^{320}$ generates IIa (prethrombin-2 pathway) (FIG. 1). Concurrent with the appearance of excess fVa during clotting, the order of cleavages is reversed, and initial cleavage at Arg$^{320}$ generates a transient enzymatically active intermediate, meizothrombin, that has much higher catalytic efficiency than IIa towards chromogenic substrates usually employed to assess IIa activity. Meizothrombin is cleaved at Arg$^{271}$ resulting in the generation of IIa and fragment 1•2 (meizothrombin pathway). While efficient cleavage at each site requires the presence of phospholipids, initial cleavage at Arg$^{320}$ is entirely fVa-dependent.

In the absence of fVa, Pro is activated at a slow non-physiological rate by membrane-bound fXa alone. Interactions between fXa and Pro are known to exist in the presence and absence of fVa, however, the enhanced activity of fXa within prothrombinase is controlled solely by the non-enzymatic cofactor. Consequently, the innate process of coagulation rests on specific molecular interactions involved in the fVa-dependent activation of Pro by prothrombinase. In relation to fXa alone, the relative rate of IIa formation by prothrombinase is increased by 300,000-fold because of the increase in the rates of both Pro cleavages. This increase is mainly associated with a large (3,000-fold) increase in the $k_{cat}$ of fXa within prothrombinase with a modest 100-fold decrease in the $K_m$ of the enzyme. This substantial increase in enzymatic activity resulting in rapid IIa generation is credited through precise and unique interactions of the cofactor with specific amino acids affiliated with both membrane-bound fXa and membrane-bound Pro as recently demonstrated. Accordingly, the introduction of the non-enzymatic cofactor into prothrombinase equips the organism's coagulation artillery necessary for the explosive arrest of vasculature bleeding.

Factor V (fV) is a large quiescent multi-domain (A1-A2-B-A3-C1-C2) protein that circulates in blood at a concentration of 20 nM. Three sequential cleavages of fV at Arg$^{709}$, Arg$^{1018}$, and Arg$^{1545}$ by IIa and/or fXa release the B domain and promote formation of the active cofactor, fVa. Pro circulates abundantly in blood at a concentration of 1.4 µM as the zymogen form of the serine protease IIa. Mature Pro protein is composed of a region containing several post-translationally modified γ-carboxyglutamic acid residues (described as the Gla domain, residues 1-46), followed by two kringle domains (residues 65-143 and 170-248, respectively) and a serine protease domain (residues 272-579, FIG. 1). Pro contains three linkers: linker 1 (residues 47-64) connects the Gla domain to kringle-1, linker 2 (residues 144-169) connects the two kringles, and linker 3 (residues 249-284) connects kringle-2 to the A-chain portion of IIa.

The necessary fVa-dependent activation of Pro by prothrombinase is a widely studied mechanism of coagulation but still poorly understood. Numerous fVa binding sites are acknowledged to exist on Pro. Earlier investigations have showed the existence of binding sites on Pro for fVa in each of the kringle domains, and within the Gla domain. Furthermore, significant protein-protein interactions between the acidic COOH-terminal region of fVa and a region rich in basic amino acids of Pro have been inferred and characterized indirectly by employing molecular techniques involving specific hirudin-like ligands and the anion binding (pro)exosite I (ABE I) of Pro derivatives, as well as directly using a specific acidic peptide derived from the COOH-terminal region of the fVa heavy chain and recombinant fVa molecules. Site-directed mutagenesis of these basic residues generated a recombinant prothrombin molecule impaired in its ability to fully interact with fVa during complex formation. While a crystal structure and a model of fVa have been available for some time now, the crucial interaction of the acidic hirudin-like COOH-terminal portion of the heavy chain of the cofactor with Pro required for efficient IIa formation was initially ignored because it was missing from the crystal structure of the cofactor. This interaction was further discounted without providing any solid evidence in spite of initial findings by Guinto and Esmon and more recent original findings from our laboratory. A very recent model of prothrombinase, using as a template the crystal structure of prothrombinase from the snake venom of *Pseudonaja textilis*, verified and established the critical role of the acidic COOH-terminal region of fVa heavy chain for timely Pro cleavage and activation at two spatially distinct sites by prothrombinase.

Additional studies with several recombinant prethrombin-1 molecules, where seven critical basic amino acids within (pro)exosite 1 were changed to glutamic acid confirmed the interaction of (pro)exosite I with fVa acidic regions. Notably, the data revealed that while mutated prethrombin-1 is a poor substrate for prothrombinase, the same molecule was activated by membrane-bound fXa alone with similar rates as wild type prethrombin-1. Supplementary to these studies, Yegneswaran et al., utilizing synthetic peptides derived from a highly conserved region of Pro, postulated the existence of a fVa-dependent binding exosite for fXa within the sequence 473-487 (chymotrypsin numbering 149D-163) of Pro that is in close spatial arrangement to the (pro)exosite I. Although the authors suggested an important scaffold for a fVa-dependent binding exosite for fXa on Pro, their peptide studies discounted the importance of a minimal but significant stretch of amino acids within the region composed of amino acids 478-482 (Ser-Val-Leu-Gln-Val, chymotrypsin numbering 153-157) of Pro. The same authors have also identified a fVa-independent site for fXa on prothrombin (amino acids 557-571).

The study described below was initiated in order to identify and investigate the identity and role of the minimum important amino acids within the stretch 478-482 of Pro that is conserved in a wide-range of mammalian species and regulates peptide bond specificity and Pro activation by prothrombinase in a fVa-dependent manner. Our unexpected and original findings provide evidence that specific amino acids within Pro have a dual role in providing for both, a fVa-dependent exosite for fXa for efficient Pro activation required for timely cleavage at Arg$^{320}$, while also serving as the newly defined important exosite for proper and efficient tethering of IIa's physiological substrates, which in turn is required for optimum physiological IIa activity.

EXAMPLES

The following examples illustrate specific embodiments and/or features of the general inventive concepts. The examples are given solely for the purpose of illustration and are not to be construed as limitations of the present disclosure, as many variations thereof are possible without departing from the spirit and scope of the disclosure.

Materials.

Phenylmethylsulfonylfluoride (PMSF), O-phenylenediamine (OPD) dihydrochloride, N-[2-Hydroxyethyl]piperazine-N'-2-ethanesufonic acid (Hepes), Trizma (Tris base), and Coomasie Blue R-250 were purchased from Sigma (St. Louis, Mo.). fV-deficient plasma was purchased from Research Protein Inc. (Essex Junction, Vt.). Secondary anti-mouse, anti-sheep, and anti-equine IgG coupled to peroxidase were from Southern Biotechnology Associates Inc. (Birmingham, Ala.). L-α-phosphatidylserine (PS) and L-α-phosphatidylcholine (PC) were from Avanti Polar Lipids (Alabaster, Ala.). Chemiluminescent reagent ECL Plus, Heparin-Sepharose, MonoQ 5/50 columns were from GE Healthcare Life Sciences (Pittsburgh, Pa.). Normal reference plasma and chromogenic substrate Spectrozyme-TH were from American Diagnostica Inc. (Greenwich, Conn.). S-2238 was from AnaSpec (Fremont, Calif.) and recombiPlasTin used in the clotting assays was purchased from Instrumentation Laboratory Co (Lexington, Mass.). The reversible fluorescent IIa inhibitor dansylarginine-N-(3-ethyl-1,5-pentanediyl) amide (DAPA), human plasma-derived PC human-plasma-derived IIa, human plasma-derived Pro, and Pro-deficient plasma were purchased from Haematologic Technologies Inc. (Essex Junction, Vt.). The purified human plasma-derived protein C (PC) preparation used contained both heavy chains isoforms that are activated to activated protein C (APC) with similar rates as described earlier. Human fXa was purchased from Enzyme Research Laboratories (South Bend, Ind.). The plasmid pZEM229R-lite encoding human recombinant prothrombin (rPro) was a generous gift from Dr. Kathleen Berkner (Cleveland Clinic Foundation, Cleveland, Ohio). QuikChange® II XL Site Directed Mutagenesis Kit was obtained from Agilent Technologies Genomics (Santa Clara, Calif.). All molecular biology and tissue culture reagents, specific primers, and medium were obtained from Gibco, Invitrogen Corp. (Grand Island, N.Y.) or as indicated. Monoclonal antibodies to fV (αHFV$_{HC}$17 and αHFV$_{LC}$9), monoclonal antibody αHFV1 coupled to Sepharose used to purify plasma and recombinant fV molecules, and a polyclonal antibody to Pro used for immunoblotting experiments during rPro production were provided by Dr. Kenneth G. Mann (Department of Biochemistry, University of Vermont, Burlington, Vt.). Plasma factor V (fV$^{PLASMA}$) and plasma fVa (fVa$^{PLASMA}$) were purified as previously described.

Construction of rPro Molecules.

To investigate the importance of amino acid region 473-487 of the serine protease domain of Pro, we first constructed a recombinant mutant Pro molecule with this region deleted (rPro$^{\Delta 473-487}$) using Stratagene's QuikChange® site-directed mutagenesis kit and the pZEM229R-lite plasmid. rPro$^{\Delta 473-487}$ was constructed using the mutagenic primers 5'-GAG ACG TGG ACA GCC AAC GTT GTG GAG CGG CCG GTC TGC AAG-3' (sense) and 5'-CTT GCA GAC CGG CCG CTC CAC AAC GTT GGC TGT CCA CGT CTC-3' (antisense) (corresponding to the $^{473}$GKGQPSVLQVVNLPI$^{487}$ deletion). The mutation was confirmed by DNA sequencing (DNA Analysis Facility, Department of Molecular Cardiology at The Learner Research Institute, Cleveland Clinic, Cleveland Ohio).

To further investigate the minimum sequence of amino acids required for the fVa-dependent fXa binding on Pro within the region 473-487 of the serine protease domain, several rPro molecules with the mutations denoted as rPro$^{\Delta N10}$, rPro$^{\Delta C10}$, rPro$^{\Delta S5V}$, rPro$^{S478A}$, rPro$^{L480A}$, rPro$^{SL\rightarrow AA}$, rPro$^{SQ\rightarrow AA}$ and rPro$^{SLQ\rightarrow AAA}$ (FIG. 1) were constructed using Stratagene's QuikChange® Site-Directed Mutagenesis Kit and the pZEM229R-lite plasmid. First, overlapping deletions in the region 473-487 were constructed using the mutagenic primers for rPro$^{\Delta N10}$ 5'-G ACG TGG ACA GCC AAC GTT GTG AAC CTG CCC ATT GTG GAG-3' (sense) and 5'-CTC CAC AAT GGG CAG GTT CAC AAC GTT GGC TGT CCA CGT C-3' (antisense) (corresponding to the $^{473}$GKGQPSVLQV$^{482}$ deletion), while mutagenic primers used for rPro$^{\Delta C10}$ were 5'-GTT GGT AAG GGG CAG CCC GTG GAG CGG CCG GTC TGC-3' (sense) and 5'-GCA GAC CGG CCG CTC CAC GGG CTG CCC CTT ACC AAC-3' (antisense) (corresponding to the $^{478}$SVLQVVNLPI$^{487}$ deletion). Similarly, the middle deletion of the overlapping mutations rPro$^{\Delta S5V}$ was constructed using the mutagenic primers 5'-GTT GGT AAG GGG CAG CCC GTG AAC CTG CCC ATT GTG-3' (sense) and 5'-CAC AAT GGG CAG GTT CAC GGG CTG CCC CTT ACC AAC-3' (antisense) (corresponding to the $^{478}$SVLQV$^{482}$ middle deletion). Next, within the sequence 478-482, several point mutations were made based on amino acid solvent exposure and homology within other proteins. The first rPro point alanine mutation rPro$^{S478A}$ was constructed using the mutagenic primers 5'-GGT AAG GGG CAG CCC GCA GTC CTG CAG GTG-3' (sense) and 5'-CAC CTG CAG GAC TGC GGG CTG CCC CTT ACC-3' (antisense) (corresponding to the Ser$^{478}$→Ala mutation). The next single point mutation rPro$^{L480A}$ was constructed using the mutagenic primers 5'-GGG CAG CCC AGT GTC GCG CAG GTG GTG AAC CTG CCC-3' (sense) and 5'-GGG CAG GTT CAC CAC CTG CGC GAC ACT GGG CTG CCC-3' (antisense) (corresponding to the L$^{480}$→A mutation). In addition to single point mutations, we constructed two double alanine mutations, rPro$^{SL\rightarrow AA}$ and rPro$^{SQ\rightarrow AA}$, within the stretch 478-482 of Pro. For rPro$^{SL\rightarrow AA}$ we used the mutagenic primers 5'-GGT AAG GGG CAG CCC GCA GTC GCG CAG GTG GTG AAC CTG-3' (sense) and 5'-CAG GTT CAC CAC CTG CGC CAC TGC GGG CTG CCC CTT ACC-3' (antisense) (corresponding to the Ser$^{478}$/Leu$^{480}$→AA mutation). Also, for rPro$^{SQ\rightarrow AA}$, we used the mutagenic primers 5'-GGT AAG GGG CAG CCC GCA GTC CTG GCG GTG GTG AAC CTG-3' (sense) and 5'-CAG GTT CAC CAC CGC CAG GAC TGC GGG CTG CCC CTT ACC-3' (antisense) (corresponding to the Ser$^{478}$/Gln$^{481}$→AA mutation). Lastly, we constructed a Pro molecule with a triple mutation, rPro$^{SLQ\rightarrow AAA}$ with the mutagenic primers 5'-GGT AAG GGG CAG CCC GCA GTC GCG GCG GTG GTG AAC CTG-3' (sense) and 5'-CAG GTT CAC CAC CGC CGC CGC GAC TGC GGG CTG CCC CTT ACC-3' (antisense) (corresponding to the Ser$^{478}$/Leu$^{480}$/Gln$^{481}$→AAA mutation) and a rPro molecule with Ser$^{478}$/Leu$^{480}$/Gln$^{481}$ deleted (rPro$^{\Delta SLQ}$) using the mutagenic primers: 5'-GGT AAG GGG CAG CCC GTC GTG GTG AAC CTG CCC-3' (sense) and 5'-GGG CAG GTT CAC CAC GAC GGG CTG CCC CTT ACC-3' (antisense). All deletions and point mutations were confirmed by DNA sequencing (DNA Analysis Facility, Department of Molecular Cardiology at The Learner Research Institute, Cleveland Clinic, Cleveland Ohio).

Expression of Wild-Type and Mutant rPro Molecules in Mammalian Cells.

rPro expression in baby hamster kidney (BHK-21) cells has been previously described in detail. Briefly, BHK-21 cells were maintained in Dulbecco's modified Eagle's medium (DMEM) supplemented with fetal bovine serum (10%) and a streptomycin/penicillin (1%) mixture. Isolated plasmids (4-6 μg) for wild-type and mutant rPro molecules were transfected into the BHK-21 cells using a lipid based transfection reagent, lipofectamine (Invitrogen Corp), according to the manufacturer's instructions. Following an incubation period of 48 h, DMEM was supplemented with fetal bovine serum (10%), streptomycin/penicillin (1%) mixture, and methotrexate (1 μM) and added to the cells.

After three weeks of treatment with the selection medium, colonies were isolated, grown, and screened for levels of Pro expression by western blot analysis and compared to plasma-derived Pro as a standard (1 µg/ml). Identification of the highest secreting rPro clone was further used in large-scale protein expression with serum-free Opti-MEM supplemented with $ZnCl_2$ (50 µM), vitamin $K_1$ (10 µg/ml), and penicillin/streptomycin/Fungizone (1% v/v) mixture, and the medium was collected every 2 days for 2-3 weeks. Following collections, the media was stored at −80° C. until the desired amount (usually 4 L) was obtained and used for purification.

Purification of rPro Molecules.

Purification of rPro was performed through a well-established protocol previously described in detail. Briefly, collected media was thawed, filtered (0.45 µm), and loaded on a tandem column setup of amberlite $XAD_2$ and Q-Sepharose. Following the complete addition of medium to the two columns, the Q-Sepharose column was separated and washed with TBS (0.02 M Tris, 150 mM NaCl, pH 7.4). The bound material containing rPro on the Q-Sepharose was eluted with 0.02 M Tris, 0.5 M NaCl, and pH 7.4. The material was treated with barium citrate, and the isolated pellet was dissolved in a minimum volume of EDTA (0.5 M, pH 7.4). The dissolved pellet was dialyzed twice in fresh TBS (2×4 L) and filtered (0.45 m) prior to being loaded onto an General Electric (GE) Fast Performance Liquid Chromatography (FPLC) instrument, equipped with a strong anionic exchanger MonoQ 5/50 column. The column was equilibrated in TBS, and a step-wise gradient of calcium (0-50 mM) in TBS was used to isolate fully gamma-carboxylated rPro. Tubes containing the rPro molecules were concentrated using an appropriate Millipore Centricon (Billerica, Mass.), and aliquots were frozen at −80° C. to avoid repeated freeze-thaw cycles. Following purification and before any experiment, all rPro molecules were characterized as extensively described below.

The level of γ-carboxylation of all rPro molecules was determined following alkaline hydrolysis coupled to amino acid analysis performed at the Texas A&M University protein chemistry facility as described. All purified molecules were found to be properly carboxylated (Table 1). To verify that $rPro^{WT}$ and $rPro^{\Delta 473-487}$ are processed at the appropriate cleavage sites when incubated with prothrombinase or fXa alone and produce the expected fragments, the recombinant proteins were incubated with PCPS vesicles and fXa in the presence and absence of fVa. Following gel electrophoresis, fragments were transferred to PVDF membrane and identified following $NH_2$-terminal sequencing. All fragments deriving from the recombinant prothrombin molecules have the expected $NH_2$-terminal sequence following cleavage by either prothrombinase or membrane-bound fXa alone (not shown).

The fact that the $rPro^{\Delta 473-487}$ molecule contains a fifteen amino acid deletion was verified by cDNA sequencing. However, in view of the surprising and unexpected data presented herein, it was important to confirm the existence of the deletion in the purified recombinant protein. This was accomplished by Mass Spectrometry. Briefly, following activation of rPro and $Pro^{PLASMA}$ by prothrombinase, aliquots were analyzed in triplicated under reducing conditions on a 12% SDS-PAGE. Following staining/destaining, the B-chain of IIa was excised from the gel, and the proteins were reduced and alkylated with iodoacetamide. Digestion (in gel) was accomplished with Porcine Typsin. Analysis of the resulting peptides was performed with an alpha cyano-hydroxycinnamic acid (matrix) Kratos Axima CFR MALDI-TOF mass spectrometer (reflector mode; 25000 accelerating voltage) in the Protein Chemistry Laboratory at Texas A & M University under the direction of Dr. Larry Dangott. The data verified the existence of the deletion in $rPro^{\Delta 473-487}$ Similar experimental work demonstrate that all rPro molecules described herein are fully carboxylated, can be appropriately processed by prothrombinase and fNa alone, and do indeed contain the expected deletion/mutation s.

Gel Electrophoresis and Western Blotting.

Sodium dodecyl sulfate-polyacrylamide gel electrophoresis (SDS-PAGE) was performed according to the method of Laemmli, using 9.5% gels following reduction with 2% β-mercaptoethanol. Screening for high levels of rPro secreting clones was performed by western blotting using polyvinylidene diflouride (PVDF) according to Towbin et al. Successfully transferred proteins were visualized by chemiluminescence using ECL Plus reagents following incubation with a polyclonal antibody specific to prethrombin-1.

Studies of the Pathway for Pro Activation by Gel Electrophoresis.

The investigation of the activation rates of plasma-derived and of all rPro molecules cleavage and activation by fXa alone or prothrombinase was performed according to a protocol described by our laboratory in many instances using plasma-derived Pro or rPro. The calculation of the rates of all Pro molecules consumption by fXa alone or by prothrombinase were performed as previously described with the software Prizm.

Kinetic Titrations of Prothrombinase.

To investigate the kinetic constants ($K_m$ and $k_{cat}$) of prothrombinase, assays with a set amount of plasma-derived fVa and fXa (as described in the legend to the figures) were executed as described by our laboratory in many instances. Each experiment used to report final numbers was run at least in duplicate, and the goodness of fit ($R^2$) for every model tested is provided in the results section. The initial rate of IIa generation was analyzed with the software Prizm (GraphPad), and all final numbers reported are derived directly from the graphs. The change in transition-state stabilization free energy, which measures the effect of the mutations in rPro was calculated for the double and triple mutants as extensively detailed in the literature and repetitively reported by our laboratory.

Recombinant Thrombin Activity.

rPro molecules were converted to rIIa by 1 nM prothrombinase. The chromogenic substrate S-2238 was used to assess rIIa activity by employing serial dilutions in Tris-NaCl buffer in the presence of 0.1% PEG 8000. The final concentrations of S-2238 used in the reactions were 0.94 µM, 1.87 µM, 3.75M, 7.50 µM, 15 µM, and 60 µM. The reaction was started by the addition of 4 nM rIIa. The data was obtained at 1 min using a SpectraMax M2 Platereader (Molecular Devices). The optical density was automatically adjusted for a 1 cm pathlength, and the $V_{max}$ was calculated from the optical density using the established extinction coefficient of S-2238 at room temperature following plotting of the data to the Michaelis-Menten equation using the software Prizm.

Activation of fV and fVIII by rIIa.

rPro molecules were converted to rIIa by 1 nM prothrombinase. The resulting wild-type and mutant IIa were assessed in their ability to cleave and activate the cofactors over time by SDS-PAGE. Reaction mixtures containing either 500 nM plasma derived human fV or recombinant human fVIII were diluted in Tris-NaCl buffer in the presence of $Ca^{2+}$. The final concentration of rIIa in the mixtures was 4 nM.

Activation of protein C by plasma-derived IIa or rIIa. rPro molecules described herein were converted to IIa by 1 nM prothrombinase. The resulting IIa molecules were assessed for their ability to cleave and activate PC in the presence of thrombomodulin and PCPS vesicles according to a procedure previously described in Tris-buffered saline with $Ca^{2+}$. PC activation was verified by SDS-PAGE under reducing conditions. The final concentration of IIa in all mixtures was 8 nM. Gels were stained with Coomassie Brilliant Blue.

Pro Clotting Assay.

To assess the function of all Pro molecules in whole plasma, a clotting assay using Pro-deficient plasma was employed. The clotting assay was performed as previously described, and the time needed for formation of a fibrin clot was monitored at 37° C. using a Diagnostica Stago STart® 4 Hemostasis Analyzer as previously described.

Structural Analysis.

To evaluate the structural features of the $Ser^{478}$, $Leu^{480}$ and $Gln^{481}$ residues, crystal structures of Pro and IIa were superimposed and compared. The three human Pro crystal structures that have been reported show similar conformations for the residues of interest and neighboring regions; the highest resolution of these structures was chosen for detailed analysis. From the many human IIa crystal structures that are available, several representative examples in different bound states were compared and found to have similar conformations for the region containing the residues of interest. A high resolution structure of unbound IIa was chosen as the representative structure for detailed analysis. The program COOT was used to inspect structural features and determine distances. AREAIMOL was used to calculate the solvent-accessible surface areas for specific residues, and molecular figures were prepared with the PyMOL Molecular Graphics System, Version 1.5.0.4 (Schrödinger, LLC).

rPro Expression.

To evaluate the minimal amino acid sequence necessary for the fVa-dependent Pro activation by prothrombinase within the recently identified 473-487 critical amino acid stretch, we stably transfected BHK-21 cell lines according to a previously defined protocol. $rPro^{WT}$ and mutant rPro molecules as follows: $rPro^{\Delta 473487}$ (missing residues $^{473}$GKGQPSVLQVVNLPI$^{487}$), $rPro^{\Delta N10}$ (missing amino acid residues $^{473}$GKGQPSVLQV$^{482}$), and $rPro^{\Delta C10}$ (missing amino acid residues $^{478}$SVLQVVNLPI$^{487}$) (FIG. 1). These three mutant molecules have five amino acids in common ($^{478}$SVLQV$^{482}$). We have thus proceeded to construct, stably express, and purify to homogeneity $rPro^{\Delta 5V}$ (a rPro molecule missing amino acids $^{478}$SVLQV$^{482}$) (FIG. 1). Preliminary experiments with $rPro^{\Delta 5V}$ demonstrated that the mutant molecule had no clotting activity as $rPro^{\Delta 473487}$, $rPro^{\Delta N10}$ and $rPro^{\Delta C10}$. We next proceeded to make single, double and triple alanine substitutions within this significant region. The following recombinant mutant molecules were made: $rPro^{S478A}$ ($Ser^{478} \rightarrow Ala$), $rPro^{L480A}$ ($Leu^{480} \rightarrow Ala$), $rPro^{SL \rightarrow AA}$ ($Ser^{478}/Leu^{480} \rightarrow Ala$), $rPro^{SQ \rightarrow AA}$ ($Ser^{478}/Gln^{481} \rightarrow Ala$) and $rPro^{SLQ \rightarrow AAA}$ ($Ser^{478}/Leu^{480}/Gln^{481} \rightarrow Ala$). It is important to note that $rIIa^{S478A}$ was previously tested and found to behave as $rIIa^{WT}$. We have thus used this mutation as an internal control for all double and triple alanine substitutions of rPro. Finally, and to verify the results obtained with $rPro^{SLQ \rightarrow AAA}$ we have also made a rPro molecule with these three amino acids deleted ($rPro^{\Delta SLQ}$). In all experiments results with the mutant molecules were compared with results obtained with $rPro^{WT}$ or $Pro^{PLASMA}$.

Pro Times.

Figure 2:
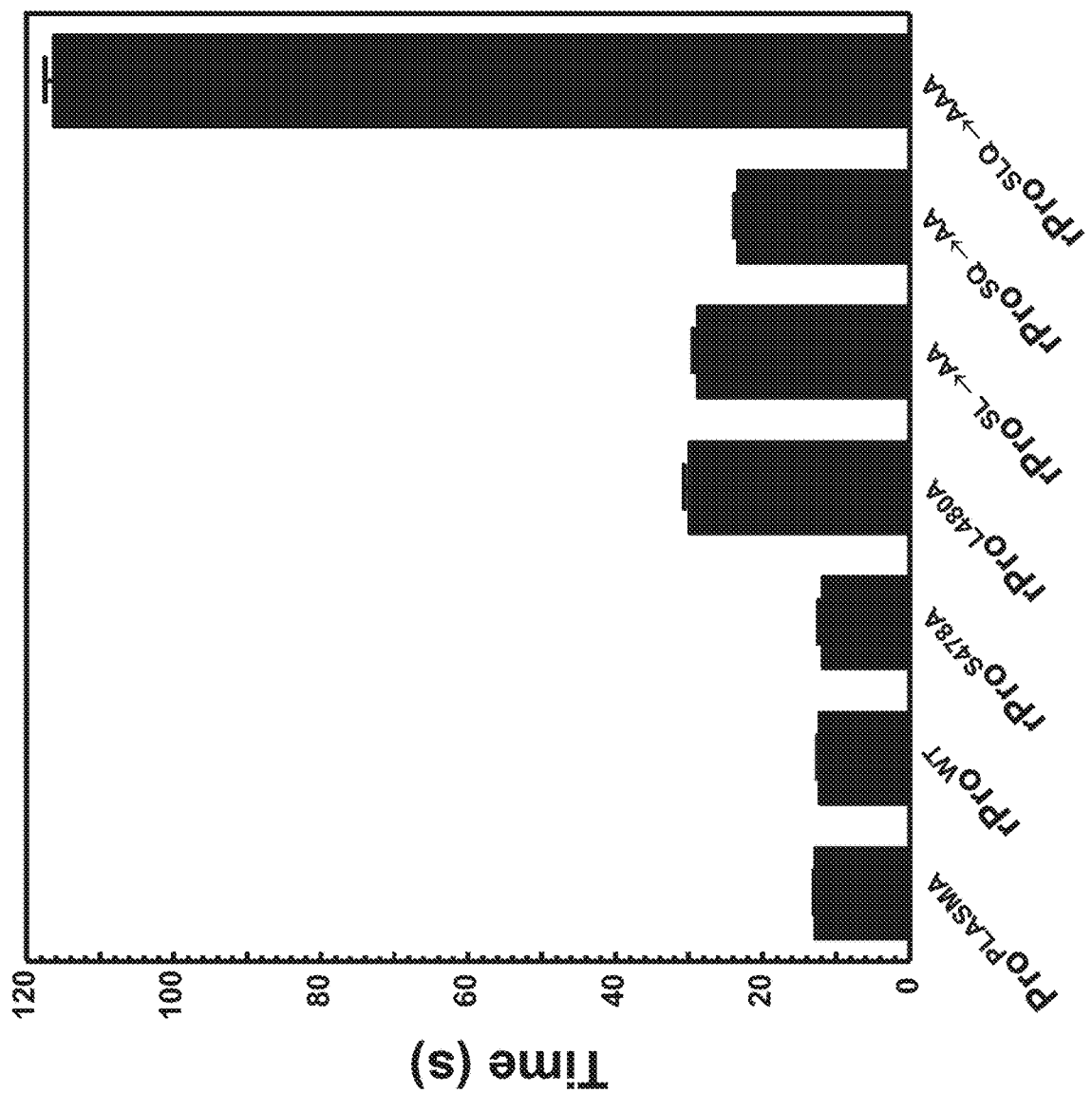
FIG. 2 is a graph of the clotting activity of all forms of Pro. The average clotting time found in four different measurements in Pro-deficient plasma is shown for all Pro/rPro molecules identified at the bottom of the graph.

The ability of all rPro molecules to be activated under physiological conditions and promote fibrin clot formation was first assessed using Pro times (PTs) (FIG. 2).

The physical properties, clotting times, and rate of cleavage of various rPro molecules in the presence of a fixed concentration of membrane-bound fXa or in the presence of prothrombinase are shown in Table 1.

TABLE 1

| Mutant | mol Gla/mol protein | Clotting time$^a$ (s) | Rate of Pro molecules cleavage by membrane-bound fXa alone$^c$ (nM consumed · s$^{-1}$ · fXa$^{-1}$) | Rate of Pro molecules cleavage by prothrombinase$^c$ (nM consumed · s$^{-1}$ · fXa$^{-1}$) |
| --- | --- | --- | --- | --- |
| $Pro^{PLASMA}$ | 10 ± 1 | 12.7 ± 0.12 | 0.13 ± 0.03 (0.94)$^d$ | 17.0 ± 1.9 (0.99)$^d$ |
| $rPro^{WT}$ | 9.1 ± 0.9 | 12.2 ± 0.16 | 0.1 ± 0.012 (0.99) | 22.8 ± 3.8 (0.98) |
| $rPro^{\Delta 473\text{-}487}$ | 9.5 ± 0.1 | >120$^b$ | 0.53 ± 0.013 (0.99) | 1.0 ± 0.26 (0.92) |
| $rPro^{\Delta N10}$ | 12.0 ± 1 | >120$^b$ | 0.7 ± 0.03 (0.98) | 1.5 ± 0.34 (0.94) |
| $rPro^{\Delta C10}$ | 12.5 ± 1 | >120$^b$ | 0.35 ± 0.04 (0.99) | 1.3 ± 0.09 (0.99) |
| $rPro^{\Delta 5V}$ | 11 ± 1 | >120$^b$ | 0.8 ± 0.03 (0.99) | 1.8 ± 0.12 (0.99) |
| $rPro^{S478A}$ | 10.8 ± 1 | 11.75 ± 0.32 | 0.25 ± 0.015 (0.99) | 24.9 ± 4.6 (0.97) |
| $rPro^{L480A}$ | 10.1 ± 1 | 29.8 ± 0.41 | 0.6 ± 0.02 (0.99) | 28.8 ± 2.8 (0.98) |
| $rPro^{SL \rightarrow AA}$ | 9.5 ± 0.9 | 28.7 ± 0.35 | 0.63 ± 0.03 (0.99) | 18.2 ± 3.7 (0.99) |
| $rPro^{SQ \rightarrow AA}$ | 10 ± 1 | 23.2 ± 0.3 | 0.23 ± 0.025 (0.98) | 35.9 ± 3.8 (0.99) |
| $rPro^{SLQ \rightarrow AAA}$ | 10.6 ± 1 | 116.2 ± 0.65 | 0.6 ± 0.04 (0.99) | 1.23 ± 0.12 (0.98) |
| $rPro^{\Delta SLQ}$ | 10.6 ± 1.1 | >120$^b$ | 0.22 ± 0.04 (0.95) | 1.84 ± 0.15 (0.99) |

Figure 4:
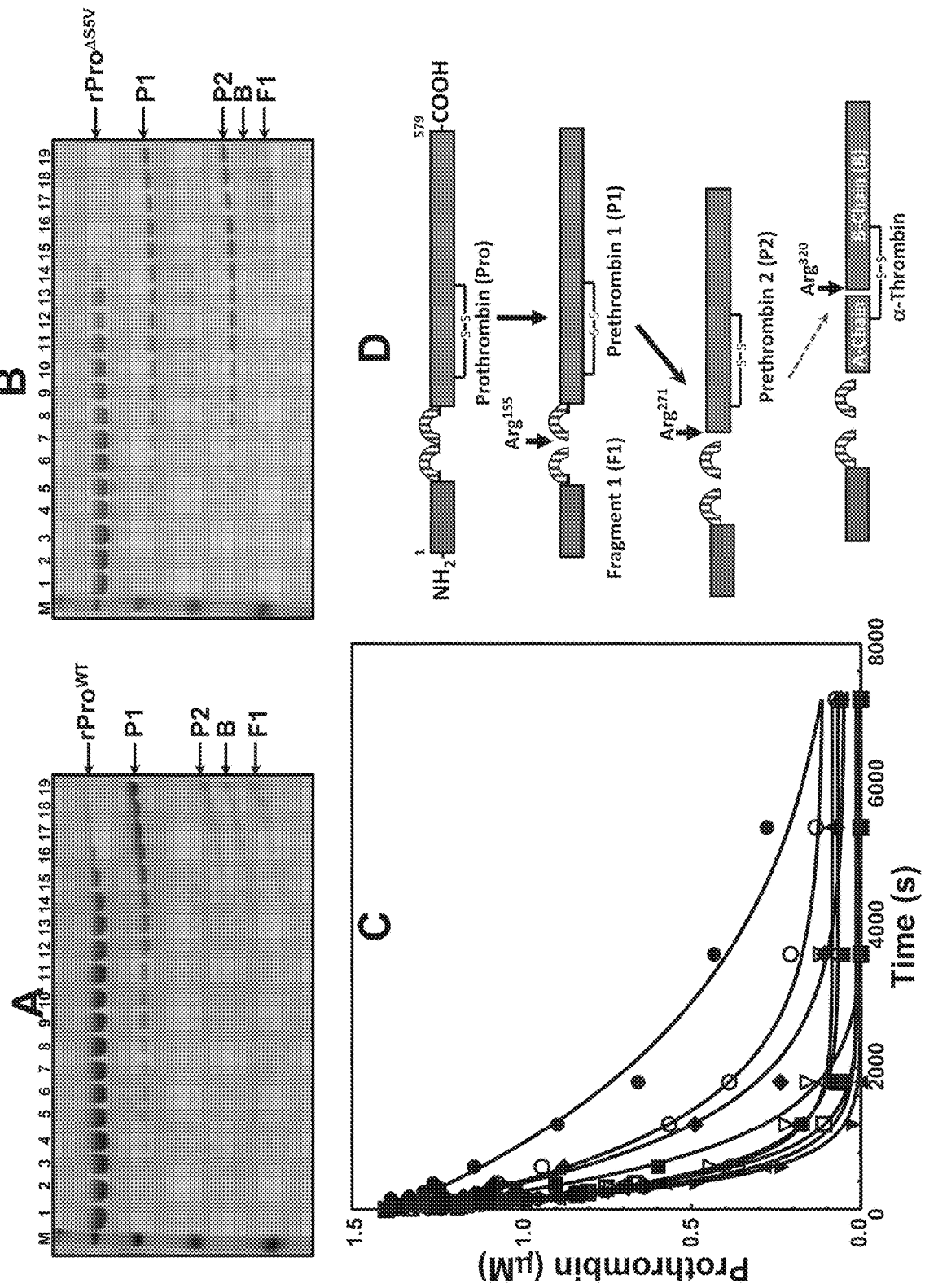
FIG. 4 is an analyses of rPro molecules activation by membrane-bound fXa alone. Panel A: rPro$^{WT}$ (1.4 μM) in the presence of PCPS vesicles, DAPA, and membrane bound fXa alone (5 nM); panel B: rPro$^{\Delta S5V}$ (1.4 μM) in the presence of PCPS vesicles, DAPA, and membrane-bound fXa alone (5 nM). Aliquots were withdrawn at various time intervals and treated as described. M represents the lane with molecular weight markers (from top to bottom): 98000, 64000, 50000, and 36000, respectively. Lanes 1-19 show samples from the reaction mixture before (0 min) the addition of fXa and 20 s, 40 s, 60 s, 80 s, 100 s, 120 s, 150 s, 180 s, 210 s, 240 s, 5 min, 6 min, 10 min, 20 min, 30 min, and 60 min, 90 min, and 120 min respectively, after the addition of fXa. Panel C: the two gels shown in FIGS. 4A and 4B together with similar gels obtained with all rPro studied were scanned and rPro consumption was recorded as described in the Examples section. Following scanning densitometry, and normalization to the initial Pro concentration, the data representing rPro consumption as a function of time (sec) were plotted using non-linear regression analysis according to the equation representing a first-order exponential decay using the software Prizm (GraphPad, San Diego, Calif.). Prothrombinase was assembled with rPro$^{WT}$ (filled circles; R$^2$ 0.98), rPro$^{\Delta C10}$ (filled squares; R$^2$ 0.98), rPro$^{\Delta N10}$ (filled triangles; R$^2$ 0.99), rPro$^{\Delta S5V}$ (filled inverse triangles; R$^2$ 0.99), rPro$^{S478A}$ (filled diamonds; R$^2$ 0.99), rPro$^{L480A}$ (open squares; R$^2$ 0.99), rPro$^{SQ \to AA}$ (open circles; R$^2$ 0.98), rPro$^{SL \to AA}$ (open triangles; R$^2$ 0.99), and rPro$^{SLQ \to AAA}$ (open inverse triangles; R$^2$ 0.99). The rates of rPro consumption shown in panel C, using the apparent first-order rate constant, k (s$^{-1}$) obtained directly from the fitted data, were calculated as reported ( ) and the data is shown in Table 1. Panel D: Schematic representation of fragments derived following Pro activation by membrane-bound fXa alone. The red arrow indicates impaired cleavage at Arg$^{320}$ in rPr$^{\Delta C10}$ (filled squares), rPro$^{\Delta N10}$ (filled triangles), rPro$^{\Delta S5V}$ (filled inverse triangles) and rPro$^{SLQ \to AAA}$ (open inverse triangles) resulting in prethrombin-2 generation. Pro derived fragments are identified to the right of each panel, according to the description provided in the legend of FIG. 3.
Figure 5:
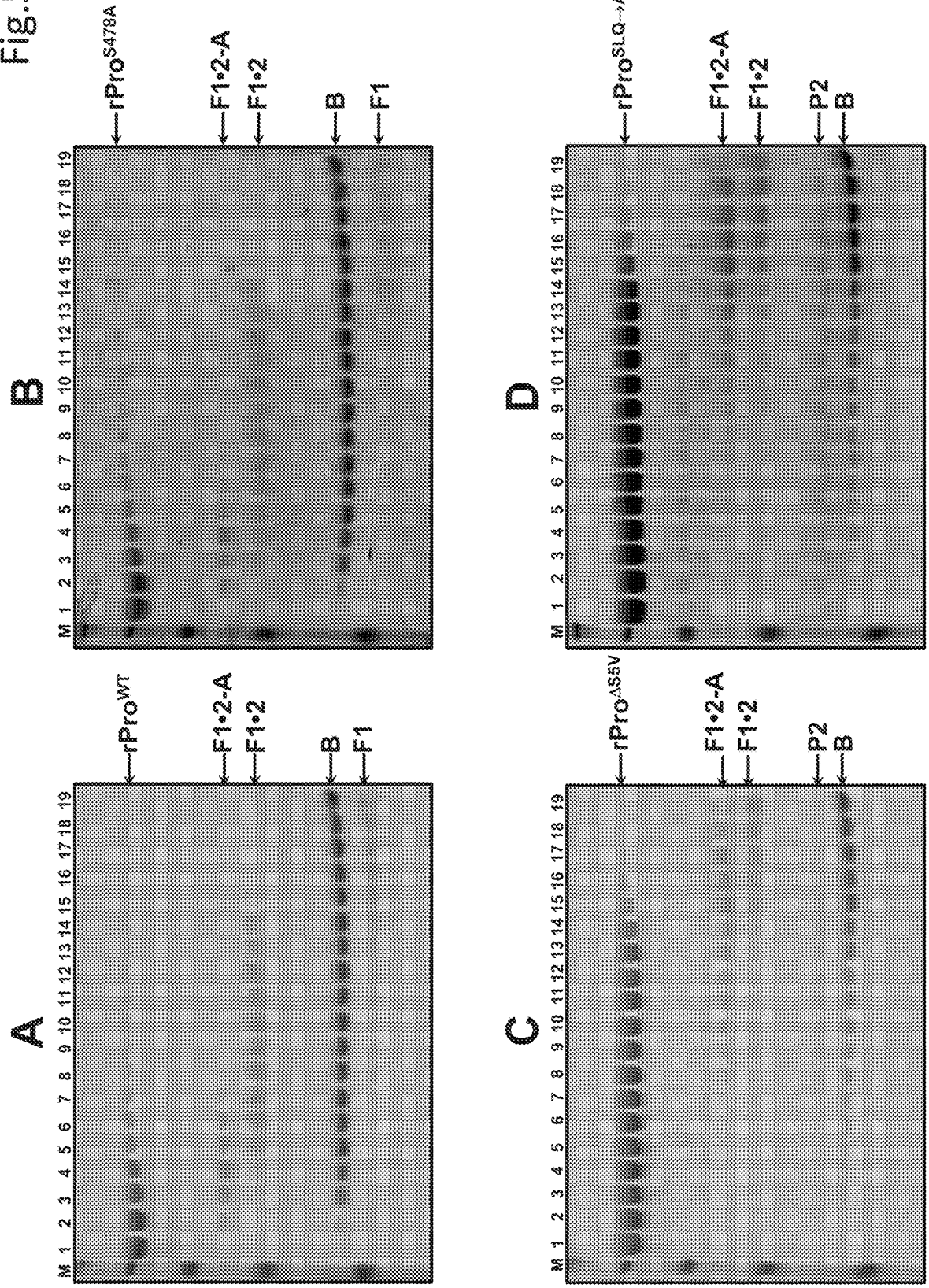
FIG. 5 is an SDS-PAGE analyses of rPro molecules activation by prothrombinase. Panel A: rPro$^{WT}$ (1.4 μM) in the presence of PCPS vesicles, DAPA, and prothrombinase (1 nM fXa and 20 nM fVa); panel B: rPro$^{S478A}$ same conditions as panel in A; panel C: rPro$^{\Delta S5V}$ same conditions as in panel A; panel D: rPro$^{SLQ \to AAA}$ same conditions as in panel A. Aliquots were withdrawn at various time intervals and treated as described. Same time points as described in the legend to FIG. 4. Pro derived fragments are identified to the right of each panel, according to the description provided in the legend of FIG. 3.

$^a$Clotting times were determined using Pro-deficient plasma as described in the Examples in quadruplicate.
$^b$No clotting time could be detected following 120 s incubation time-period.
$^c$The rates of rPro consumption were obtained following scanning densitometry of gels studying rPro activation. Some of the gels used are shown in FIGS. 3, 4, and 5. The final rate of rPro consumption in the presence of membrane-bound fXa or prothrombinase was calculated using the apparent first order rate constant, k (s$^{-1}$), obtained directly from the graph following plotting of the data as described in the Examples section.
$^d$The numbers in parenthesis represent the goodness of fit (R$^2$) to the equation representing first order exponential decay using the software Prizm.

The results shown in Table 1 demonstrate that $rPro^{\Delta 473\text{-}487}$, $rPro^{\Delta N10}$, $rPro^{\Delta C10}$, and $rPro^{\Delta 5V}$ are unable to induce clotting under the conditions described. In contrast, while, $Pro^{PLASMA}$, $rPro^{WT}$ and $rPro^{S478A}$, had comparable clotting times of 12.7 s, 12.2 s and 11.7 s respectively, $rPro^{L480A}$ exhibited a minimal but significant prolonged PT of ~30 s (FIG. 2). Surprisingly, while $rPro^{SL \rightarrow AA}$ and $rPro^{SQ \rightarrow AA}$ had slow but comparable PTs of ~30 s, the triple mutant $rPro^{SLQ \rightarrow AAA}$ was severely ineffective in fibrin clot formation (PT ~116 s) while $rPro^{\Delta SLQ}$ had a PT around 140 s (not shown). In contrast, $rPro^{\Delta 473\text{-}487}$, $rPro^{\Delta N10}$ rPro, rPro$^{\Delta C10}$, and rPro$^{\Delta S5V}$ are unable to induce clotting under the conditions described. These functional data demonstrate that either rPro$^{SLQ \rightarrow AAA}$ cannot get activated to rIIa in a timely fashion, or that rIIa$^{SLQ \rightarrow AAA}$ formed is catalytically impaired because of the mutation, or both. Since previous data has shown that the Ser$^{478} \rightarrow$Ala transition in IIa is of no consequence for its chromogenic and proteolytic activity, overall these results demonstrate for the first time that both Leu$^{480}$ and Gln$^{481}$ have a profound effect on IIa generation and/or IIa activity during fibrin clot formation or both.

The Activation of rPro Molecules.

To ascertain the effect of region 473-487 of prothrombin on its ability to be activated by membrane bound fXa alone, in the absence of fVa, we assessed the pattern of activation by gel electrophoresis over a 2 h time-period (FIG. 3). Panel 3A, shows a control experiment and demonstrates that Pro$^{PLASMA}$ activation by membrane-bound fXa proceeds following initial cleavage at Arg$^{271}$, through the intermediate prethrombin-2 with very slow gradual appearance of the B chain of IIa because of inefficient rate of cleavage at Arg$^{320}$. Astonishingly, with the removal of amino acids 473-487 from prothrombin (FIG. 3B), there is acceleration of rPro$^{\Delta 473-487}$ consumption through initial cleavage at Arg$^{271}$ that is evident by the prompt appearance of prethrombin-2. Additional examinations of the intensity of the B-chain of thrombin reveal a substantially delayed cleavage at Arg$^{320}$ of the recombinant deletion mutant prothrombin molecule, compared with rPro$^{WT}$ resulting in insignificant IIa generation. Scanning densitometry of the gels shown in FIGS. 3A and 3B showed that the rate of rPro$^{\Delta 473-487}$ consumption by membrane-bound fXa is approximately 4-fold increase compared to the rate of cleavage of rPro$^{PLASMA}$ under similar experimental conditions (Table 1). These data reveal that amino acid sequence 473-487 of prothrombin provides a potential obstruction for efficient initial cleavage of prothrombin at Arg$^{271}$ by membrane-bound fXa alone in the absence of fVa.

To improve our understanding of the fundamental role of amino acid region 473-487 for Pro activation by prothrombinase, we studied the pattern of Pro activation by fully assembled prothrombinase by gel electrophoresis over a 2 h time-period. A control experiment (FIG. 3C) demonstrates that, under the conditions used, Pro$^{PLASMA}$ proceeds, following initial cleavage at Arg$^{320}$, through the enzymatically active intermediate meizothrombin, as confirmed by the appearance of fragment 1•2-A. Rapid cleavage of this fragment at Arg$^{271}$ leads to the formation of IIa. In contrast, activation of rPro$^{\Delta 473-487}$ under similar experimental conditions is significantly delayed through the same pathway as verified by the late appearance of the B chain of IIa (FIG. 3D). Scanning densitometry of the gels shown in FIGS. 3C and 3D showed that rPro$^{\Delta 473-487}$ is consumed with a rate that is ~27-fold slower compared to the rate of rPro$^{PLASMA}$ consumption under the experimental conditions used (Table 1). These data suggest that under conditions of saturating amounts of fVa with respect to fXa, amino acid sequence 473-487 of Pro plays a preeminent role because it is required for fast and efficient initial cleavage of Pro at Arg$^{320}$ by prothrombinase.

To further investigate the effect of the deletions and point mutations on rPro cleavage and activation by membrane-bound fXa alone, we studied rPro activation by gel electrophoresis of all mutants detailed in FIG. 1. Panel 4A shows a control experiment and demonstrates that rPro$^{WT}$ activation by membrane-bound fXa proceeds typically following initial cleavage at Arg$^{271}$, as its plasma counterpart through the intermediate prethrombin-2 with very slow and minimal appearance of the B chain of IIa because of unproductive rate of cleavage at Arg$^{320}$. With the removal of amino acids 478-482 from rPro$^{\Delta S5V}$ (FIG. 4B), there is acceleration of rPro$^{\Delta 478-482}$ consumption by fXa alone through initial cleavage at Arg$^{271}$ that is evident by the rapid appearance of prethrombin-2. The fact that no trace of B-chain of IIa is apparent under the conditions employed, suggests a substantially deferred rate of cleavage at Arg$^{320}$ of the deletion mutant compared with cleavage of rPro$^{WT}$ resulting in insignificant amounts of IIa generation. Scanning densitometry of similar gels shown in FIGS. 4A and 4B showed that the rate of consumption of all rPro molecules by membrane-bound fXa alone is approximately 2.3-8-fold increased compared to the rate of cleavage of rPro$^{WT}$ (FIG. 4C, Table 1). However, while with rPro$^{S478}$, rPro$^{L480A}$, rPro$^{SL \rightarrow AA}$, and rPro$^{SQ \rightarrow AA}$ minimal amounts of the B-chain of IIa are formed (not shown), when studying rPro$^{\Delta N10}$, rPro$^{\Delta C10}$, rPro$^{\Delta S5V}$, and rPro$^{SLQ \rightarrow AAA}$ activation, there is accumulation of prethrombin-2 with no significant amounts of B chain of IIa generated (FIG. 4B). These data confirm our findings with rPro$^{\Delta 473-487}$ (FIG. 3) and reveal that the dipeptide Leu$^{480}$-Gln$^{481}$ within the fifteen amino acid stretch 473-487 of Pro appear to be responsible for the similar effects observed with rPro$^{\Delta N10}$, rPro$^{\Delta C10}$, rPro$^{\Delta S5V}$, rPro$^{SLQ \rightarrow AAA}$ and rPro$^{\Delta SLQ}$ when studying rPro molecules activation by membrane-bound fXa alone in the absence of fVa (FIG. 4D and Table 1).

Figure 6:
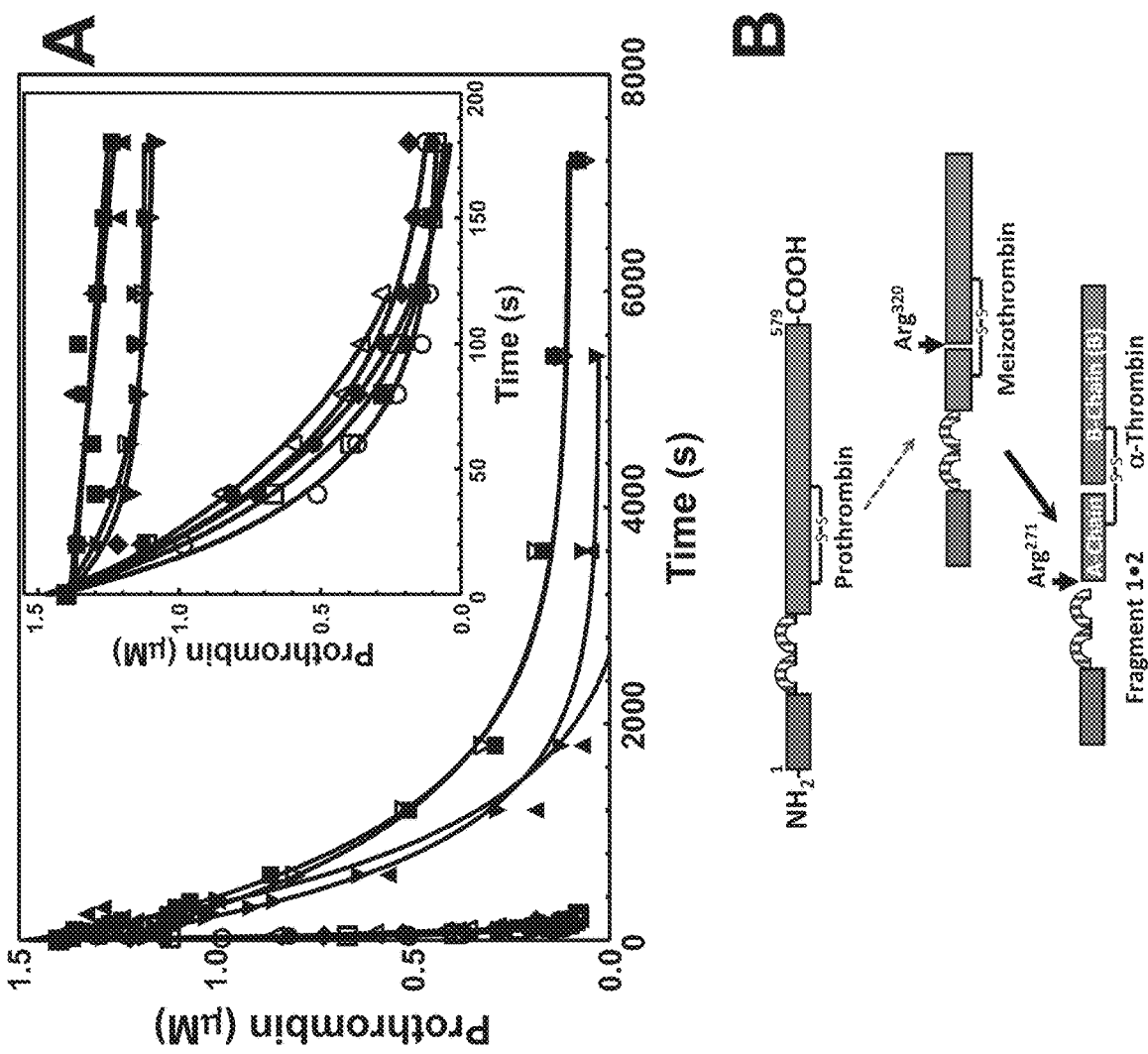
FIG. 6 is an analyses of the rates of activation of rPro by prothrombinase. Panel A: the gels shown in FIG. 4 together with similar gels obtained with all rPro studied, were scanned and rPro consumption was recorded as described in the Examples section. Following scanning densitometry, the numbers were normalized to the initial concentration of rPro studied, and the data representing rPro consumption as a function of time (sec) were plotted using non-linear regression analysis according to the equation representing a first-order exponential decay using the software Prizm (GraphPad, San Diego, Calif.). rPro$^{WT}$ (filled circles; R$^2$ 0.98), rPro$^{\Delta C10}$ (filled squares; R$^2$ 0.99), rPro$^{\Delta N10}$ (filled triangles; R$^2$ 0.94), rPro$^{\Delta S5V}$ (filled inverse triangles; R$^2$ 0.99), rPro$^{S478A}$ (filled diamonds; R$^2$ 0.97), rPro$^{L480A}$ (open squares; R$^2$ 0.98), rPro$^{SQ \to AA}$ (open circles; R$^2$ 0.99), rPro$^{SL \to AA}$ (open triangles; R$^2$ 0.99), and rPro$^{SLQ \to AAA}$ (open inverse triangles; R$^2$ 0.99). The inset shows the progress of the reaction during the first 180 s. The rates of rPro consumption using the apparent first-order rate constant, k (s$^{-1}$) obtained directly from the fitted data, were calculated as reported and shown in Table 1. Panel B: Schematic representation of fragments derived following rPro activation by prothrombinase in the presence of an excess fVa with respect to fXa. The red arrow indicates impaired cleavage (at Arg$^{320}$) in rPr$^{\Delta C10}$ (filled squares), rPro$^{\Delta N10}$ (filled triangles), rPro$^{\Delta S5V}$ (filled inverse triangles) and rPro$^{SLQ \to AAA}$ (open inverse triangles).

To improve our fundamental understanding of the essential role of amino acids Leu$^{480}$ and Gln$^{481}$ for Pro activation, we studied the pattern of all rPro molecules activation shown in FIG. 1 by fully assembled prothrombinase (i.e. in the presence of an excess of fVa) by gel electrophoresis over a 2 h time-period (FIG. 5). A control experiment (FIG. 5, panel A) demonstrates that under the conditions used rPro$^{WT}$ proceeds as its plasma counterpart following initial cleavage at Arg$^{320}$, through the enzymatically active intermediate meizothrombin, as confirmed by the appearance of fragment 12-A. Rapid cleavage of this fragment at Arg$^{271}$ leads to the formation of rIIa. Similar results were found when using rPro$^{S478A}$ (FIG. 5B) demonstrating that the Ser$^{478} \rightarrow$Ala transition alone is of no consequence for timely Pro activation by prothrombinase. In contrast, activation of rPro$^{\Delta S5V}$ and rPro$^{SLQ \rightarrow AAA}$ under similar experimental conditions was significantly delayed through the same pathway as verified by the lingering of fragment 1•2-A at the late time points and the late appearance of the B chain of rIIa (FIG. 5, panels C and D). Similar results were obtained with rPro$^{\Delta SLQ}$ (Table 1). A systematic analysis of the activation of all rPro mutant molecules by prothrombinase using similar experimental procedures, followed by scanning densitometry of the gels and calculation of the rate of rPro consumption, revealed the existence of two groups: a group of molecules represented by Pro$^{PLASMA}$, rPro$^{WT}$ and rPro$^{S478A}$ (also containing rPro$^{L480A}$, rPro$^{SL \rightarrow AA}$, and rPro$^{SQ \rightarrow AA}$) that are efficiently activated by prothrombinase, and a second group of proteins represented by rPro$^{\Delta S5V}$ and rPro$^{SLQ \rightarrow AAA}$ (including rPro$^{\Delta N10}$, rPro$^{\Delta C10}$, and rPro$^{\Delta SLQ}$) that are activated by fully assembled prothrombinase with a rate that is 13-17-fold slower than for the first group (FIG. 6A, inset and Table 1). The data suggest that under conditions of saturating amounts of fVa with respect to fXa, the dipeptide Leu$^{480}$-Gln$^{481}$ of prothrombin play a leading role during Pro activation because they are required for fast and efficient initial cleavage at Arg$^{320}$ by prothrombinase (FIG. 6B, the deficient step is represented by the red arrow). It is quite remarkable that similar experiments analyzing the activation of rPro$^{\Delta SLQ}$ by fully assembled prothrombinase performed with different reagents (fXa and PCPS vesicles) and several months apart, produced almost identical rates of activation as the rate obtained for the activation of rPro$^{\Delta S5V}$ (Table 1), attesting of the validity of our results and of the crucial role of amino acids Leu$^{480}$-Gln$^{481}$ for efficient rPro activation by prothrombinase.

Kinetic Analyses of rPro Molecules Activation.

Figure 7:
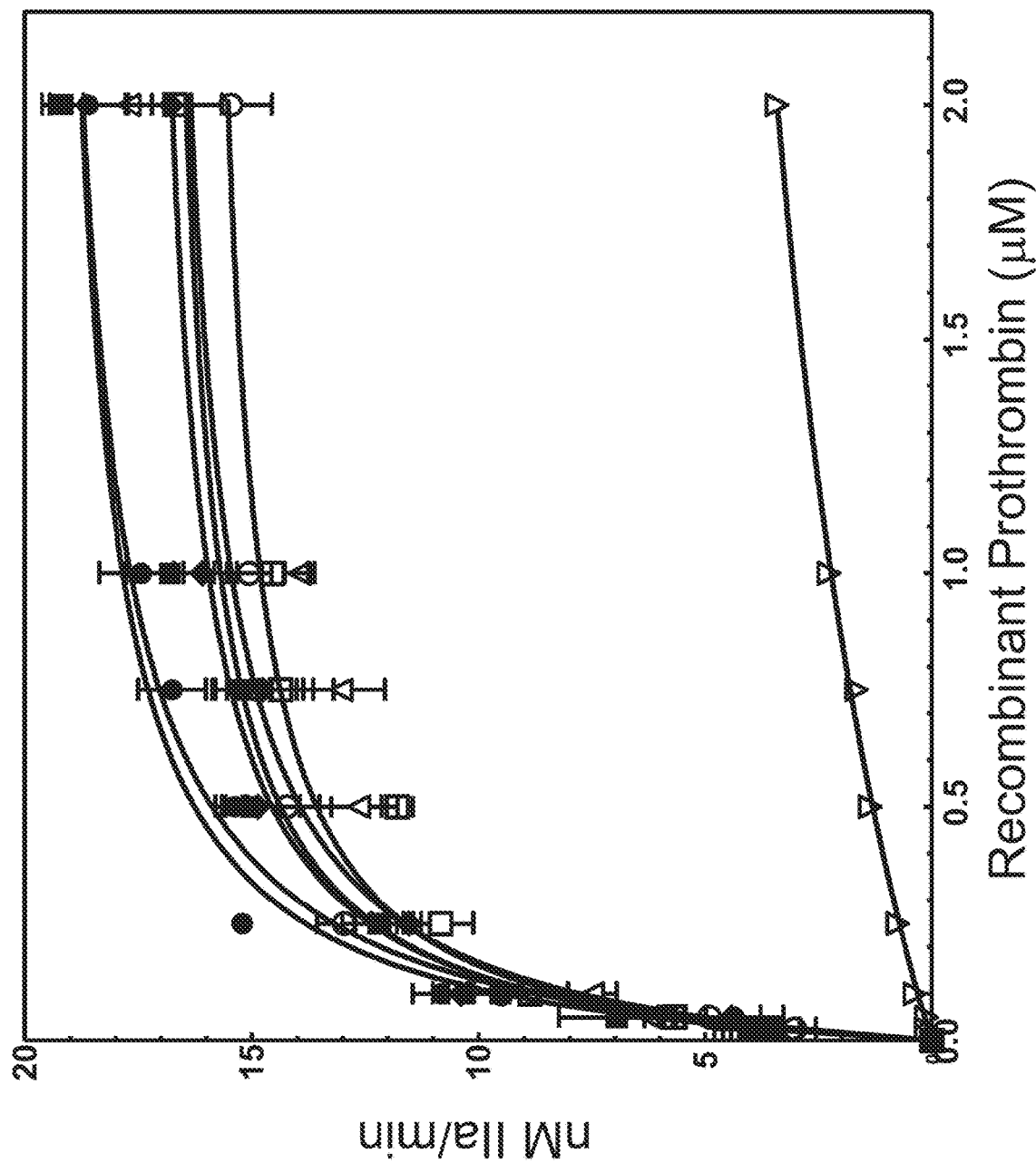
FIG. 7 is a determination of kinetic parameters of prothrombinase catalyzing cleavage and activation of various Pro molecules. IIa generation experiments were conducted as described in the Examples by varying the substrate concentration and using a chromogenic substrate. The solid lines represent the nonlinear regression fit of the data using Prizm GraphPad software according to the Henri Michaelis-Menten equation (V$_o$=V$_{max}$·[Pro]/K$_m$+[Pro]) to yield the K$_m$ and k$_{cat}$ (k$_{cat}$=V$_{max}$/E$_{TOT}$, where E$_{TOT}$ is the concentration of fully assembled prothrombinase, in this case is 10 pM, Table 2). Prothrombinase activity with various rPro molecules is shown as follows: rPro$^{WT}$ filled circles; Pro$^{PLASMA}$ filled squares; rPro$^{S478A}$ filled diamonds; rPro$^{L480A}$ open squares; rPro$^{SL \to AA}$ open triangles; rPro$^{SQ \to AA}$ open circles; rPro$^{SLQ \to AAA}$ open inverse triangles. Kinetic constants reported in the text and in Table 2 were extracted directly from fitted data showed herein.

In order to understand the effect of the Ser$^{478}$/Leu$^{480}$/Gln$^{481}$→A substitutions on the activity of prothrombinase in activating the rPro molecules, we first examined the rates of rIIa formation from all rPro molecules under similar experiment conditions. Historically, this method was designed to identify any deficiency in fVa or fXa as part of prothrombinase in cleaving and activating Pro and is measured indirectly by using IIa generation as a reporting probe with a chromogenic substrate. The comprehensive kinetic data for several mutants are shown in FIG. 7 with the kinetic constants derived directly from the fitted data reported in Table 2.

Kinetic constants of plasma Pro and various rPro mutant molecules activation by prothrombinase are shown in Table 2.

To quantify the interaction between the two sets of double mutations (Ser$^{478}$/Leu$^{480}$→A and Ser$^{478}$/Gln$^{481}$→A) and to confirm their apparent synergistic detrimental effect on prothrombinase function for activation of rPro$^{SLQ \to AAA}$, we have further calculated the difference in free energy of the transition state analog ($\Delta\Delta G_{int}$) for the triple mutant as previously and punctiliously described by our laboratory. The large positive value of $\Delta\Delta G_{int}$ (+2.4 kcal/mol) for the combination of the mutations at Leu$^{480}$ and Gln$^{481}$ together with the sizeable 55-fold decrease in the second order rate constant of prothrombinase for rPro$^{SLQ \to AAA}$ activation, signify that there is a deficiency in recognition between prothrombinase and rPro$^{SLQ \to AAA}$. These findings solidify our previous conclusion that these substitutions are detrimental to the activation of rPro bearing the triple amino acid substitution by fully assembled prothrombinase. However, it is important to note that it is also possible that rIIa$^{SLQ \to AAA}$ may also be deficient in its own catalytic activity as observed with rIIa$^{\Delta SLQ}$, and the effect seen with rPro$^{SLQ \to AAA}$ activation may be likewise due to the deficiency of rIIa in cleaving the chromogenic substrate. Thus, while we cannot yet assign the poor performance of prothrombinase in cleaving

TABLE 2

| Prothrombin species | $K_m^b$ (μM) | $k_{cat}^{b,d}$ (min$^{-1}$) | $R^2$/points/titrations$^e$ | $k_{cat}/K_m$ (M$^{-1}$·s$^{-1}$)· $10^8$ | Decrease$^f$ (−fold) |
|---|---|---|---|---|---|
| Pro$^{PLASMA}$ | 0.13 ± 0.02 | 1992 ± 68 | 0.93/30/3 | 2.5 | — |
| rPro$^{WT}$ | 0.11 ± 0.015 | 1976 ± 57 | 0.97/20/2 | 2.9 | — |
| $^a$rPro$^{WT}$ | 0.11 ± 0.02 | 2054 ± 84 | 0.97/10/1 | 3.1 | — |
| rPro$^{\Delta 473\text{-}487}$ | np$^c$ | — | — | — | — |
| rPro$^{\Delta N10}$ | np | — | — | — | — |
| rPro$^{\Delta C10}$ | np | — | — | — | — |
| rPro$^{\Delta S5V}$ | np | — | — | — | — |
| rPro$^{S478A}$ | 0.10 ± 0.013 | 1764 ± 45 | 0.97/20/2 | 2.9 | 1.0 |
| rPro$^{L480A}$ | 0.10 ± 0.015 | 1630 ± 49 | 0.96/20/2 | 2.7 | 1.1 |
| rPro$^{SL \to AA}$ | 0.12 ± 0.02 | 1734 ± 65 | 0.92/30/3 | 2.4 | 1.2 |
| rPro$^{SQ \to AA}$ | 0.10 ± 0.015 | 1727 ± 52 | 0.94/30/3 | 2.9 | 1.0 |
| rPro$^{SLQ \to AAA}$ | 2.3 ± 0.5 | 730 ± 101 | 0.96/36/4 | 0.053 | 55 |
| $^a$rPro$^{\Delta SLQ}$ | 3.2 ± 1.5 | 128 ± 34 | 0.96/9/1 | 0.0067 | 463 |

$^a$Experiments with these two preparations of recombinant molecules were performed in parallel with same reagents (fXa and PCPS vesicles). The results shown are representative of four separate titrations with three different preparations of rPro$^{\Delta SLQ}$ compared to either rPro$^{WT}$ or Pro$^{PLASMA}$.
$^b$The $K_m$ and $k_{cat}$ of prothrombinase assembled with saturating concentrations of recombinant fVa molecules were determined as described in the Examples section according to the Michaelis-Menten equation using the software Prizm from several different preparations of rPro molecules (representative experiments are shown in FIG. 7). Kinetic constants were derived directly from the fitted data.
$^c$ no plot; data could not be plotted to the Michaelis-Menten equation using the software Prizm. in the assay studying prothrombin activation using a chromogenic substrate.
$^d k_{cat} = V_{max}/[\text{enzyme}]$; the enzyme concentrations of prothrombinase (fXa-fVa complex on the membrane surface in the presence of Ca$^{2+}$) under the conditions employed herein was 10 pM.
$^e R^2$ is the goodness of fit of the data points to the Michaelis-Menten equation using the software Prizm. Points and titrations studied represent 10 measurements/graph for all experiments (up to 4 μM plasma-derived Pro or rPro molecules) except experiments with rPro$^{SLQ \to AAA}$ (9 measurements/graph, up to 2 μM prothrombin) and with rPro$^{\Delta SLQ}$ (9 measurements/graph, up to 4 μM prothrombin).
$^f$The −fold decrease is the ratio of the second order rate constant ($k_{cat}/K_m$) of prothrombinase catalyzing rPro$^{WT}$ activation compared to the second order rate constant of prothrombinase catalyzing activation of all other rPro molecules.

The combined findings demonstrate that, while the single and double alanine substitutions Pro mutants are activated by prothrombinase similarly providing comparable kinetic constants as the wild type or plasma Pro molecules surprisingly, kinetic analyses of prothrombinase activation of rPro$^{SLQ \to AAA}$ demonstrate a modest 2.7-fold decrease in the $k_{cat}$ with a concomitant and very significant 21-increase in the $K_m$ of the reaction. Similar experiments studying rPro$^{\Delta SLQ}$ activation by fully assembled prothrombinase revealed a 29-fold increase in $K_m$ with a concomitant 16-fold decrease in the $k_{cat}$ of the reaction. A direct comparison between the data obtained with rPro$^{SLQ \to AAA}$ with the data obtained with rPro$^{\Delta SLQ}$ strongly suggest an important contribution of the backbone structure of the peptide bond between these three amino acids to efficient rPro activation by prothrombinase.

rPro$^{SLQ \to AAA}$ solely to a deficiency in recognizing the mutated substrate, and since the Ser$^{478}$→Ala transition is of no consequence for either rPro$^{S478A}$ activation or rIIa$^{S478A}$ activity, the overall data presented thus far suggest that amino acid sequence Leu$^{480}$-Gln$^{481}$ may have a dual effect in providing a prothrombinase recognition site as well as for an exosite for the resulting enzyme required for proper substrate tethering and cleavage. However, it is also possible that these two amino acids are allosterically involved in both prothrombinase interacting with Pro as well as the expression of the enzymatic activity of IIa.

Analyses of the Activity of rIIa Molecules.

While previous investigations have identified the specific amino acid residues from Pro/IIa participating in either prothrombinase recognition or IIa activity towards its physiological substrates respectively, few studies have shown that identical residues are involved in both Pro recognition by prothrombinase and IIa activity. In order to understand the effect of the deletions/mutations on IIa activity, we further assessed the esterase and biological activity of all rIIa molecules generated herein towards the chromogenic substrate S-2238 and thrombin's natural substrates, fV, fVIII, and PC.

To understand the effect of the mutations on the esterase activity of IIa, we determined the kinetic constants for the hydrolysis of S-2238 by the rIIa molecules under steady state conditions. The data shown in Table 3 reveal that: 1) rIIa$^{WT}$ produced under the conditions described by our laboratory has similar activity as previously found with other recombinant rIIa$^{WT}$ preparations, and 2) rIIa$^{S478A}$ has similar catalytic efficiency ($k_{cat}/K_m$) as rIIa$^{WT}$ as previously demonstrated. In addition, we also found that while rIIa$^{SLQ \rightarrow AAA}$ was devoid of activity towards S-2238, rIIa$^{SQ \rightarrow AA}$ has similar esterase activity as rIIa$^{WT}$, whereas rIIa$^{L480A}$ and rIIa$^{SL \rightarrow AA}$ are the most deficient in S-2238 hydrolysis among the single and double alanine mutants when compared to rIIa$^{WT}$ or to rIIa$^{S478A}$ (Table 3). The combined data clearly demonstrates that amino acid Leu$^{481}$ plays an important role during the expression of IIa chromogenic activity and that the integrity of amino acid sequence Glu$^{480}$-Leu$^{481}$ is required for optimum expression of the esterase activity rIIa.

TABLE 3

| α-Thrombin species | $K_m^a$ (μM) | $k_{cat}^c$ (s$^{-1}$) | $R^{2d}$ | $k_{cat}/K_m$ (M$^{-1}$·s$^{-1}$)·10$^6$ |
|---|---|---|---|---|
| rIIa$^{WT}$ | 47 ± 1.8 | 22.7 ± 2.7 | 0.93 | 4.8 |
| rIIa$^{S478A}$ | 8.5 ± 1.5 | 36.5 ± 2.4 | 0.98 | 4.3 |
| rIIa$^{L480A}$ | 8.9 ± 1.7 | 15.5 ± 1.5 | 0.98 | 1.7 |
| rIIa$^{SL \rightarrow AA}$ | 7.7 ± 3.0 | 14.7 ± 2.0 | 0.92 | 1.9 |
| rIIa$^{SQ \rightarrow AA}$ | 10.8 ± 4.2 | 33.1 ± 4.9 | 0.93 | 3.0 |
| rIIa$^{SLQ \rightarrow AAA}$ | np$^b$ | np | np | — |

$^a$The $K_m$ of rIIa molecules for S-2238 was determined as described in the Examples section according to the Michaelis-Menten equation using the software Prizm. Kinetic constants shown were derived directly from the fitted data.
$^b$no data could be plotted.
$^c k_{cat} = V_{max}$/[enzyme]; the Vmax was calculated as described in the Examples section and the enzyme concentrations of rIIa was 4 nM for all experiments shown.
$^d R^2$ is the goodness of fit of the data points to the Michaelis-Menten equation using the software Prizm.

Figure 8:
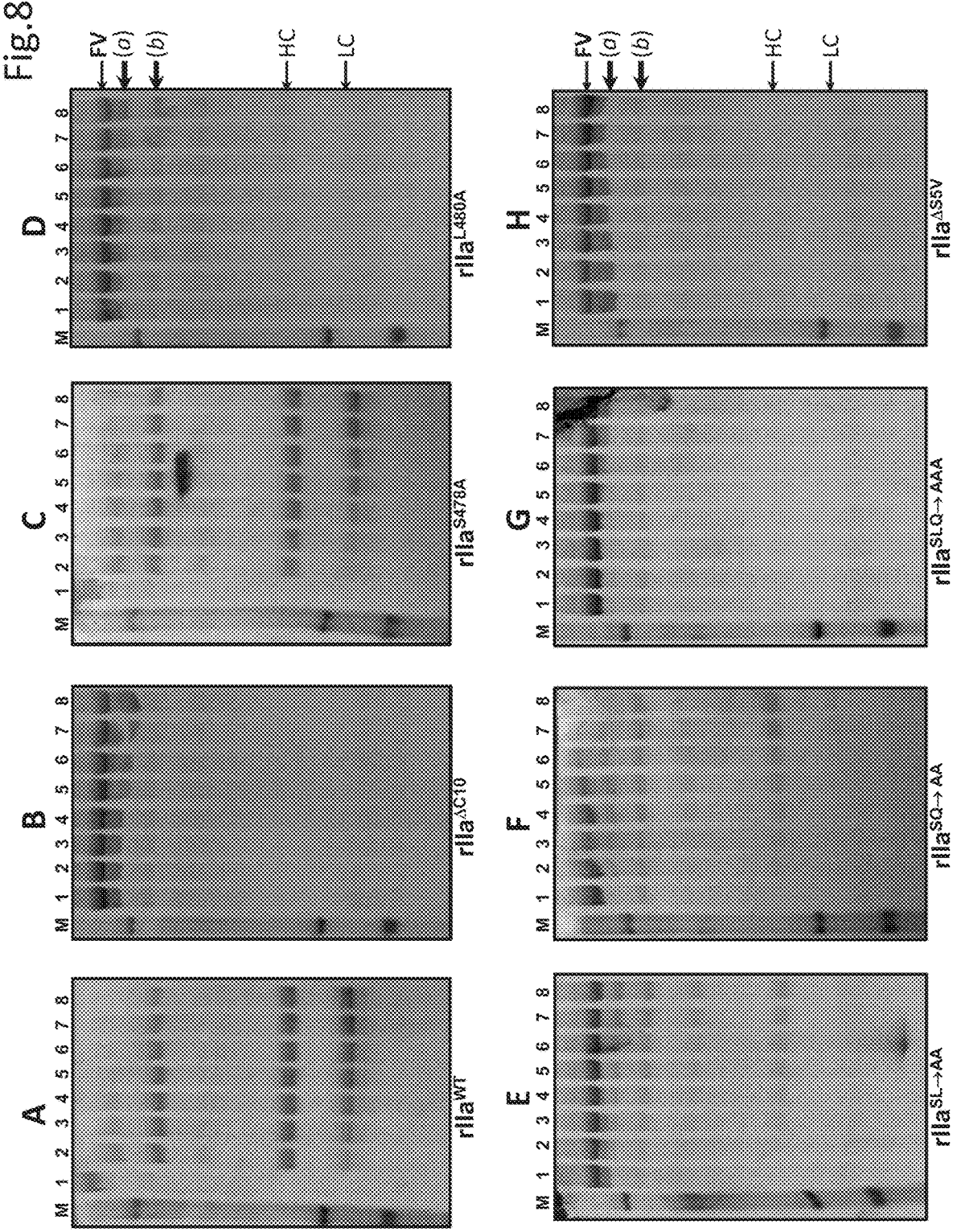
FIG. 8 shows the activation of plasma-derived fV by rIIa. Plasma-derived fV (500 nM) was incubated with rIIa (4 nM) as described in the Examples. At selected time intervals, aliquots of the mixtures were removed, mixed with 2% SDS, heated for 5 min at 90° C., and analyzed on a 4-12% SDS-PAGE followed by staining with Coomassie Blue. Lane 1 in all panels depicts aliquots of the mixture withdrawn from the reaction before the addition of the isolated rIIa. Lanes 2-8 represent aliquots of the reaction mixture withdrawn at 10 min, 20 min, 30 min, 45 min, 60 min, 120 min, and 180 min. The positions of all fV fragments are indicated at the right of panels D and H. Fragments (a) and (b) of fV are identified as previously shown.
Figure 9:
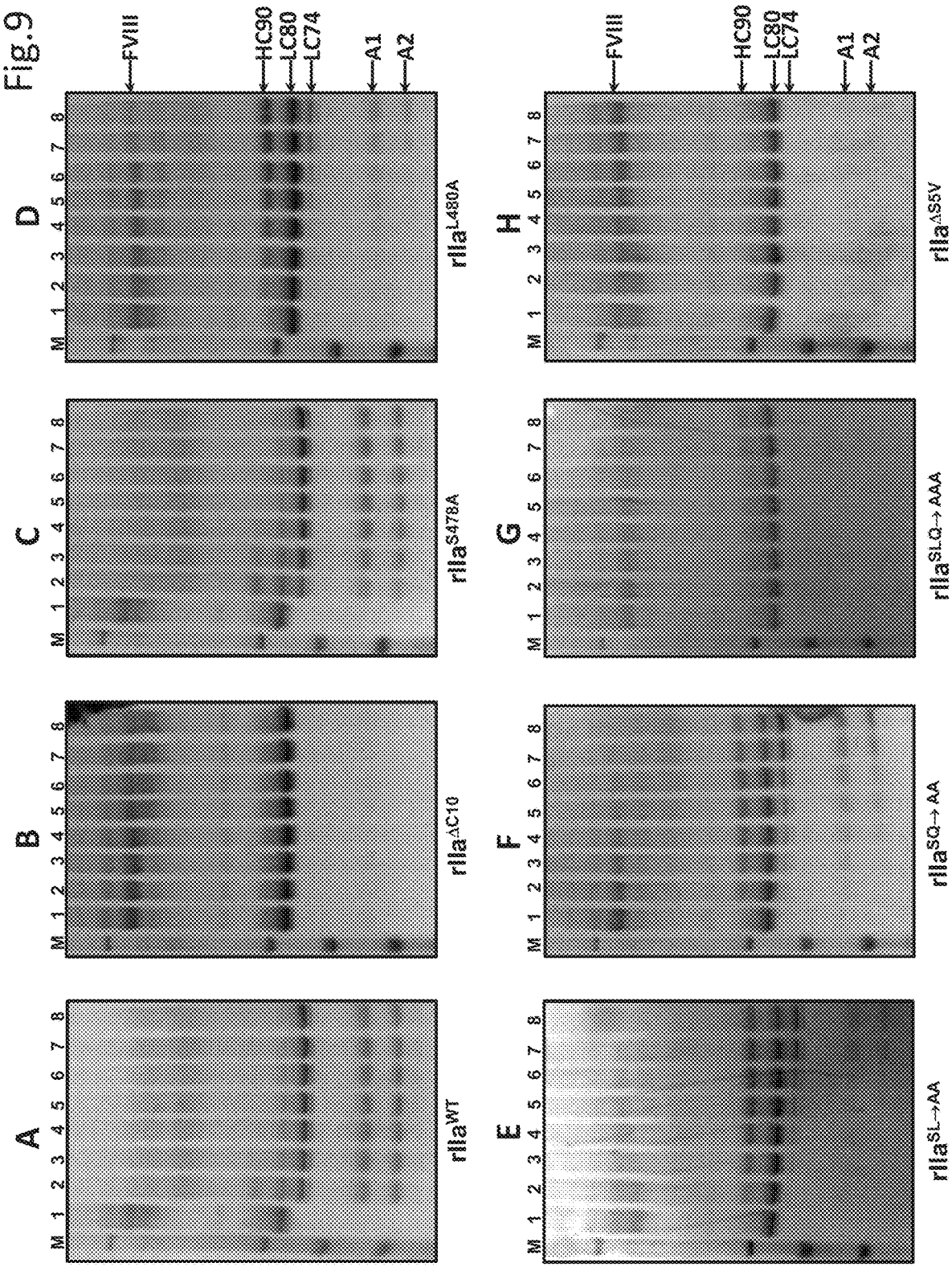
FIG. 9 shows the activation of recombinant fVIII by rIIa. rfVIII (500 nM) was incubated with rIIa (4 nM) as described below. At selected time intervals, aliquots of the mixtures were removed, mixed with 2% SDS, heated for 5 min at 90° C., and analyzed on a 4-12% SDS-PAGE followed by staining with Coomassie Blue. Lane 1 in all panels depicts aliquots of the mixture withdrawn from the reaction before the addition of the isolated rIIa. Lanes 2-8 represent aliquots of the reaction mixture withdrawn at 10 min, 20 min, 30 min, 45 min, 60 min, 120 min, and 180 min. The positions of all rfVIII fragments are indicated at the right of panels D and H. Fragments from rfVIII are identified as previously shown.

The data shown in FIGS. 8 and 9 demonstrate that while rIIa$^{WT}$ and rIIa$^{S478A}$ cleave and activate both cofactors with similar rates (FIGS. 8A, 8C, 9A, and 9C), rIIa$^{\Delta C10}$ and rIIa$^{\Delta S5V}$ are totally deficient in cleaving both cofactor molecules over a three-hour incubation period (FIGS. 8B, 8H, 9B, and 9H). These data are in complete agreement with our findings shown in Table 1, explain the fact that rPro$^{\Delta C10}$ and rPro$^{\Delta S5V}$ are devoid of clotting activity, and further attest of the dual role of the dipeptide Leu$^{480}$-Gln$^{481}$ during coagulation. Further analyses of the single or double mutants reveal a slight differentiation in cleavage and activation of the two cofactors by the various rIIa molecules. While rIIa$^{L480A}$ and rIIa$^{SL \rightarrow AA}$ appear devoid of activity towards fV (FIGS. 8D and 8E), both molecules slowly cleave fVIII at the Arg$^{372}$ and Arg$^{1689}$ activating cleavage sites (FIGS. 9D and 9E). Similarly, while rIIa$^{SLQ \rightarrow AAA}$ has no apparent activity towards fV (FIG. 8G) over a three hr time-period, the mutant enzyme cleaves fVIII slowly at the non-activating Arg$^{740}$ cleavage site (FIG. 9G). Finally, while rIIa$^{SQ \rightarrow AA}$ cleaves fV efficiently at Arg$^{709}$ to produce the heavy chain of fV and a Mr 220,000 intermediate (FIG. 8F), it is also efficient in cleaving fVIII at the Arg$^{372}$ and Arg$^{1689}$ activating cleavage sites (FIG. 9F). These two cofactors have strategic functions within the amplified coagulation response to vascular damage and must be activated to perform accordingly within their respective enzymatic complexes. The combined data explain the impaired procoagulant activity of rPro$^{SLQ \rightarrow AAA}$ (FIG. 2) which is deficient in producing large amounts of rIIa in a timely fashion (FIG. 5D). However, even when rIIa$^{SLQ \rightarrow AAA}$ is generated, the recombinant enzyme is deficient in activating the procofactors.

Figure 10:
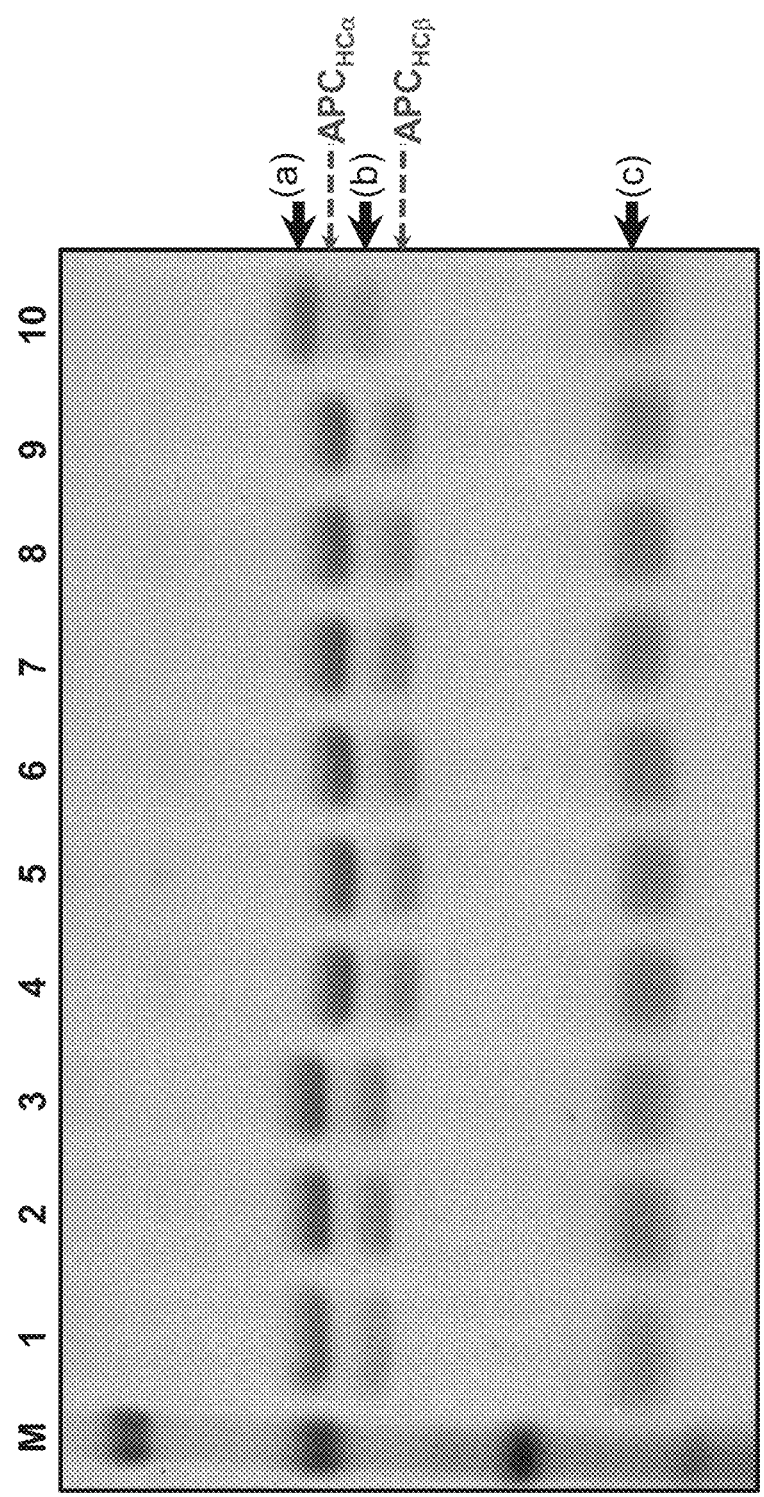
FIG. 10 shows the activation of protein C (PC) by rIIa. Plasma-derived PC (80 nM) was incubated with rIIa (8 nM), thrombomodulin, and PCPS as described below. Following a 3-hr incubation period each individual solution was mixed with 2% SDS, and 2% β-mercaptoethanol, heated for 5 min at 90° C., and analyzed on a 4-12% SDS-PAGE followed by staining with Coomassie Blue. Lane 1 PC alone no IIa; lane 2 PC alone, no IIa incubated with buffer for 3 hr; lane 3, PC and rIIa$^{\Delta S5V}$; lane 4, PC and plasma-derived IIa; lane 5, PC and rIIa$^{WT}$; lane 6, PC and rIIa$^{S478A}$; lane 7, PC and rIIa$^{L480A}$; lane 8, PC and rIIa$^{SL \to AA}$; lane 9, PC and rIIa$^{SQ \to AA}$; and lane 10, PC and rIIa$^{SLQ \to AAA}$. Positions of PC and APC heavy and light chains fragments are indicated at the right (a/b heavy chains, and c light chain). The two heavy chains of PC in plasma (a and b) have been identified earlier, differ by one glycosylation site, and have been extensively studied.

We next assessed the capability of the rIIa in the presence of thrombomodulin to activate PC and produce APC. FIG. 10 shows the results of such of an experiment and demonstrates that while rIIa$^{\Delta S5V}$ cannot cleave and activate PC, rIIa$^{SLQ \rightarrow AAA}$ has small but significant activity generating minute amounts of APC (FIG. 10, lanes 8 and 9) which in turn can cleave fV at Arg$^{506}$/Arg$^{306}$ and produce the characteristic Mr 30,000 fragment (data not shown). All other rIIa mutant molecules tested, for APC generation, have similar activities as rIIa$^{WT}$ or plasma-derived IIa under the condition described (FIG. 10).

These data demonstrate a differential requirement of IIa for cleavage and activation of both the procofactor molecules and PC and attest of the sensitive requirements of fV for cleavage and activation by IIa. Overall, these results provide original and novel indications that amino acids Leu$^{480}$ and Gln$^{481}$ within the serine protease domain of Pro, serve a dual purpose and are thus required for both efficient cleavage at Arg$^{320}$ by prothrombinase, but also represent an obligatory exosite for timely fV, fVIII, and PC activation. It is quite astonishing that these two amino acids identified herein have such a crucial physiological dual role during clot formation and can now be considered as the third exosite on Pro.

The data provided herein demonstrate that amino acid region 473-487 of Pro is required for timely activation of Pro through the meizothrombin pathway. While prior work using synthetic peptides suggested that this region of the cofactor may contain a fVa-dependent fXa binding site for Pro, the data presented herein with recombinant Pro molecules provides for the first time a mechanistic interpretation of these findings and identifies the crucial amino acids from this sequence responsible for the effect observed.

To elucidate the number and identity of the required amino acids within amino acid sequence 473-487 of Pro, we constructed, expressed, purified to homogeneity, and studied several rPro molecules with deletions and point mutations within this important regulatory region. We first investigated the effects of the fifteen amino acid deletion with rPro$^{\Delta 473-487}$, followed by experiments with rPro molecules containing overlapping deletions within this segment (rPro$^{\Delta N10}$ and rPro$^{\Delta C10}$, rPro$^{\Delta S5V}$ and rPro$^{\Delta SLQ}$). Several rPro molecules bearing single mutations (rPro$^{S478A}$, and rPro$^{L480A}$), double mutations (rPro$^{SL \rightarrow AA}$, rPro$^{SQ \rightarrow AA}$), and a triple mutation (rPro$^{SLQ \rightarrow AAA}$) were subsequently made. Membrane-bound fXa cleaves Pro sequentially at Arg$^{271}$ followed by Arg$^{320}$, forming small amounts of IIa. Under these conditions the activation of the deletion mutants rPro$^{\Delta 473-487}$, rPro$^{\Delta N10}$ rPro, rPro, rPro$^{\Delta S5V}$ and the triple and the deletion mutants (rPro$^{SLQ \rightarrow AAA}$ and rPro$^{\Delta SLQ}$) resulted in a modest increase of the rate of activation. In addition, activation of these five rPro molecules by fXa alone resulted in accumulation of prethrombin-2, with no apparent IIa formed. On the other hand activation of all these rPro mutants by fully assembled prothrombinase is significantly delayed. The combined data suggest that amino acids Leu$^{480}$ and Gln$^{481}$ within region 473-487 of Pro either represent or are responsible for the presentation of a fVa-dependent site for fXa on Pro which is essential for optimal rate of cleavage at Arg$^{320}$ which in turn is required for timely IIa formation at the place of vascular injury.

The autolysis loop of APC bears strong homology with the Pro sequence 473-487 (chymotrypsin numbering 149D-163). Replacement of several basic amino acids from this homologous region in APC by site directed mutagenesis to alanine, demonstrated the ability of this exosite to interact with its substrate fVa, and differentiate between the Arg$^{506}$ and Arg$^{306}$ cleavage sites. Yegneswaran et al. using synthetic peptides provided initial evidence that sequence 473-487 of Pro is able to disrupt prothrombinase assembly only in a fVa-dependent manner. Direct binding studies with fluorescence labeled fVa demonstrated a direct interaction of the cofactor with the peptide. However, human Pro had a greater affinity for the fluorescently labeled fVa than for the peptide 473-487, potentially due to the existence of other binding exosites on Pro that interact with fVa. Along these lines of evidence, Chen et al. identified one of these sequences within proexosite I of prothrombin containing basic residues Arg$^{35}$, Lys$^{36}$, Arg$^{67}$, Lys$^{70}$, Arg$^{73}$, Arg$^{75}$ and Arg$^{77}$ (chymotrypsin numbering), which is in close spatial proximity to region 473-487 of Pro. These investigations revealed that following replacement of all basic residues from proexosite I with Glu there was a significant effect on fXa within prothrombinase when compared to fXa alone in cleaving and activating Pro, suggesting that these specific amino acids are specific fVa-dependent recognition sites for fXa on Pro. Further kinetic studies by Chen et al. using hirudin showed that the peptide inhibited wild-type prethrombin-1 activation by prothrombinase whereas the hirudin peptide had no inhibitory effect on the activation of the mutated zymogen lacking the basic residues in proexosite I by fXa alone. The combined studies of Yegneswaran et al. and Chen et al. suggest the requirement of both sites for optimum productive interaction of prothrombinase with Pro and timely IIa formation.

The accelerating cofactor effect that fVa has on the prothrombinase mediated activation of Pro compared to Pro activation by fXa alone has been well-studied over the past 50 years but it is still not properly understood and no specific molecular role has yet been assigned to the cofactor. Research with discontinuous assays using a chromogenic substrate for IIa revealed that when fVa is incorporated into the prothrombinase complex the resulting $K_m$ of the reaction was decreased by 100-fold (corresponding to 100-fold increase in affinity of prothrombinase for Pro as compared to the affinity fXa alone for the substrate) while the catalytic efficiency ($k_{cat}$) of fXa was increased by 3,000-fold resulting in a 300,000-fold overall increase in the activity of prothrombinase (second order rate constant) for Pro compared to the activity of fXa alone. These data demonstrated that the two-subunit enzyme is one of the most proficient catalysts known in the human body similar to several other enzymes required for survival such as superoxide dismutase, catalase, and carbonic anhydrase. This significant increase in affinity of prothrombinase for its substrate is attributed to tighter binding of the enzymatic complex to Pro because its localization on the membrane surface by fVa. Thus, not only does fVa enhance the reaction of Pro activation during initiation of clotting, but at the late stages of coagulation, during the propagation phase, once all 20 nM of fV physiologically available is activated, it also promotes the meizothrombin pathway of IIa generation (initial cleavage to Arg$^{320}$ on Pro) resulting in the formation of the major enzymatic intermediate meizothrombin with demonstrated anti-coagulant activity. The longstanding hypothesis that fVa "localizes and positions" Pro in an optimum position for efficient catalysis by fXa consistent with the classical role of a cofactor for catalysis, was recently confirmed by computational studies with prothrombinase by Shim et al. These studies demonstrated that the acidic COOH-terminal portion of the heavy chain of fVa that is contiguous to the A2 domain of fVa, is essential in its ability to interact and snare the serine protease domain of Pro thus repositioning the Arg$^{320}$ cleavage site at an optimum position for timely cleavage by fXa and Pro activation at the site of vascular injury as earlier suggested and more recently experimentally demonstrated by our laboratory with synthetic peptides and recombinant fVa molecules mutated at these specific sites.

We show that following removal of the amino acid sequence 473-487 from Pro, prothrombinase loses the ability to efficiently form IIa because of impaired fVa-dependent cleavage of Pro by fXa at Arg$^{320}$. One easy explanation of these results was that elimination of such a huge portion of the molecule results in significant structural changes of the molecule that in turn have deleterious effects on Pro molecular conformation resulting in deficient prothrombinase activity. In spite of the fact that rPro$^{\Delta 473-487}$ was activated following the same pathways as rPro$^{WT}$ in the presence or absence of fVa albeit with different rates, and in the absence of a crystal structure of rPro$^{\Delta 473-487}$, there was still doubt about the structural integrity and function of a molecule bearing such a large deletion. Experiments using more modest overlapping deletions (with rPro$^{\Delta N10}$, rPro$^{\Delta C10}$, and rPro$^{\Delta S5V}$) as well as with a triple alanine mutant (rPro$^{SLQ \to AAA}$) and a triple deletion mutant (rPro$^{\Delta SLQ}$), demonstrated that these molecules are also hindered in their fVa-dependent cleavage at Arg$^{320}$ to a similar level as rPro$^{\Delta 473-487}$ (Table 1). These data provide original and unexpected evidence demonstrating that the minimal sequence required for the 3,000-fold increase in the catalytic efficiency of prothrombinase is carried at least partially by amino acid sequence Leu$^{480}$-Gln$^{481}$ of Pro. The findings presented herein silence the notion that the effect seen with rPro$^{\Delta 473-487}$ may be due to a structural change of the mutant molecule rather than to specific amino acid(s) missing from the rPro$^{\Delta 473-487}$, and assign the remarkable delay in Pro activation to two specific amino acids.

The kinetic findings presented herein revealed comparable $K_m$ and $k_{cat}$ constants for prothrombinase when rPro molecules bearing the single and double alanine mutations were used as substrate. However, when rPro$^{SLQ \to AAA}$ was the substrate for prothrombinase in the same discontinuous assay, there was an astonishing 21-fold increase in the $K_m$ and a modest 2.7-fold decrease in the $k_{cat}$ of the enzyme. Similar results were obtained with rPro$^{\Delta SLQ}$. Furthermore, rPro$^{SLQ \to AAA}$ and rPro$^{\Delta SLQ}$ were also found to be substantially deficient in clot formation in an assay using Pro-deficient plasma, while rIIa$^{SLQ \to AAA}$ was also deficient in S-2238 hydrolysis. rPro$^{SLQ \to AAA}$ was also impaired in cleaving fV, fVIII and PC. These data dovetail nicely with results obtained with rIIa$^{\Delta S5V}$ and rIIa$^{\Delta 473-487}$. We can thus hypothesize that the substantial increase in the $K_m$ of prothrombinase towards rPro$^{SLQ \to AAA}$ is due to a deficiency in prothrombinase in recognizing the mutant molecule because of the lack of Leu$^{480}$-Gln$^{481}$, while the decrease in enzymatic activity of the resulting rIIa$^{SLQ \to AAA}$ molecule is also the result of the absence of these two important amino acids' side chain. Additional data with rPro$^{\Delta SLQ}$ provides further evidence of the crucial role of amino acids Leu$^{480}$-Gln$^{481}$, and the peptide bond between these two amino acids since, when these residues are completely eliminated, the $K_m$ of the reaction increases by 32-fold while the $k_{cat}$ decreases by a stunning 16-fold (Table 2). Keeping in mind that the $Ser^{478} \rightarrow Ala$ substitution is of no consequence on both rPro activation and rIIa function, these surprising and unexpected results provide strong evidence in favor of the dual role of amino acids $Leu^{480}$ and $Gln^{481}$. Namely, these amino acids are required by prothrombinase to efficiently promote cleavage of Pro at $Arg^{320}$ and are also required by IIa for optimum esterase activity as well as to proficiently cleave and activate fV, fVIII, and PC. Finally, the possibility that elimination of these two residues from rPro results in an allosteric transition of the amino acids around/within the active site of rIIa, thus modifying the critical distances between the specific residues of the catalytic triad resulting in impaired catalysis, cannot be eliminated.

A comparison of crystal structures of Pro, meizothrombin, IIa, prethrombin-1, and prethrombin-2 was carried out to identify structural differences in/near the $Gly^{473}$-$Ile^{487}$ segment comprising the fVa-dependent fXa binding site. These residues adopt similar conformations in all of the crystal structures, with the $NH_2$-terminal residues $Gly^{473}$-$Gln^{476}$ being quite solvent-accessible or flexible, and residues $Pro^{477}$-$Ile^{487}$ being variable in their degree of solvent exposure. Residue $Ile^{487}$ is significantly more exposed in prothrombin (accessible surface area of >30 Å$^2$ compared to <10 Å$^2$ in meizothrombin and thrombin), as well as the adjacent $Pro^{486}$ (accessible surface area of ~15-30 Å$^2$ reducing to <10 Å$^2$ in meizothrombin and thrombin). The amount of solvent exposure of $Ile^{487}$ and $Pro^{486}$ appears to be heavily influenced by the flanking loops encompassing residues $Ala^{446}$-$Tyr^{454}$ and $Lys^{511}$-$Ser^{525}$ which adopt different conformations upon Pro activation (FIG. 11). For example, residues $Leu^{45}$-$Gly^{453}$ shift by as much as 10 Å closer to $Pro^{486}$ in meizothrombin and IIa compared to Pro, partially shielding this residue from solvent in the meizothrombin and IIa structures. Recently, Pozzi et al. used the crystal structure of Gla-domainless Pro with active site $Ser^{525} \rightarrow Ala$ to demonstrate that fVa has recognition sites in close proximity to $Arg^{320}$ ($Arg^{15}$ chymotrypsin numbering). These sites create a strong electrostatic potential due to a number of basic residues described by Chen et al. Through analysis of this published crystal structure, we have located this basic region to be in the vicinity of the $Leu^{480}$-$Gln^{481}$ amino acid sequence of Pro that we found to be required for efficient initial cleavage at $Arg^{320}$ by prothrombinase. It is noteworthy that a very recent study by Pozzi et al. demonstrated a crucial role for linker 2 for the rate of activation of Pro by prothrombinase and suggested that this region maybe involved in the interaction of Pro with the cofactor. These data are in complete accord with data showing that fragment 1 and more precisely the kringle 2 region is involved in the interaction of fVa as part of prothrombinase with Pro. Finally, a close comparison of crystal structures of Pro and IIa revealed that residues $Ser^{478}$, $Leu^{480}$, and $Gln^{481}$ adopt similar conformations in both structures. The $Ser^{478}$ side chain is exposed on the surface of both molecules, while the $Leu^{480}$ side chain is surrounded by other residues and not accessible to solvent. $Gln^{481}$ is partially solvent-exposed in both Pro and IIa. The $Ser^{478}$/$Leu^{480}$/$Gln^{481}$ residues are near ABE-I (FIG. 11) but >15 Å from the catalytic $Ser^{525}$ residue, and even more distant from ABE-II.

In conclusion, in this study we provide original and unequivocal evidence for the dual effect of amino acids $Leu^{480}$ and $Gln^{481}$ of Pro. This study also provides unprecedented information on prothrombinase and sheds light into the understanding of the "cofactor effect" of fVa and the precise molecular interactions that fVa has with a minimal region located in the serine protease domain of Pro. In addition, through the use of alanine substitution in exposed amino acids ($Ser^{478}$ and $Gln^{481}$) or homologous to other serine proteases ($Leu^{480}$) (FIG. 11), we can conclude that the two valines ($Val^{479}$ and $Val^{482}$) in this region, which are held constant in all of our mutant molecules bearing alanine substitutions, or in the $rPro^{\Delta SLQ}$ molecules, do not appear to contribute significantly to the overall molecular interactions between the fVa-dependent interaction of fXa and rPro or in the overall catalytic and esterase activity of rIIa. Future mutagenesis studies within the amino acids uncovered herein, paired with judiciously selected mutations within proexosite-I and/or proexosite-II of Pro, should be able to elucidate the intermolecular communications within Pro, required for both optimal fVa-dependent activation of Pro and subsequent IIa catalytic activity towards its numerous physiological substrates. Finally, our results provide evidence for the production of large quantities of $rPro^{\Delta S5V}$, $rPro^{SLQ \rightarrow AAA}$, or $rPro^{\Delta SLQ}$ that could be used as therapeutic agents since they would compete with the natural substrate in vivo, when infused in individuals with prothrombotic tendencies.

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

While embodiments of the invention have been illustrated and described, it is not intended that these embodiments illustrate and describe all possible forms of the invention. Those familiar with the art to which the invention relates will appreciate other ways of carrying out the invention defined by the following claims. Rather, the words used herein are words of description and not limitation, and it will be apparent to one of ordinary skill in the art that many changes and modifications can be made thereto without departing from the spirit or scope of the invention as set forth herein.

ABBREVIATIONS USED ARE

PS, L-α-phosphatidylserine; PC, L-α-phosphatidylcholine;
PCPS, small unilamellar phospholipids vesicles composed of 75% PC and 25% PS (w/w);
SDS-PAGE, Sodium dodecyl sulfate polyacrylamide gel electrophoresis;
$rPro^{WT}$, recombinant wild type human prothrombin;
$rIIa^{WT}$ recombinant wild type human α-thrombin;
$rPro^{\Delta 473487}$, recombinant human prothrombin with region 473-487 deleted;
$rIIa^{\Delta 473-487}$, recombinant human α-thrombin with region 473-487 deleted;
$rPro^{\Delta N10}$ recombinant human prothrombin missing amino acids GKGQPSVLQV;
$rIIa^{\Delta N10}$ recombinant human α-thrombin missing amino acids GKGQPSVLQV;
$rPro^{\Delta C10}$ recombinant human prothrombin missing amino acids SVLQVVNLPI;
$rIIa^{\Delta C10}$ recombinant human prothrombin missing amino acids SVLQVVNLPI;
$rPro^{\Delta S5V}$, recombinant human prothrombin with region SVLQV deleted;
$rIIa^{\Delta S5V}$, recombinant human α-thrombin with region SVLQV deleted;

rPro$^{S478A}$, recombinant human prothrombin with the mutation S$^{478}$→Ala;
rIIa$^{S478A}$, recombinant human α-thrombin with the mutation Ser$^{478}$→Ala;
rPro$^{L480A}$, recombinant human prothrombin with the mutation Leu$^{480}$→Ala;
rIIa$^{L480A}$, recombinant human α-thrombin with the mutation Leu$^{480}$→Ala;
rPro$^{SL→AA}$, recombinant human prothrombin with the mutation Ser$^{478}$/Leu$^{480}$→Ala;
rIIa$^{SL→AA}$, recombinant human α-thrombin with the mutation Ser$^{478}$/Leu$^{480}$→Ala;
rPro$^{SQ→AA}$, recombinant human prothrombin with the mutation Ser$^{478}$/Gln$^{481}$→Ala;
rIIa$^{SQ→AA}$, recombinant human α-thrombin with the mutation Ser$^{478}$/Gln$^{481}$→Ala;
rPro$^{SLQ→AA}$, recombinant human prothrombin with the mutation Ser$^{478}$/Leu$^{480}$/Gln$^{481}$→A;
rIIa$^{SLQ→AA}$, recombinant human α-thrombin with the mutation Ser$^{478}$/Leu$^{480}$/Gln$^{481}$→A;
rPro$^{ΔSLQ}$, recombinant human prothrombin with amino acids Ser$^{478}$/Leu$^{480}$/Gln$^{48}$ deleted;
rIIa$^{ΔSLQ}$, recombinant human α-thrombin with amino acids Ser$^{478}$/Leu$^{480}$/Gln$^{481}$ deleted.

What is claimed is:

1. A recombinant prothrombin polypeptide, wherein the polypeptide comprises a deletion of amino acid residues $Ser^{478}$, $Leu^{480}$, and $Gln^{481}$ or a substitution of $Ser^{478}$, $Leu^{480}$, and $Gln^{481}$ with alanine.

2. The recombinant prothrombin of polypeptide claim 1, wherein the polypeptide comprises a substitution of amino acid residues $Ser^{478}$, $Leu^{480}$, and $Gln^{481}$ with alanine.

3. The recombinant prothrombin of polypeptide claim 1, wherein the polypeptide comprises a deletion of amino acid residues $Ser^{478}$, $Leu^{480}$, and $Gln^{481}$.

4. The recombinant prothrombin of polypeptide claim 1, wherein the modification is a substitution of Ala for each of the $Ser^{478}$, $Leu^{480}$, and $Gln^{481}$.

5. A method of reducing coagulation in a subject who has or is at risk of having thrombosis, the method comprising administering a polypeptide according to any one of claims 1 and 2-3.

6. An isolated polynucleotide which encodes a polypeptide characterized by:

(a) having anti-coagulant activity; and (b) having the amino acid sequence of prothrombin comprising a deletion of amino acid residues $Ser^{478}$, $Leu^{480}$, and $Gln^{481}$ or a substitution of $Ser^{478}$, $Leu^{480}$, and $Gln^{481}$ with alanine.

7. A non-human host cell which contains the polynucleotide of claim 6.

8. A recombinant expression vector which contains the polynucleotide of claim 6.

9. The vector of claim 8, wherein the vector is a plasmid.

10. The vector of claim 8, wherein the vector is a virus.

11. A method for producing a polypeptide having an amino acid sequence of prothrombin, wherein the polypeptide acts as a prothrombin molecule which is incapable of activation comprising:

(a) introducing into a host cell an expression vector which contains a nucleotide sequence which encodes a polypeptide having an amino acid sequence of prothrombin comprising a deletion of amino acid residues $Ser^{478}$, $Leu^{480}$, and $Gln^{481}$ or a substitution of $Ser^{478}$, $Leu^{480}$, and $Gln^{481}$ with alanine;

(b) culturing the host cell in an appropriate medium; and (c) isolating the polypeptide product encoded by the expression vector.

* * * * *

SEQUENCE LISTING

```
<160> NUMBER OF SEQ ID NOS: 33

<210> SEQ ID NO 1
<211> LENGTH: 579
<212> TYPE: PRT
<213> ORGANISM: Homo Sapiens

<400> SEQUENCE: 1

Ala Asn Thr Phe Leu Glu Glu Val Arg Lys Gly Asn Leu Glu Arg Glu
1               5                   10                  15

Cys Val Glu Glu Thr Cys Ser Tyr Glu Glu Ala Phe Glu Ala Leu Glu
            20                  25                  30

Ser Ser Thr Ala Thr Asp Val Phe Trp Ala Lys Tyr Thr Ala Cys Glu
        35                  40                  45

Thr Ala Arg Thr Pro Arg Asp Lys Leu Ala Ala Cys Leu Glu Gly Asn
    50                  55                  60

Cys Ala Glu Gly Leu Gly Thr Asn Tyr Arg Gly His Val Asn Ile Thr
65                  70                  75                  80

Arg Ser Gly Ile Glu Cys Gln Leu Trp Arg Ser Arg Tyr Pro His Lys
                85                  90                  95

Pro Glu Ile Asn Ser Thr Thr His Pro Gly Ala Asp Leu Gln Glu Asn
            100                 105                 110

Phe Cys Arg Asn Pro Asp Ser Ser Thr Thr Gly Pro Trp Cys Tyr Thr
        115                 120                 125

Thr Asp Pro Thr Val Arg Arg Gln Glu Cys Ser Ile Pro Val Cys Gly
    130                 135                 140

Gln Asp Gln Val Thr Val Ala Met Thr Pro Arg Ser Glu Gly Ser Ser
145                 150                 155                 160

Val Asn Leu Ser Pro Pro Leu Glu Gln Cys Val Pro Asp Arg Gly Gln
                165                 170                 175

Gln Tyr Gln Gly Arg Leu Ala Val Thr Thr His Gly Leu Pro Cys Leu
            180                 185                 190

Ala Trp Ala Ser Ala Gln Ala Lys Ala Leu Ser Lys His Gln Asp Phe
        195                 200                 205

Asn Ser Ala Val Gln Leu Val Glu Asn Phe Cys Arg Asn Pro Asp Gly
    210                 215                 220

Asp Glu Glu Gly Val Trp Cys Tyr Val Ala Gly Lys Pro Gly Asp Phe
225                 230                 235                 240

Gly Tyr Cys Asp Leu Asn Tyr Cys Glu Glu Ala Val Glu Glu Glu Thr
                245                 250                 255

Gly Asp Gly Leu Asp Glu Asp Ser Asp Arg Ala Ile Glu Gly Arg Thr
            260                 265                 270

Ala Thr Ser Glu Tyr Gln Thr Phe Phe Asn Pro Arg Thr Phe Gly Ser
        275                 280                 285
```

```
Gly Glu Ala Asp Cys Gly Leu Arg Pro Leu Phe Glu Lys Lys Ser Leu
        290                 295                 300

Glu Asp Lys Thr Glu Arg Glu Leu Leu Glu Ser Tyr Ile Asp Gly Arg
305                 310                 315                 320

Ile Val Glu Gly Ser Asp Ala Glu Ile Gly Met Ser Pro Trp Gln Val
                325                 330                 335

Met Leu Phe Arg Lys Ser Pro Gln Glu Leu Leu Cys Gly Ala Ser Leu
            340                 345                 350

Ile Ser Asp Arg Trp Val Leu Thr Ala Ala His Cys Leu Leu Tyr Pro
        355                 360                 365

Pro Trp Asp Lys Asn Phe Thr Glu Asn Asp Leu Leu Val Arg Ile Gly
    370                 375                 380

Lys His Ser Arg Thr Arg Tyr Glu Arg Asn Ile Glu Lys Ile Ser Met
385                 390                 395                 400

Leu Glu Lys Ile Tyr Ile His Pro Arg Tyr Asn Trp Arg Glu Asn Leu
                405                 410                 415

Asp Arg Asp Ile Ala Leu Met Lys Leu Lys Pro Val Ala Phe Ser
            420                 425                 430

Asp Tyr Ile His Pro Val Cys Leu Pro Asp Arg Glu Thr Ala Ala Ser
        435                 440                 445

Leu Leu Gln Ala Gly Tyr Lys Gly Arg Val Thr Gly Trp Gly Asn Leu
450                 455                 460

Lys Glu Thr Trp Thr Ala Asn Val Gly Lys Gly Gln Pro Ser Val Leu
465                 470                 475                 480

Gln Val Val Asn Leu Pro Ile Val Glu Arg Pro Val Cys Lys Asp Ser
                485                 490                 495

Thr Arg Ile Arg Ile Thr Asp Asn Met Phe Cys Ala Gly Tyr Lys Pro
            500                 505                 510

Asp Glu Gly Lys Arg Gly Asp Ala Cys Glu Gly Asp Ser Gly Gly Pro
        515                 520                 525

Phe Val Met Lys Ser Pro Phe Asn Asn Arg Trp Tyr Gln Met Gly Ile
    530                 535                 540

Val Ser Trp Gly Glu Gly Cys Asp Arg Asp Gly Lys Tyr Gly Phe Tyr
545                 550                 555                 560

Thr His Val Phe Arg Leu Lys Lys Trp Ile Gln Lys Val Ile Asp Gln
                565                 570                 575

Phe Gly Glu

<210> SEQ ID NO 2
<211> LENGTH: 579
<212> TYPE: PRT
<213> ORGANISM: Artificial Sequence
<220> FEATURE:
<223> OTHER INFORMATION: Synthetic
<220> FEATURE:
<221> NAME/KEY: X
<222> LOCATION: (473)..(487)
<223> OTHER INFORMATION: Each X may be any naturally occurring amino
      acid or a deletion

<400> SEQUENCE: 2

Ala Asn Thr Phe Leu Glu Glu Val Arg Lys Gly Asn Leu Glu Arg Glu
1               5                   10                  15

Cys Val Glu Glu Thr Cys Ser Tyr Glu Glu Ala Phe Glu Ala Leu Glu
            20                  25                  30

Ser Ser Thr Ala Thr Asp Val Phe Trp Ala Lys Tyr Thr Ala Cys Glu
```

```
                35                  40                  45
Thr Ala Arg Thr Pro Arg Asp Lys Leu Ala Ala Cys Leu Glu Gly Asn
 50                  55                  60

Cys Ala Glu Gly Leu Gly Thr Asn Tyr Arg Gly His Val Asn Ile Thr
 65                  70                  75                  80

Arg Ser Gly Ile Glu Cys Gln Leu Trp Arg Ser Arg Tyr Pro His Lys
                     85                  90                  95

Pro Glu Ile Asn Ser Thr Thr His Pro Gly Ala Asp Leu Gln Glu Asn
                100                 105                 110

Phe Cys Arg Asn Pro Asp Ser Ser Thr Thr Gly Pro Trp Cys Tyr Thr
            115                 120                 125

Thr Asp Pro Thr Val Arg Arg Gln Glu Cys Ser Ile Pro Val Cys Gly
        130                 135                 140

Gln Asp Gln Val Thr Val Ala Met Thr Pro Arg Ser Glu Gly Ser Ser
145                 150                 155                 160

Val Asn Leu Ser Pro Pro Leu Glu Gln Cys Val Pro Asp Arg Gly Gln
                165                 170                 175

Gln Tyr Gln Gly Arg Leu Ala Val Thr Thr His Gly Leu Pro Cys Leu
                180                 185                 190

Ala Trp Ala Ser Ala Gln Ala Lys Ala Leu Ser Lys His Gln Asp Phe
            195                 200                 205

Asn Ser Ala Val Gln Leu Val Glu Asn Phe Cys Arg Asn Pro Asp Gly
        210                 215                 220

Asp Glu Glu Gly Val Trp Cys Tyr Val Ala Gly Lys Pro Gly Asp Phe
225                 230                 235                 240

Gly Tyr Cys Asp Leu Asn Tyr Cys Glu Glu Ala Val Glu Glu Glu Thr
                245                 250                 255

Gly Asp Gly Leu Asp Glu Asp Ser Asp Arg Ala Ile Glu Gly Arg Thr
            260                 265                 270

Ala Thr Ser Glu Tyr Gln Thr Phe Phe Asn Pro Arg Thr Phe Gly Ser
        275                 280                 285

Gly Glu Ala Asp Cys Gly Leu Arg Pro Leu Phe Glu Lys Lys Ser Leu
290                 295                 300

Glu Asp Lys Thr Glu Arg Glu Leu Leu Glu Ser Tyr Ile Asp Gly Arg
305                 310                 315                 320

Ile Val Glu Gly Ser Asp Ala Glu Ile Gly Met Ser Pro Trp Gln Val
                325                 330                 335

Met Leu Phe Arg Lys Ser Pro Gln Glu Leu Leu Cys Gly Ala Ser Leu
            340                 345                 350

Ile Ser Asp Arg Trp Val Leu Thr Ala Ala His Cys Leu Leu Tyr Pro
        355                 360                 365

Pro Trp Asp Lys Asn Phe Thr Glu Asn Asp Leu Leu Val Arg Ile Gly
        370                 375                 380

Lys His Ser Arg Thr Arg Tyr Glu Arg Asn Ile Glu Lys Ile Ser Met
385                 390                 395                 400

Leu Glu Lys Ile Tyr Ile His Pro Arg Tyr Asn Trp Arg Glu Asn Leu
                405                 410                 415

Asp Arg Asp Ile Ala Leu Met Lys Leu Lys Lys Pro Val Ala Phe Ser
            420                 425                 430

Asp Tyr Ile His Pro Val Cys Leu Pro Asp Arg Glu Thr Ala Ala Ser
        435                 440                 445

Leu Leu Gln Ala Gly Tyr Lys Gly Arg Val Thr Gly Trp Gly Asn Leu
450                 455                 460
```

```
Lys Glu Thr Trp Thr Ala Asn Val Xaa Xaa Xaa Xaa Xaa Xaa Xaa Xaa
465                 470                 475                 480

Xaa Xaa Xaa Xaa Xaa Xaa Val Glu Arg Pro Val Cys Lys Asp Ser
                485                 490                 495

Thr Arg Ile Arg Ile Thr Asp Asn Met Phe Cys Ala Gly Tyr Lys Pro
            500                 505                 510

Asp Glu Gly Lys Arg Gly Asp Ala Cys Glu Gly Asp Ser Gly Gly Pro
            515                 520                 525

Phe Val Met Lys Ser Pro Phe Asn Asn Arg Trp Tyr Gln Met Gly Ile
        530                 535                 540

Val Ser Trp Gly Glu Gly Cys Asp Arg Asp Gly Lys Tyr Gly Phe Tyr
545                 550                 555                 560

Thr His Val Phe Arg Leu Lys Lys Trp Ile Gln Lys Val Ile Asp Gln
                565                 570                 575

Phe Gly Glu

<210> SEQ ID NO 3
<211> LENGTH: 579
<212> TYPE: PRT
<213> ORGANISM: Artificial Sequence
<220> FEATURE:
<223> OTHER INFORMATION: Synthetic
<220> FEATURE:
<221> NAME/KEY: X
<222> LOCATION: (478)..(481)
<223> OTHER INFORMATION: Each X may be any naturally occurring amino
      acid or a deletion

<400> SEQUENCE: 3

Ala Asn Thr Phe Leu Glu Glu Val Arg Lys Gly Asn Leu Glu Arg Glu
1               5                   10                  15

Cys Val Glu Glu Thr Cys Ser Tyr Glu Glu Ala Phe Glu Ala Leu Glu
            20                  25                  30

Ser Ser Thr Ala Thr Asp Val Phe Trp Ala Lys Tyr Thr Ala Cys Glu
        35                  40                  45

Thr Ala Arg Thr Pro Arg Asp Lys Leu Ala Ala Cys Leu Glu Gly Asn
    50                  55                  60

Cys Ala Glu Gly Leu Gly Thr Asn Tyr Arg Gly His Val Asn Ile Thr
65                  70                  75                  80

Arg Ser Gly Ile Glu Cys Gln Leu Trp Arg Ser Arg Tyr Pro His Lys
                85                  90                  95

Pro Glu Ile Asn Ser Thr Thr His Pro Gly Ala Asp Leu Gln Glu Asn
            100                 105                 110

Phe Cys Arg Asn Pro Asp Ser Ser Thr Thr Gly Pro Trp Cys Tyr Thr
        115                 120                 125

Thr Asp Pro Thr Val Arg Arg Gln Glu Cys Ser Ile Pro Val Cys Gly
    130                 135                 140

Gln Asp Gln Val Thr Val Ala Met Thr Pro Arg Ser Glu Gly Ser Ser
145                 150                 155                 160

Val Asn Leu Ser Pro Pro Leu Glu Gln Cys Val Pro Asp Arg Gly Gln
                165                 170                 175

Gln Tyr Gln Gly Arg Leu Ala Val Thr Thr His Gly Leu Pro Cys Leu
            180                 185                 190

Ala Trp Ala Ser Ala Gln Ala Lys Ala Leu Ser Lys His Gln Asp Phe
        195                 200                 205

Asn Ser Ala Val Gln Leu Val Glu Asn Phe Cys Arg Asn Pro Asp Gly
```

```
            210                 215                 220
Asp Glu Glu Gly Val Trp Cys Tyr Val Ala Gly Lys Pro Gly Asp Phe
225                 230                 235                 240

Gly Tyr Cys Asp Leu Asn Tyr Cys Glu Glu Ala Val Glu Glu Glu Thr
                245                 250                 255

Gly Asp Gly Leu Asp Glu Asp Ser Asp Arg Ala Ile Glu Gly Arg Thr
                260                 265                 270

Ala Thr Ser Glu Tyr Gln Thr Phe Phe Asn Pro Arg Thr Phe Gly Ser
                275                 280                 285

Gly Glu Ala Asp Cys Gly Leu Arg Pro Leu Phe Glu Lys Lys Ser Leu
            290                 295                 300

Glu Asp Lys Thr Glu Arg Glu Leu Leu Glu Ser Tyr Ile Asp Gly Arg
305                 310                 315                 320

Ile Val Glu Gly Ser Asp Ala Glu Ile Gly Met Ser Pro Trp Gln Val
                325                 330                 335

Met Leu Phe Arg Lys Ser Pro Gln Glu Leu Leu Cys Gly Ala Ser Leu
                340                 345                 350

Ile Ser Asp Arg Trp Val Leu Thr Ala Ala His Cys Leu Leu Tyr Pro
                355                 360                 365

Pro Trp Asp Lys Asn Phe Thr Glu Asn Asp Leu Leu Val Arg Ile Gly
                370                 375                 380

Lys His Ser Arg Thr Arg Tyr Glu Arg Asn Ile Glu Lys Ile Ser Met
385                 390                 395                 400

Leu Glu Lys Ile Tyr Ile His Pro Arg Tyr Asn Trp Arg Glu Asn Leu
                405                 410                 415

Asp Arg Asp Ile Ala Leu Met Lys Leu Lys Pro Val Ala Phe Ser
                420                 425                 430

Asp Tyr Ile His Pro Val Cys Leu Pro Asp Arg Glu Thr Ala Ala Ser
                435                 440                 445

Leu Leu Gln Ala Gly Tyr Lys Gly Arg Val Thr Gly Trp Gly Asn Leu
            450                 455                 460

Lys Glu Thr Trp Thr Ala Asn Val Gly Lys Gly Gln Pro Xaa Val Xaa
465                 470                 475                 480

Xaa Val Val Asn Leu Pro Ile Val Glu Arg Pro Val Cys Lys Asp Ser
                485                 490                 495

Thr Arg Ile Arg Ile Thr Asp Asn Met Phe Cys Ala Gly Tyr Lys Pro
                500                 505                 510

Asp Glu Gly Lys Arg Gly Asp Ala Cys Glu Gly Asp Ser Gly Gly Pro
                515                 520                 525

Phe Val Met Lys Ser Pro Phe Asn Asn Arg Trp Tyr Gln Met Gly Ile
                530                 535                 540

Val Ser Trp Gly Glu Gly Cys Asp Arg Asp Gly Lys Tyr Gly Phe Tyr
545                 550                 555                 560

Thr His Val Phe Arg Leu Lys Lys Trp Ile Gln Lys Val Ile Asp Gln
                565                 570                 575

Phe Gly Glu

<210> SEQ ID NO 4
<211> LENGTH: 42
<212> TYPE: DNA
<213> ORGANISM: Artificial Sequence
<220> FEATURE:
<223> OTHER INFORMATION: Synthetic

<400> SEQUENCE: 4
```

```
gagacgtgga cagccaacgt tgtggagcgg ccggtctgca ag                              42
```

<210> SEQ ID NO 5
<211> LENGTH: 42
<212> TYPE: DNA
<213> ORGANISM: Artificial Sequence
<220> FEATURE:
<223> OTHER INFORMATION: Synthetic

<400> SEQUENCE: 5

```
cttgcagacc ggccgctcca caacgttggc tgtccacgtc tc                              42
```

<210> SEQ ID NO 6
<211> LENGTH: 569
<212> TYPE: PRT
<213> ORGANISM: Artificial Sequence
<220> FEATURE:
<223> OTHER INFORMATION: Synthetic

<400> SEQUENCE: 6

```
Ala Asn Thr Phe Leu Glu Glu Val Arg Lys Gly Asn Leu Glu Arg Glu
1               5                   10                  15

Cys Val Glu Glu Thr Cys Ser Tyr Glu Glu Ala Phe Glu Ala Leu Glu
            20                  25                  30

Ser Ser Thr Ala Thr Asp Val Phe Trp Ala Lys Tyr Thr Ala Cys Glu
        35                  40                  45

Thr Ala Arg Thr Pro Arg Asp Lys Leu Ala Ala Cys Leu Glu Gly Asn
    50                  55                  60

Cys Ala Glu Gly Leu Gly Thr Asn Tyr Arg Gly His Val Asn Ile Thr
65                  70                  75                  80

Arg Ser Gly Ile Glu Cys Gln Leu Trp Arg Ser Arg Tyr Pro His Lys
                85                  90                  95

Pro Glu Ile Asn Ser Thr Thr His Pro Gly Ala Asp Leu Gln Glu Asn
            100                 105                 110

Phe Cys Arg Asn Pro Asp Ser Ser Thr Thr Gly Pro Trp Cys Tyr Thr
        115                 120                 125

Thr Asp Pro Thr Val Arg Arg Gln Glu Cys Ser Ile Pro Val Cys Gly
    130                 135                 140

Gln Asp Gln Val Thr Val Ala Met Thr Pro Arg Ser Glu Gly Ser Ser
145                 150                 155                 160

Val Asn Leu Ser Pro Pro Leu Glu Gln Cys Val Pro Asp Arg Gly Gln
                165                 170                 175

Gln Tyr Gln Gly Arg Leu Ala Val Thr Thr His Gly Leu Pro Cys Leu
            180                 185                 190

Ala Trp Ala Ser Ala Gln Ala Lys Ala Leu Ser Lys His Gln Asp Phe
        195                 200                 205

Asn Ser Ala Val Gln Leu Val Glu Asn Phe Cys Arg Asn Pro Asp Gly
    210                 215                 220

Asp Glu Glu Gly Val Trp Cys Tyr Val Ala Gly Lys Pro Gly Asp Phe
225                 230                 235                 240

Gly Tyr Cys Asp Leu Asn Tyr Cys Glu Glu Ala Val Glu Glu Glu Thr
                245                 250                 255

Gly Asp Gly Leu Asp Glu Asp Ser Asp Arg Ala Ile Glu Gly Arg Thr
            260                 265                 270

Ala Thr Ser Glu Tyr Gln Thr Phe Phe Asn Pro Arg Thr Phe Gly Ser
        275                 280                 285
```

-continued

Gly Glu Ala Asp Cys Gly Leu Arg Pro Leu Phe Glu Lys Lys Ser Leu
    290                 295                 300

Glu Asp Lys Thr Glu Arg Glu Leu Leu Glu Ser Tyr Ile Asp Gly Arg
305                 310                 315                 320

Ile Val Glu Gly Ser Asp Ala Glu Ile Gly Met Ser Pro Trp Gln Val
                325                 330                 335

Met Leu Phe Arg Lys Ser Pro Gln Glu Leu Leu Cys Gly Ala Ser Leu
            340                 345                 350

Ile Ser Asp Arg Trp Val Leu Thr Ala Ala His Cys Leu Leu Tyr Pro
        355                 360                 365

Pro Trp Asp Lys Asn Phe Thr Glu Asn Asp Leu Leu Val Arg Ile Gly
370                 375                 380

Lys His Ser Arg Thr Arg Tyr Glu Arg Asn Ile Glu Lys Ile Ser Met
385                 390                 395                 400

Leu Glu Lys Ile Tyr Ile His Pro Arg Tyr Asn Trp Arg Glu Asn Leu
                405                 410                 415

Asp Arg Asp Ile Ala Leu Met Lys Leu Lys Pro Val Ala Phe Ser
            420                 425                 430

Asp Tyr Ile His Pro Val Cys Leu Pro Asp Arg Glu Thr Ala Ala Ser
        435                 440                 445

Leu Leu Gln Ala Gly Tyr Lys Gly Arg Val Thr Gly Trp Gly Asn Leu
450                 455                 460

Lys Glu Thr Trp Thr Ala Asn Val Val Asn Leu Pro Ile Val Glu Arg
465                 470                 475                 480

Pro Val Cys Lys Asp Ser Thr Arg Ile Arg Ile Thr Asp Asn Met Phe
                485                 490                 495

Cys Ala Gly Tyr Lys Pro Asp Glu Gly Lys Arg Gly Asp Ala Cys Glu
            500                 505                 510

Gly Asp Ser Gly Gly Pro Phe Val Met Lys Ser Pro Phe Asn Asn Arg
        515                 520                 525

Trp Tyr Gln Met Gly Ile Val Ser Trp Gly Glu Gly Cys Asp Arg Asp
    530                 535                 540

Gly Lys Tyr Gly Phe Tyr Thr His Val Phe Arg Leu Lys Lys Trp Ile
545                 550                 555                 560

Gln Lys Val Ile Asp Gln Phe Gly Glu
                565

<210> SEQ ID NO 7
<211> LENGTH: 40
<212> TYPE: DNA
<213> ORGANISM: Artificial Sequence
<220> FEATURE:
<223> OTHER INFORMATION: Synthetic

<400> SEQUENCE: 7
gacgtggaca gccaacgttg tgaacctgcc cattgtggag        40

<210> SEQ ID NO 8
<211> LENGTH: 40
<212> TYPE: DNA
<213> ORGANISM: Artificial Sequence
<220> FEATURE:
<223> OTHER INFORMATION: Synthetic

<400> SEQUENCE: 8
ctccacaatg ggcaggttca caacgttggc tgtccacgtc        40

-continued

<210> SEQ ID NO 9
<211> LENGTH: 569
<212> TYPE: PRT
<213> ORGANISM: Artificial Sequence
<220> FEATURE:
<223> OTHER INFORMATION: Synthetic

<400> SEQUENCE: 9

Ala Asn Thr Phe Leu Glu Glu Val Arg Lys Gly Asn Leu Glu Arg Glu
1               5                   10                  15

Cys Val Glu Thr Cys Ser Tyr Glu Ala Phe Glu Ala Leu Glu
                20                  25                  30

Ser Ser Thr Ala Thr Asp Val Phe Trp Ala Lys Tyr Thr Ala Cys Glu
            35                  40                  45

Thr Ala Arg Thr Pro Arg Asp Lys Leu Ala Ala Cys Leu Glu Gly Asn
        50                  55                  60

Cys Ala Glu Gly Leu Gly Thr Asn Tyr Arg Gly His Val Asn Ile Thr
65                  70                  75                  80

Arg Ser Gly Ile Glu Cys Gln Leu Trp Arg Ser Arg Tyr Pro His Lys
                85                  90                  95

Pro Glu Ile Asn Ser Thr Thr His Pro Gly Ala Asp Leu Gln Glu Asn
            100                 105                 110

Phe Cys Arg Asn Pro Asp Ser Ser Thr Thr Gly Pro Trp Cys Tyr Thr
        115                 120                 125

Thr Asp Pro Thr Val Arg Arg Gln Glu Cys Ser Ile Pro Val Cys Gly
130                 135                 140

Gln Asp Gln Val Thr Val Ala Met Thr Pro Arg Ser Glu Gly Ser Ser
145                 150                 155                 160

Val Asn Leu Ser Pro Pro Leu Glu Gln Cys Val Pro Asp Arg Gly Gln
                165                 170                 175

Gln Tyr Gln Gly Arg Leu Ala Val Thr Thr His Gly Leu Pro Cys Leu
            180                 185                 190

Ala Trp Ala Ser Ala Gln Ala Lys Ala Leu Ser Lys His Gln Asp Phe
        195                 200                 205

Asn Ser Ala Val Gln Leu Val Glu Asn Phe Cys Arg Asn Pro Asp Gly
210                 215                 220

Asp Glu Glu Gly Val Trp Cys Tyr Val Ala Gly Lys Pro Gly Asp Phe
225                 230                 235                 240

Gly Tyr Cys Asp Leu Asn Tyr Cys Glu Glu Ala Val Glu Glu Glu Thr
                245                 250                 255

Gly Asp Gly Leu Asp Glu Asp Ser Asp Arg Ala Ile Glu Gly Arg Thr
            260                 265                 270

Ala Thr Ser Glu Tyr Gln Thr Phe Phe Asn Pro Arg Thr Phe Gly Ser
        275                 280                 285

Gly Glu Ala Asp Cys Gly Leu Arg Pro Leu Phe Glu Lys Lys Ser Leu
290                 295                 300

Glu Asp Lys Thr Glu Arg Glu Leu Leu Glu Ser Tyr Ile Asp Gly Arg
305                 310                 315                 320

Ile Val Glu Gly Ser Asp Ala Glu Ile Gly Met Ser Pro Trp Gln Val
                325                 330                 335

Met Leu Phe Arg Lys Ser Pro Gln Glu Leu Leu Cys Gly Ala Ser Leu
            340                 345                 350

Ile Ser Asp Arg Trp Val Leu Thr Ala Ala His Cys Leu Leu Tyr Pro
        355                 360                 365

Pro Trp Asp Lys Asn Phe Thr Glu Asn Asp Leu Leu Val Arg Ile Gly

```
                      370                 375                 380
Lys His Ser Arg Thr Arg Tyr Glu Arg Asn Ile Glu Lys Ile Ser Met
385                 390                 395                 400

Leu Glu Lys Ile Tyr Ile His Pro Arg Tyr Asn Trp Arg Glu Asn Leu
                405                 410                 415

Asp Arg Asp Ile Ala Leu Met Lys Leu Lys Lys Pro Val Ala Phe Ser
            420                 425                 430

Asp Tyr Ile His Pro Val Cys Leu Pro Asp Arg Glu Thr Ala Ala Ser
        435                 440                 445

Leu Leu Gln Ala Gly Tyr Lys Gly Arg Val Thr Gly Trp Gly Asn Leu
    450                 455                 460

Lys Glu Thr Trp Thr Ala Asn Val Gly Lys Gly Gln Pro Val Glu Arg
465                 470                 475                 480

Pro Val Cys Lys Asp Ser Thr Arg Ile Arg Ile Thr Asp Asn Met Phe
                485                 490                 495

Cys Ala Gly Tyr Lys Pro Asp Glu Gly Lys Arg Gly Asp Ala Cys Glu
            500                 505                 510

Gly Asp Ser Gly Gly Pro Phe Val Met Lys Ser Pro Phe Asn Asn Arg
        515                 520                 525

Trp Tyr Gln Met Gly Ile Val Ser Trp Gly Glu Gly Cys Asp Arg Asp
    530                 535                 540

Gly Lys Tyr Gly Phe Tyr Thr His Val Phe Arg Leu Lys Lys Trp Ile
545                 550                 555                 560

Gln Lys Val Ile Asp Gln Phe Gly Glu
                565

<210> SEQ ID NO 10
<211> LENGTH: 36
<212> TYPE: DNA
<213> ORGANISM: Artificial Sequence
<220> FEATURE:
<223> OTHER INFORMATION: Synthetic

<400> SEQUENCE: 10
gttggtaagg ggcagcccgt ggagcggccg gtctgc                               36

<210> SEQ ID NO 11
<211> LENGTH: 36
<212> TYPE: DNA
<213> ORGANISM: Artificial Sequence
<220> FEATURE:
<223> OTHER INFORMATION: Synthetic

<400> SEQUENCE: 11
gcagaccggc cgctccacgg gctgcccctt accaac                               36

<210> SEQ ID NO 12
<211> LENGTH: 574
<212> TYPE: PRT
<213> ORGANISM: Artificial Sequence
<220> FEATURE:
<223> OTHER INFORMATION: Synthetic

<400> SEQUENCE: 12

Ala Asn Thr Phe Leu Glu Glu Val Arg Lys Gly Asn Leu Glu Arg Glu
1               5                   10                  15

Cys Val Glu Glu Thr Cys Ser Tyr Glu Glu Ala Phe Glu Ala Leu Glu
            20                  25                  30

Ser Ser Thr Ala Thr Asp Val Phe Trp Ala Lys Tyr Thr Ala Cys Glu
```

```
            35                  40                  45
Thr Ala Arg Thr Pro Arg Asp Lys Leu Ala Ala Cys Leu Glu Gly Asn
            50                  55                  60
Cys Ala Glu Gly Leu Gly Thr Asn Tyr Arg Gly His Val Asn Ile Thr
 65                  70                  75                  80
Arg Ser Gly Ile Glu Cys Gln Leu Trp Arg Ser Arg Tyr Pro His Lys
                 85                  90                  95
Pro Glu Ile Asn Ser Thr Thr His Pro Gly Ala Asp Leu Gln Glu Asn
                100                 105                 110
Phe Cys Arg Asn Pro Asp Ser Ser Thr Thr Gly Pro Trp Cys Tyr Thr
            115                 120                 125
Thr Asp Pro Thr Val Arg Arg Gln Glu Cys Ser Ile Pro Val Cys Gly
        130                 135                 140
Gln Asp Gln Val Thr Val Ala Met Thr Pro Arg Ser Glu Gly Ser Ser
145                 150                 155                 160
Val Asn Leu Ser Pro Pro Leu Glu Gln Cys Val Pro Asp Arg Gly Gln
                165                 170                 175
Gln Tyr Gln Gly Arg Leu Ala Val Thr Thr His Gly Leu Pro Cys Leu
            180                 185                 190
Ala Trp Ala Ser Ala Gln Ala Lys Ala Leu Ser Lys His Gln Asp Phe
        195                 200                 205
Asn Ser Ala Val Gln Leu Val Glu Asn Phe Cys Arg Asn Pro Asp Gly
210                 215                 220
Asp Glu Glu Gly Val Trp Cys Tyr Val Ala Gly Lys Pro Gly Asp Phe
225                 230                 235                 240
Gly Tyr Cys Asp Leu Asn Tyr Cys Glu Glu Ala Val Glu Glu Glu Thr
                245                 250                 255
Gly Asp Gly Leu Asp Glu Asp Ser Asp Arg Ala Ile Glu Gly Arg Thr
            260                 265                 270
Ala Thr Ser Glu Tyr Gln Thr Phe Phe Asn Pro Arg Thr Phe Gly Ser
        275                 280                 285
Gly Glu Ala Asp Cys Gly Leu Arg Pro Leu Phe Glu Lys Lys Ser Leu
    290                 295                 300
Glu Asp Lys Thr Glu Arg Glu Leu Leu Glu Ser Tyr Ile Asp Gly Arg
305                 310                 315                 320
Ile Val Glu Gly Ser Asp Ala Glu Ile Gly Met Ser Pro Trp Gln Val
                325                 330                 335
Met Leu Phe Arg Lys Ser Pro Gln Glu Leu Leu Cys Gly Ala Ser Leu
            340                 345                 350
Ile Ser Asp Arg Trp Val Leu Thr Ala Ala His Cys Leu Leu Tyr Pro
        355                 360                 365
Pro Trp Asp Lys Asn Phe Thr Glu Asn Asp Leu Leu Val Arg Ile Gly
    370                 375                 380
Lys His Ser Arg Thr Arg Tyr Glu Arg Asn Ile Glu Lys Ile Ser Met
385                 390                 395                 400
Leu Glu Lys Ile Tyr Ile His Pro Arg Tyr Asn Trp Arg Glu Asn Leu
                405                 410                 415
Asp Arg Asp Ile Ala Leu Met Lys Leu Lys Lys Pro Val Ala Phe Ser
            420                 425                 430
Asp Tyr Ile His Pro Val Cys Leu Pro Asp Arg Glu Thr Ala Ala Ser
        435                 440                 445
Leu Leu Gln Ala Gly Tyr Lys Gly Arg Val Thr Gly Trp Gly Asn Leu
    450                 455                 460
```

```
Lys Glu Thr Trp Thr Ala Asn Val Gly Lys Gly Gln Pro Val Asn Leu
465                 470                 475                 480

Pro Ile Val Glu Arg Pro Val Cys Lys Asp Ser Thr Arg Ile Arg Ile
            485                 490                 495

Thr Asp Asn Met Phe Cys Ala Gly Tyr Lys Pro Asp Glu Gly Lys Arg
        500                 505                 510

Gly Asp Ala Cys Glu Gly Asp Ser Gly Gly Pro Phe Val Met Lys Ser
        515                 520                 525

Pro Phe Asn Asn Arg Trp Tyr Gln Met Gly Ile Val Ser Trp Gly Glu
    530                 535                 540

Gly Cys Asp Arg Asp Gly Lys Tyr Gly Phe Tyr Thr His Val Phe Arg
545                 550                 555                 560

Leu Lys Lys Trp Ile Gln Lys Val Ile Asp Gln Phe Gly Glu
                565                 570
```

<210> SEQ ID NO 13
<211> LENGTH: 36
<212> TYPE: DNA
<213> ORGANISM: Artificial Sequence
<220> FEATURE:
<223> OTHER INFORMATION: Synthetic

<400> SEQUENCE: 13
gttggtaagg ggcagcccgt gaacctgccc attgtg                       36

<210> SEQ ID NO 14
<211> LENGTH: 36
<212> TYPE: DNA
<213> ORGANISM: Artificial Sequence
<220> FEATURE:
<223> OTHER INFORMATION: Synthetic

<400> SEQUENCE: 14
cacaatgggc aggttcacgg gctgcccctt accaac                       36

<210> SEQ ID NO 15
<211> LENGTH: 579
<212> TYPE: PRT
<213> ORGANISM: Artificial Sequence
<220> FEATURE:
<223> OTHER INFORMATION: Synthetic

<400> SEQUENCE: 15

```
Ala Asn Thr Phe Leu Glu Glu Val Arg Lys Gly Asn Leu Glu Arg Glu
1               5                   10                  15

Cys Val Glu Glu Thr Cys Ser Tyr Glu Glu Ala Phe Glu Ala Leu Glu
            20                  25                  30

Ser Ser Thr Ala Thr Asp Val Phe Trp Ala Lys Tyr Thr Ala Cys Glu
        35                  40                  45

Thr Ala Arg Thr Pro Arg Asp Lys Leu Ala Ala Cys Leu Glu Gly Asn
    50                  55                  60

Cys Ala Glu Gly Leu Gly Thr Asn Tyr Arg Gly His Val Asn Ile Thr
65                  70                  75                  80

Arg Ser Gly Ile Glu Cys Gln Leu Trp Arg Ser Arg Tyr Pro His Lys
                85                  90                  95

Pro Glu Ile Asn Ser Thr Thr His Pro Gly Ala Asp Leu Gln Glu Asn
            100                 105                 110

Phe Cys Arg Asn Pro Asp Ser Ser Thr Thr Gly Pro Trp Cys Tyr Thr
        115                 120                 125
```

```
Thr Asp Pro Thr Val Arg Arg Gln Glu Cys Ser Ile Pro Val Cys Gly
    130                 135                 140

Gln Asp Gln Val Thr Val Ala Met Thr Pro Arg Ser Glu Gly Ser Ser
145                 150                 155                 160

Val Asn Leu Ser Pro Pro Leu Glu Gln Cys Val Pro Asp Arg Gly Gln
                165                 170                 175

Gln Tyr Gln Gly Arg Leu Ala Val Thr Thr His Gly Leu Pro Cys Leu
            180                 185                 190

Ala Trp Ala Ser Ala Gln Ala Lys Ala Leu Ser Lys His Gln Asp Phe
        195                 200                 205

Asn Ser Ala Val Gln Leu Val Glu Asn Phe Cys Arg Asn Pro Asp Gly
210                 215                 220

Asp Glu Glu Gly Val Trp Cys Tyr Val Ala Gly Lys Pro Gly Asp Phe
225                 230                 235                 240

Gly Tyr Cys Asp Leu Asn Tyr Cys Glu Glu Ala Val Glu Glu Glu Thr
                245                 250                 255

Gly Asp Gly Leu Asp Glu Asp Ser Asp Arg Ala Ile Glu Gly Arg Thr
            260                 265                 270

Ala Thr Ser Glu Tyr Gln Thr Phe Phe Asn Pro Arg Thr Phe Gly Ser
        275                 280                 285

Gly Glu Ala Asp Cys Gly Leu Arg Pro Leu Phe Glu Lys Lys Ser Leu
290                 295                 300

Glu Asp Lys Thr Glu Arg Glu Leu Leu Glu Ser Tyr Ile Asp Gly Arg
305                 310                 315                 320

Ile Val Glu Gly Ser Asp Ala Glu Ile Gly Met Ser Pro Trp Gln Val
                325                 330                 335

Met Leu Phe Arg Lys Ser Pro Gln Glu Leu Leu Cys Gly Ala Ser Leu
            340                 345                 350

Ile Ser Asp Arg Trp Val Leu Thr Ala Ala His Cys Leu Leu Tyr Pro
        355                 360                 365

Pro Trp Asp Lys Asn Phe Thr Glu Asn Asp Leu Leu Val Arg Ile Gly
370                 375                 380

Lys His Ser Arg Thr Arg Tyr Glu Arg Asn Ile Glu Lys Ile Ser Met
385                 390                 395                 400

Leu Glu Lys Ile Tyr Ile His Pro Arg Tyr Asn Trp Arg Glu Asn Leu
                405                 410                 415

Asp Arg Asp Ile Ala Leu Met Lys Leu Lys Lys Pro Val Ala Phe Ser
            420                 425                 430

Asp Tyr Ile His Pro Val Cys Leu Pro Asp Arg Glu Thr Ala Ala Ser
        435                 440                 445

Leu Leu Gln Ala Gly Tyr Lys Gly Arg Val Thr Gly Trp Gly Asn Leu
450                 455                 460

Lys Glu Thr Trp Thr Ala Asn Val Gly Lys Gly Gln Pro Ala Val Leu
465                 470                 475                 480

Gln Val Val Asn Leu Pro Ile Val Glu Arg Pro Val Cys Lys Asp Ser
                485                 490                 495

Thr Arg Ile Arg Ile Thr Asp Asn Met Phe Cys Ala Gly Tyr Lys Pro
            500                 505                 510

Asp Glu Gly Lys Arg Gly Asp Ala Cys Glu Gly Asp Ser Gly Gly Pro
        515                 520                 525

Phe Val Met Lys Ser Pro Phe Asn Asn Arg Trp Tyr Gln Met Gly Ile
530                 535                 540
```

```
Val Ser Trp Gly Glu Gly Cys Asp Arg Asp Gly Lys Tyr Gly Phe Tyr
545                 550                 555                 560

Thr His Val Phe Arg Leu Lys Lys Trp Ile Gln Lys Val Ile Asp Gln
                565                 570                 575

Phe Gly Glu

<210> SEQ ID NO 16
<211> LENGTH: 30
<212> TYPE: DNA
<213> ORGANISM: Artificial Sequence
<220> FEATURE:
<223> OTHER INFORMATION: synthetic

<400> SEQUENCE: 16
ggtaaggggc agcccgcagt cctgcaggtg                                              30

<210> SEQ ID NO 17
<211> LENGTH: 30
<212> TYPE: DNA
<213> ORGANISM: Artificial sequence
<220> FEATURE:
<223> OTHER INFORMATION: synthetic

<400> SEQUENCE: 17
cacctgcagg actgcgggct gccccttacc                                              30

<210> SEQ ID NO 18
<211> LENGTH: 579
<212> TYPE: PRT
<213> ORGANISM: Artificial sequence
<220> FEATURE:
<223> OTHER INFORMATION: synthetic

<400> SEQUENCE: 18

Ala Asn Thr Phe Leu Glu Glu Val Arg Lys Gly Asn Leu Glu Arg Glu
1               5                   10                  15

Cys Val Glu Glu Thr Cys Ser Tyr Glu Glu Ala Phe Glu Ala Leu Glu
                20                  25                  30

Ser Ser Thr Ala Thr Asp Val Phe Trp Ala Lys Tyr Thr Ala Cys Glu
            35                  40                  45

Thr Ala Arg Thr Pro Arg Asp Lys Leu Ala Ala Cys Leu Glu Gly Asn
        50                  55                  60

Cys Ala Glu Gly Leu Gly Thr Asn Tyr Arg Gly His Val Asn Ile Thr
65                  70                  75                  80

Arg Ser Gly Ile Glu Cys Gln Leu Trp Arg Ser Arg Tyr Pro His Lys
                85                  90                  95

Pro Glu Ile Asn Ser Thr Thr His Pro Gly Ala Asp Leu Gln Glu Asn
                100                 105                 110

Phe Cys Arg Asn Pro Asp Ser Ser Thr Thr Gly Pro Trp Cys Tyr Thr
            115                 120                 125

Thr Asp Pro Thr Val Arg Arg Gln Glu Cys Ser Ile Pro Val Cys Gly
        130                 135                 140

Gln Asp Gln Val Thr Val Ala Met Thr Pro Arg Ser Glu Gly Ser Ser
145                 150                 155                 160

Val Asn Leu Ser Pro Pro Leu Glu Gln Cys Val Pro Asp Arg Gly Gln
                165                 170                 175

Gln Tyr Gln Gly Arg Leu Ala Val Thr Thr His Gly Leu Pro Cys Leu
            180                 185                 190

Ala Trp Ala Ser Ala Gln Ala Lys Ala Leu Ser Lys His Gln Asp Phe
```

```
            195                 200                 205
Asn Ser Ala Val Gln Leu Val Glu Asn Phe Cys Arg Asn Pro Asp Gly
210                 215                 220

Asp Glu Glu Gly Val Trp Cys Tyr Val Ala Gly Lys Pro Gly Asp Phe
225                 230                 235                 240

Gly Tyr Cys Asp Leu Asn Tyr Cys Glu Glu Ala Val Glu Glu Glu Thr
                245                 250                 255

Gly Asp Gly Leu Asp Glu Asp Ser Asp Arg Ala Ile Glu Gly Arg Thr
                260                 265                 270

Ala Thr Ser Glu Tyr Gln Thr Phe Phe Asn Pro Arg Thr Phe Gly Ser
            275                 280                 285

Gly Glu Ala Asp Cys Gly Leu Arg Pro Leu Phe Glu Lys Lys Ser Leu
        290                 295                 300

Glu Asp Lys Thr Glu Arg Glu Leu Leu Glu Ser Tyr Ile Asp Gly Arg
305                 310                 315                 320

Ile Val Glu Gly Ser Asp Ala Glu Ile Gly Met Ser Pro Trp Gln Val
                325                 330                 335

Met Leu Phe Arg Lys Ser Pro Gln Glu Leu Leu Cys Gly Ala Ser Leu
                340                 345                 350

Ile Ser Asp Arg Trp Val Leu Thr Ala Ala His Cys Leu Leu Tyr Pro
            355                 360                 365

Pro Trp Asp Lys Asn Phe Thr Glu Asn Asp Leu Leu Val Arg Ile Gly
        370                 375                 380

Lys His Ser Arg Thr Arg Tyr Glu Arg Asn Ile Glu Lys Ile Ser Met
385                 390                 395                 400

Leu Glu Lys Ile Tyr Ile His Pro Arg Tyr Asn Trp Arg Glu Asn Leu
                405                 410                 415

Asp Arg Asp Ile Ala Leu Met Lys Leu Lys Lys Pro Val Ala Phe Ser
                420                 425                 430

Asp Tyr Ile His Pro Val Cys Leu Pro Asp Arg Glu Thr Ala Ala Ser
            435                 440                 445

Leu Leu Gln Ala Gly Tyr Lys Gly Arg Val Thr Gly Trp Gly Asn Leu
        450                 455                 460

Lys Glu Thr Trp Thr Ala Asn Val Gly Lys Gly Gln Pro Ser Val Ala
465                 470                 475                 480

Gln Val Val Asn Leu Pro Ile Val Glu Arg Pro Val Cys Lys Asp Ser
                485                 490                 495

Thr Arg Ile Arg Ile Thr Asp Asn Met Phe Cys Ala Gly Tyr Lys Pro
                500                 505                 510

Asp Glu Gly Lys Arg Gly Asp Ala Cys Glu Gly Asp Ser Gly Gly Pro
            515                 520                 525

Phe Val Met Lys Ser Pro Phe Asn Asn Arg Trp Tyr Gln Met Gly Ile
        530                 535                 540

Val Ser Trp Gly Glu Gly Cys Asp Arg Asp Gly Lys Tyr Gly Phe Tyr
545                 550                 555                 560

Thr His Val Phe Arg Leu Lys Lys Trp Ile Gln Lys Val Ile Asp Gln
                565                 570                 575

Phe Gly Glu

<210> SEQ ID NO 19
<211> LENGTH: 36
<212> TYPE: DNA
<213> ORGANISM: Artificial Sequence
<220> FEATURE:
```

-continued

<223> OTHER INFORMATION: synthetic

<400> SEQUENCE: 19
gggcagccca gtgtcgcgca ggtggtgaac ctgccc         36

<210> SEQ ID NO 20
<211> LENGTH: 36
<212> TYPE: DNA
<213> ORGANISM: Artificial sequence
<220> FEATURE:
<223> OTHER INFORMATION: synthetic

<400> SEQUENCE: 20
gggcaggttc accacctgcg cgacactggg ctgccc         36

<210> SEQ ID NO 21
<211> LENGTH: 579
<212> TYPE: PRT
<213> ORGANISM: artificial sequence
<220> FEATURE:
<223> OTHER INFORMATION: synthetic

<400> SEQUENCE: 21

```
Ala Asn Thr Phe Leu Glu Glu Val Arg Lys Gly Asn Leu Glu Arg Glu
1               5                   10                  15

Cys Val Glu Glu Thr Cys Ser Tyr Glu Glu Ala Phe Glu Ala Leu Glu
            20                  25                  30

Ser Ser Thr Ala Thr Asp Val Phe Trp Ala Lys Tyr Thr Ala Cys Glu
        35                  40                  45

Thr Ala Arg Thr Pro Arg Asp Lys Leu Ala Ala Cys Leu Glu Gly Asn
    50                  55                  60

Cys Ala Glu Gly Leu Gly Thr Asn Tyr Arg Gly His Val Asn Ile Thr
65                  70                  75                  80

Arg Ser Gly Ile Glu Cys Gln Leu Trp Arg Ser Arg Tyr Pro His Lys
                85                  90                  95

Pro Glu Ile Asn Ser Thr Thr His Pro Gly Ala Asp Leu Gln Glu Asn
            100                 105                 110

Phe Cys Arg Asn Pro Asp Ser Ser Thr Thr Gly Pro Trp Cys Tyr Thr
        115                 120                 125

Thr Asp Pro Thr Val Arg Arg Gln Glu Cys Ser Ile Pro Val Cys Gly
    130                 135                 140

Gln Asp Gln Val Thr Val Ala Met Thr Pro Arg Ser Glu Gly Ser Ser
145                 150                 155                 160

Val Asn Leu Ser Pro Pro Leu Glu Gln Cys Val Pro Asp Arg Gly Gln
                165                 170                 175

Gln Tyr Gln Gly Arg Leu Ala Val Thr Thr His Gly Leu Pro Cys Leu
            180                 185                 190

Ala Trp Ala Ser Ala Gln Ala Lys Ala Leu Ser Lys His Gln Asp Phe
        195                 200                 205

Asn Ser Ala Val Gln Leu Val Glu Asn Phe Cys Arg Asn Pro Asp Gly
    210                 215                 220

Asp Glu Glu Gly Val Trp Cys Tyr Val Ala Gly Lys Pro Gly Asp Phe
225                 230                 235                 240

Gly Tyr Cys Asp Leu Asn Tyr Cys Glu Glu Ala Val Glu Glu Glu Thr
                245                 250                 255

Gly Asp Gly Leu Asp Glu Asp Ser Asp Arg Ala Ile Glu Gly Arg Thr
            260                 265                 270
```

```
Ala Thr Ser Glu Tyr Gln Thr Phe Phe Asn Pro Arg Thr Phe Gly Ser
            275                 280                 285

Gly Glu Ala Asp Cys Gly Leu Arg Pro Leu Phe Glu Lys Lys Ser Leu
        290                 295                 300

Glu Asp Lys Thr Glu Arg Glu Leu Leu Glu Ser Tyr Ile Asp Gly Arg
305                 310                 315                 320

Ile Val Glu Gly Ser Asp Ala Glu Ile Gly Met Ser Pro Trp Gln Val
                325                 330                 335

Met Leu Phe Arg Lys Ser Pro Gln Glu Leu Leu Cys Gly Ala Ser Leu
            340                 345                 350

Ile Ser Asp Arg Trp Val Leu Thr Ala Ala His Cys Leu Leu Tyr Pro
        355                 360                 365

Pro Trp Asp Lys Asn Phe Thr Glu Asn Asp Leu Leu Val Arg Ile Gly
370                 375                 380

Lys His Ser Arg Thr Arg Tyr Glu Arg Asn Ile Glu Lys Ile Ser Met
385                 390                 395                 400

Leu Glu Lys Ile Tyr Ile His Pro Arg Tyr Asn Trp Arg Glu Asn Leu
                405                 410                 415

Asp Arg Asp Ile Ala Leu Met Lys Leu Lys Lys Pro Val Ala Phe Ser
            420                 425                 430

Asp Tyr Ile His Pro Val Cys Leu Pro Asp Arg Glu Thr Ala Ala Ser
        435                 440                 445

Leu Leu Gln Ala Gly Tyr Lys Gly Arg Val Thr Gly Trp Gly Asn Leu
    450                 455                 460

Lys Glu Thr Trp Thr Ala Asn Val Gly Lys Gly Gln Pro Ala Val Ala
465                 470                 475                 480

Gln Val Val Asn Leu Pro Ile Val Glu Arg Pro Val Cys Lys Asp Ser
                485                 490                 495

Thr Arg Ile Arg Ile Thr Asp Asn Met Phe Cys Ala Gly Tyr Lys Pro
            500                 505                 510

Asp Glu Gly Lys Arg Gly Asp Ala Cys Glu Gly Asp Ser Gly Gly Pro
        515                 520                 525

Phe Val Met Lys Ser Pro Phe Asn Asn Arg Trp Tyr Gln Met Gly Ile
    530                 535                 540

Val Ser Trp Gly Glu Gly Cys Asp Arg Asp Gly Lys Tyr Gly Phe Tyr
545                 550                 555                 560

Thr His Val Phe Arg Leu Lys Lys Trp Ile Gln Lys Val Ile Asp Gln
                565                 570                 575

Phe Gly Glu

<210> SEQ ID NO 22
<211> LENGTH: 39
<212> TYPE: DNA
<213> ORGANISM: Artificial sequence
<220> FEATURE:
<223> OTHER INFORMATION: synthetic

<400> SEQUENCE: 22
ggtaaggggc agcccgcagt cgcgcaggtg gtgaacctg                              39

<210> SEQ ID NO 23
<211> LENGTH: 39
<212> TYPE: DNA
<213> ORGANISM: Artificial sequence
<220> FEATURE:
<223> OTHER INFORMATION: synthetic
```

<400> SEQUENCE: 23
caggttcacc acctgcgcca ctgcgggctg ccccttacc        39

<210> SEQ ID NO 24
<211> LENGTH: 579
<212> TYPE: PRT
<213> ORGANISM: Artificial sequence
<220> FEATURE:
<223> OTHER INFORMATION: synthetic

<400> SEQUENCE: 24

```
Ala Asn Thr Phe Leu Glu Glu Val Arg Lys Gly Asn Leu Glu Arg Glu
1               5                   10                  15

Cys Val Glu Glu Thr Cys Ser Tyr Glu Glu Ala Phe Glu Ala Leu Glu
            20                  25                  30

Ser Ser Thr Ala Thr Asp Val Phe Trp Ala Lys Tyr Thr Ala Cys Glu
        35                  40                  45

Thr Ala Arg Thr Pro Arg Asp Lys Leu Ala Ala Cys Leu Glu Gly Asn
    50                  55                  60

Cys Ala Glu Gly Leu Gly Thr Asn Tyr Arg Gly His Val Asn Ile Thr
65                  70                  75                  80

Arg Ser Gly Ile Glu Cys Gln Leu Trp Arg Ser Arg Tyr Pro His Lys
                85                  90                  95

Pro Glu Ile Asn Ser Thr Thr His Pro Gly Ala Asp Leu Gln Glu Asn
            100                 105                 110

Phe Cys Arg Asn Pro Asp Ser Ser Thr Thr Gly Pro Trp Cys Tyr Thr
        115                 120                 125

Thr Asp Pro Thr Val Arg Arg Gln Glu Cys Ser Ile Pro Val Cys Gly
    130                 135                 140

Gln Asp Gln Val Thr Val Ala Met Thr Pro Arg Ser Glu Gly Ser Ser
145                 150                 155                 160

Val Asn Leu Ser Pro Pro Leu Glu Gln Cys Val Pro Asp Arg Gly Gln
                165                 170                 175

Gln Tyr Gln Gly Arg Leu Ala Val Thr Thr His Gly Leu Pro Cys Leu
            180                 185                 190

Ala Trp Ala Ser Ala Gln Ala Lys Ala Leu Ser Lys His Gln Asp Phe
        195                 200                 205

Asn Ser Ala Val Gln Leu Val Glu Asn Phe Cys Arg Asn Pro Asp Gly
    210                 215                 220

Asp Glu Glu Gly Val Trp Cys Tyr Val Ala Gly Lys Pro Gly Asp Phe
225                 230                 235                 240

Gly Tyr Cys Asp Leu Asn Tyr Cys Glu Glu Ala Val Glu Glu Glu Thr
                245                 250                 255

Gly Asp Gly Leu Asp Glu Asp Ser Asp Arg Ala Ile Glu Gly Arg Thr
            260                 265                 270

Ala Thr Ser Glu Tyr Gln Thr Phe Phe Asn Pro Arg Thr Phe Gly Ser
        275                 280                 285

Gly Glu Ala Asp Cys Gly Leu Arg Pro Leu Phe Glu Lys Lys Ser Leu
    290                 295                 300

Glu Asp Lys Thr Glu Arg Glu Leu Leu Glu Ser Tyr Ile Asp Gly Arg
305                 310                 315                 320

Ile Val Glu Gly Ser Asp Ala Glu Ile Gly Met Ser Pro Trp Gln Val
                325                 330                 335

Met Leu Phe Arg Lys Ser Pro Gln Glu Leu Leu Cys Gly Ala Ser Leu
            340                 345                 350
```

Ile Ser Asp Arg Trp Val Leu Thr Ala Ala His Cys Leu Leu Tyr Pro
        355                 360                 365

Pro Trp Asp Lys Asn Phe Thr Glu Asn Asp Leu Leu Val Arg Ile Gly
370                 375                 380

Lys His Ser Arg Thr Arg Tyr Glu Arg Asn Ile Glu Lys Ile Ser Met
385                 390                 395                 400

Leu Glu Lys Ile Tyr Ile His Pro Arg Tyr Asn Trp Arg Glu Asn Leu
                405                 410                 415

Asp Arg Asp Ile Ala Leu Met Lys Leu Lys Pro Val Ala Phe Ser
            420                 425                 430

Asp Tyr Ile His Pro Val Cys Leu Pro Asp Arg Glu Thr Ala Ala Ser
                435                 440                 445

Leu Leu Gln Ala Gly Tyr Lys Gly Arg Val Thr Gly Trp Gly Asn Leu
        450                 455                 460

Lys Glu Thr Trp Thr Ala Asn Val Gly Lys Gly Gln Pro Ala Val Leu
465                 470                 475                 480

Ala Val Val Asn Leu Pro Ile Val Glu Arg Pro Val Cys Lys Asp Ser
                485                 490                 495

Thr Arg Ile Arg Ile Thr Asp Asn Met Phe Cys Ala Gly Tyr Lys Pro
            500                 505                 510

Asp Glu Gly Lys Arg Gly Asp Ala Cys Glu Gly Asp Ser Gly Gly Pro
        515                 520                 525

Phe Val Met Lys Ser Pro Phe Asn Asn Arg Trp Tyr Gln Met Gly Ile
530                 535                 540

Val Ser Trp Gly Glu Gly Cys Asp Arg Asp Gly Lys Tyr Gly Phe Tyr
545                 550                 555                 560

Thr His Val Phe Arg Leu Lys Lys Trp Ile Gln Lys Val Ile Asp Gln
                565                 570                 575

Phe Gly Glu

<210> SEQ ID NO 25
<211> LENGTH: 39
<212> TYPE: DNA
<213> ORGANISM: Artificial sequence
<220> FEATURE:
<223> OTHER INFORMATION: synthetic

<400> SEQUENCE: 25
ggtaaggggc agcccgcagt cctggcggtg gtgaacctg                              39

<210> SEQ ID NO 26
<211> LENGTH: 39
<212> TYPE: DNA
<213> ORGANISM: Artificial sequence
<220> FEATURE:
<223> OTHER INFORMATION: synthetic

<400> SEQUENCE: 26
caggttcacc accgccagga ctgcgggctg ccccttacc                              39

<210> SEQ ID NO 27
<211> LENGTH: 579
<212> TYPE: PRT
<213> ORGANISM: Artificial sequence
<220> FEATURE:
<223> OTHER INFORMATION: synthetic

<400> SEQUENCE: 27

```
Ala Asn Thr Phe Leu Glu Glu Val Arg Lys Gly Asn Leu Glu Arg Glu
 1               5                  10                  15

Cys Val Glu Glu Thr Cys Ser Tyr Glu Glu Ala Phe Glu Ala Leu Glu
             20                  25                  30

Ser Ser Thr Ala Thr Asp Val Phe Trp Ala Lys Tyr Thr Ala Cys Glu
             35                  40                  45

Thr Ala Arg Thr Pro Arg Asp Lys Leu Ala Ala Cys Leu Glu Gly Asn
         50                  55                  60

Cys Ala Glu Gly Leu Gly Thr Asn Tyr Arg Gly His Val Asn Ile Thr
 65                  70                  75                  80

Arg Ser Gly Ile Glu Cys Gln Leu Trp Arg Ser Arg Tyr Pro His Lys
                 85                  90                  95

Pro Glu Ile Asn Ser Thr Thr His Pro Gly Ala Asp Leu Gln Glu Asn
            100                 105                 110

Phe Cys Arg Asn Pro Asp Ser Ser Thr Thr Gly Pro Trp Cys Tyr Thr
        115                 120                 125

Thr Asp Pro Thr Val Arg Arg Gln Glu Cys Ser Ile Pro Val Cys Gly
    130                 135                 140

Gln Asp Gln Val Thr Val Ala Met Thr Pro Arg Ser Glu Gly Ser Ser
145                 150                 155                 160

Val Asn Leu Ser Pro Pro Leu Glu Gln Cys Val Pro Asp Arg Gly Gln
                165                 170                 175

Gln Tyr Gln Gly Arg Leu Ala Val Thr Thr His Gly Leu Pro Cys Leu
            180                 185                 190

Ala Trp Ala Ser Ala Gln Ala Lys Ala Leu Ser Lys His Gln Asp Phe
        195                 200                 205

Asn Ser Ala Val Gln Leu Val Glu Asn Phe Cys Arg Asn Pro Asp Gly
    210                 215                 220

Asp Glu Glu Gly Val Trp Cys Tyr Val Ala Gly Lys Pro Gly Asp Phe
225                 230                 235                 240

Gly Tyr Cys Asp Leu Asn Tyr Cys Glu Glu Ala Val Glu Glu Glu Thr
                245                 250                 255

Gly Asp Gly Leu Asp Glu Asp Ser Asp Arg Ala Ile Glu Gly Arg Thr
            260                 265                 270

Ala Thr Ser Glu Tyr Gln Thr Phe Phe Asn Pro Arg Thr Phe Gly Ser
        275                 280                 285

Gly Glu Ala Asp Cys Gly Leu Arg Pro Leu Phe Glu Lys Lys Ser Leu
    290                 295                 300

Glu Asp Lys Thr Glu Arg Glu Leu Leu Glu Ser Tyr Ile Asp Gly Arg
305                 310                 315                 320

Ile Val Glu Gly Ser Asp Ala Glu Ile Gly Met Ser Pro Trp Gln Val
                325                 330                 335

Met Leu Phe Arg Lys Ser Pro Gln Glu Leu Leu Cys Gly Ala Ser Leu
            340                 345                 350

Ile Ser Asp Arg Trp Val Leu Thr Ala Ala His Cys Leu Leu Tyr Pro
        355                 360                 365

Pro Trp Asp Lys Asn Phe Thr Glu Asn Asp Leu Leu Val Arg Ile Gly
    370                 375                 380

Lys His Ser Arg Thr Arg Tyr Glu Arg Asn Ile Glu Lys Ile Ser Met
385                 390                 395                 400

Leu Glu Lys Ile Tyr Ile His Pro Arg Tyr Asn Trp Arg Glu Asn Leu
                405                 410                 415

Asp Arg Asp Ile Ala Leu Met Lys Leu Lys Lys Pro Val Ala Phe Ser
```

```
                420             425             430
Asp Tyr Ile His Pro Val Cys Leu Pro Asp Arg Glu Thr Ala Ala Ser
                435                 440                 445

Leu Leu Gln Ala Gly Tyr Lys Gly Arg Val Thr Gly Trp Gly Asn Leu
        450                 455                 460

Lys Glu Thr Trp Thr Ala Asn Val Gly Lys Gly Gln Pro Ala Val Ala
465                 470                 475                 480

Ala Val Val Asn Leu Pro Ile Val Glu Arg Pro Val Cys Lys Asp Ser
                485                 490                 495

Thr Arg Ile Arg Ile Thr Asp Asn Met Phe Cys Ala Gly Tyr Lys Pro
        500                 505                 510

Asp Glu Gly Lys Arg Gly Asp Ala Cys Glu Gly Asp Ser Gly Gly Pro
            515                 520                 525

Phe Val Met Lys Ser Pro Phe Asn Asn Arg Trp Tyr Gln Met Gly Ile
        530                 535                 540

Val Ser Trp Gly Glu Gly Cys Asp Arg Asp Gly Lys Tyr Gly Phe Tyr
545                 550                 555                 560

Thr His Val Phe Arg Leu Lys Lys Trp Ile Gln Lys Val Ile Asp Gln
                565                 570                 575

Phe Gly Glu

<210> SEQ ID NO 28
<211> LENGTH: 39
<212> TYPE: DNA
<213> ORGANISM: Artificial sequence
<220> FEATURE:
<223> OTHER INFORMATION: synthetic

<400> SEQUENCE: 28
ggtaaggggc agcccgcagt cgcggcggtg gtgaacctg                        39

<210> SEQ ID NO 29
<211> LENGTH: 39
<212> TYPE: DNA
<213> ORGANISM: Artificial sequence
<220> FEATURE:
<223> OTHER INFORMATION: synthetic

<400> SEQUENCE: 29
caggttcacc accgccgcga ctgcgggctg cccttacc                         39

<210> SEQ ID NO 30
<211> LENGTH: 576
<212> TYPE: PRT
<213> ORGANISM: Artificial sequence
<220> FEATURE:
<223> OTHER INFORMATION: synthetic

<400> SEQUENCE: 30

Ala Asn Thr Phe Leu Glu Glu Val Arg Lys Gly Asn Leu Glu Arg Glu
1               5                   10                  15

Cys Val Glu Glu Thr Cys Ser Tyr Glu Glu Ala Phe Glu Ala Leu Glu
            20                  25                  30

Ser Ser Thr Ala Thr Asp Val Phe Trp Ala Lys Tyr Thr Ala Cys Glu
        35                  40                  45

Thr Ala Arg Thr Pro Arg Asp Lys Leu Ala Ala Cys Leu Glu Gly Asn
    50                  55                  60

Cys Ala Glu Gly Leu Gly Thr Asn Tyr Arg Gly His Val Asn Ile Thr
65                  70                  75                  80
```

```
Arg Ser Gly Ile Glu Cys Gln Leu Trp Arg Ser Arg Tyr Pro His Lys
                85                  90                  95
Pro Glu Ile Asn Ser Thr Thr His Pro Gly Ala Asp Leu Gln Glu Asn
            100                 105                 110
Phe Cys Arg Asn Pro Asp Ser Ser Thr Thr Gly Pro Trp Cys Tyr Thr
        115                 120                 125
Thr Asp Pro Thr Val Arg Arg Gln Glu Cys Ser Ile Pro Val Cys Gly
130                 135                 140
Gln Asp Gln Val Thr Val Ala Met Thr Pro Arg Ser Glu Gly Ser Ser
145                 150                 155                 160
Val Asn Leu Ser Pro Pro Leu Glu Gln Cys Val Pro Asp Arg Gly Gln
                165                 170                 175
Gln Tyr Gln Gly Arg Leu Ala Val Thr Thr His Gly Leu Pro Cys Leu
            180                 185                 190
Ala Trp Ala Ser Ala Gln Ala Lys Ala Leu Ser Lys His Gln Asp Phe
        195                 200                 205
Asn Ser Ala Val Gln Leu Val Glu Asn Phe Cys Arg Asn Pro Asp Gly
    210                 215                 220
Asp Glu Glu Gly Val Trp Cys Tyr Val Ala Gly Lys Pro Gly Asp Phe
225                 230                 235                 240
Gly Tyr Cys Asp Leu Asn Tyr Cys Glu Glu Ala Val Glu Glu Glu Thr
                245                 250                 255
Gly Asp Gly Leu Asp Glu Asp Ser Asp Arg Ala Ile Glu Gly Arg Thr
            260                 265                 270
Ala Thr Ser Glu Tyr Gln Thr Phe Phe Asn Pro Arg Thr Phe Gly Ser
        275                 280                 285
Gly Glu Ala Asp Cys Gly Leu Arg Pro Leu Phe Glu Lys Lys Ser Leu
290                 295                 300
Glu Asp Lys Thr Glu Arg Glu Leu Leu Glu Ser Tyr Ile Asp Gly Arg
305                 310                 315                 320
Ile Val Glu Gly Ser Asp Ala Glu Ile Gly Met Ser Pro Trp Gln Val
                325                 330                 335
Met Leu Phe Arg Lys Ser Pro Gln Glu Leu Leu Cys Gly Ala Ser Leu
            340                 345                 350
Ile Ser Asp Arg Trp Val Leu Thr Ala Ala His Cys Leu Leu Tyr Pro
        355                 360                 365
Pro Trp Asp Lys Asn Phe Thr Glu Asn Asp Leu Leu Val Arg Ile Gly
370                 375                 380
Lys His Ser Arg Thr Arg Tyr Glu Arg Asn Ile Glu Lys Ile Ser Met
385                 390                 395                 400
Leu Glu Lys Ile Tyr Ile His Pro Arg Tyr Asn Trp Arg Glu Asn Leu
                405                 410                 415
Asp Arg Asp Ile Ala Leu Met Lys Leu Lys Lys Pro Val Ala Phe Ser
            420                 425                 430
Asp Tyr Ile His Pro Val Cys Leu Pro Asp Arg Glu Thr Ala Ala Ser
        435                 440                 445
Leu Leu Gln Ala Gly Tyr Lys Gly Arg Val Thr Gly Trp Gly Asn Leu
450                 455                 460
Lys Glu Thr Trp Thr Ala Asn Val Gly Lys Gly Gln Pro Val Val Val
465                 470                 475                 480
Asn Leu Pro Ile Val Glu Arg Pro Val Cys Lys Asp Ser Thr Arg Ile
                485                 490                 495
```

```
Arg Ile Thr Asp Asn Met Phe Cys Ala Gly Tyr Lys Pro Asp Glu Gly
                500                 505                 510

Lys Arg Gly Asp Ala Cys Glu Gly Asp Ser Gly Gly Pro Phe Val Met
            515                 520                 525

Lys Ser Pro Phe Asn Asn Arg Trp Tyr Gln Met Gly Ile Val Ser Trp
        530                 535                 540

Gly Glu Gly Cys Asp Arg Asp Gly Lys Tyr Gly Phe Tyr Thr His Val
545                 550                 555                 560

Phe Arg Leu Lys Lys Trp Ile Gln Lys Val Ile Asp Gln Phe Gly Glu
                565                 570                 575
```

<210> SEQ ID NO 31
<211> LENGTH: 33
<212> TYPE: DNA
<213> ORGANISM: Artificial sequence
<220> FEATURE:
<223> OTHER INFORMATION: synthetic

<400> SEQUENCE: 31
ggtaaggggc agcccgtcgt ggtgaacctg ccc                          33

<210> SEQ ID NO 32
<211> LENGTH: 33
<212> TYPE: DNA
<213> ORGANISM: Artificial sequence
<220> FEATURE:
<223> OTHER INFORMATION: synthetic

<400> SEQUENCE: 32
gggcaggttc accacgacgg gctgcccctt acc                          33

<210> SEQ ID NO 33
<211> LENGTH: 564
<212> TYPE: PRT
<213> ORGANISM: Artificial sequence
<220> FEATURE:
<223> OTHER INFORMATION: synthetic

<400> SEQUENCE: 33

```
Ala Asn Thr Phe Leu Glu Glu Val Arg Lys Gly Asn Leu Glu Arg Glu
1               5                   10                  15

Cys Val Glu Glu Thr Cys Ser Tyr Glu Glu Ala Phe Glu Ala Leu Glu
            20                  25                  30

Ser Ser Thr Ala Thr Asp Val Phe Trp Ala Lys Tyr Thr Ala Cys Glu
        35                  40                  45

Thr Ala Arg Thr Pro Arg Asp Lys Leu Ala Ala Cys Leu Glu Gly Asn
    50                  55                  60

Cys Ala Glu Gly Leu Gly Thr Asn Tyr Arg Gly His Val Asn Ile Thr
65                  70                  75                  80

Arg Ser Gly Ile Glu Cys Gln Leu Trp Arg Ser Arg Tyr Pro His Lys
                85                  90                  95

Pro Glu Ile Asn Ser Thr Thr His Pro Gly Ala Asp Leu Gln Glu Asn
            100                 105                 110

Phe Cys Arg Asn Pro Asp Ser Ser Thr Thr Gly Pro Trp Cys Tyr Thr
        115                 120                 125

Thr Asp Pro Thr Val Arg Arg Gln Glu Cys Ser Ile Pro Val Cys Gly
    130                 135                 140

Gln Asp Gln Val Thr Val Ala Met Thr Pro Arg Ser Glu Gly Ser Ser
145                 150                 155                 160
```

```
Val Asn Leu Ser Pro Pro Leu Glu Gln Cys Val Pro Asp Arg Gly Gln
            165                 170                 175

Gln Tyr Gln Gly Arg Leu Ala Val Thr Thr His Gly Leu Pro Cys Leu
        180                 185                 190

Ala Trp Ala Ser Ala Gln Ala Lys Ala Leu Ser Lys His Gln Asp Phe
    195                 200                 205

Asn Ser Ala Val Gln Leu Val Glu Asn Phe Cys Arg Asn Pro Asp Gly
210                 215                 220

Asp Glu Glu Gly Val Trp Cys Tyr Val Ala Gly Lys Pro Gly Asp Phe
225                 230                 235                 240

Gly Tyr Cys Asp Leu Asn Tyr Cys Glu Glu Ala Val Glu Glu Glu Thr
                245                 250                 255

Gly Asp Gly Leu Asp Glu Asp Ser Asp Arg Ala Ile Glu Gly Arg Thr
            260                 265                 270

Ala Thr Ser Glu Tyr Gln Thr Phe Phe Asn Pro Arg Thr Phe Gly Ser
        275                 280                 285

Gly Glu Ala Asp Cys Gly Leu Arg Pro Leu Phe Glu Lys Lys Ser Leu
    290                 295                 300

Glu Asp Lys Thr Glu Arg Glu Leu Leu Glu Ser Tyr Ile Asp Gly Arg
305                 310                 315                 320

Ile Val Glu Gly Ser Asp Ala Glu Ile Gly Met Ser Pro Trp Gln Val
                325                 330                 335

Met Leu Phe Arg Lys Ser Pro Gln Glu Leu Leu Cys Gly Ala Ser Leu
            340                 345                 350

Ile Ser Asp Arg Trp Val Leu Thr Ala Ala His Cys Leu Leu Tyr Pro
        355                 360                 365

Pro Trp Asp Lys Asn Phe Thr Glu Asn Asp Leu Leu Val Arg Ile Gly
    370                 375                 380

Lys His Ser Arg Thr Arg Tyr Glu Arg Asn Ile Glu Lys Ile Ser Met
385                 390                 395                 400

Leu Glu Lys Ile Tyr Ile His Pro Arg Tyr Asn Trp Arg Glu Asn Leu
                405                 410                 415

Asp Arg Asp Ile Ala Leu Met Lys Leu Lys Lys Pro Val Ala Phe Ser
            420                 425                 430

Asp Tyr Ile His Pro Val Cys Leu Pro Asp Arg Glu Thr Ala Ala Ser
        435                 440                 445

Leu Leu Gln Ala Gly Tyr Lys Gly Arg Val Thr Gly Trp Gly Asn Leu
    450                 455                 460

Lys Glu Thr Trp Thr Ala Asn Val Val Glu Arg Pro Val Cys Lys Asp
465                 470                 475                 480

Ser Thr Arg Ile Arg Ile Thr Asp Asn Met Phe Cys Ala Gly Tyr Lys
                485                 490                 495

Pro Asp Glu Gly Lys Arg Gly Asp Ala Cys Glu Gly Asp Ser Gly Gly
            500                 505                 510

Pro Phe Val Met Lys Ser Pro Phe Asn Asn Arg Trp Tyr Gln Met Gly
        515                 520                 525

Ile Val Ser Trp Gly Glu Gly Cys Asp Arg Asp Gly Lys Tyr Gly Phe
    530                 535                 540

Tyr Thr His Val Phe Arg Leu Lys Lys Trp Ile Gln Lys Val Ile Asp
545                 550                 555                 560

Gln Phe Gly Glu
```